US009895692B2

(12) United States Patent
Battrell et al.

(10) Patent No.: US 9,895,692 B2
(45) Date of Patent: *Feb. 20, 2018

(54) SAMPLE-TO-ANSWER MICROFLUIDIC CARTRIDGE

(71) Applicant: Micronics, Inc., Redmond, WA (US)

(72) Inventors: C. Frederick Battrell, Wenatchee, WA (US); Isaac Sprague, Kirkland, WA (US); Matthew Scott Bragd, Mercer Island, WA (US); Jason Capodanno, Redmond, WA (US)

(73) Assignee: Micronics, Inc., Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/819,182

(22) Filed: Aug. 5, 2015

(65) Prior Publication Data
US 2016/0193603 A1    Jul. 7, 2016

Related U.S. Application Data

(63) Continuation of application No. 13/575,897, filed as application No. PCT/US2011/022973 on Jan. 28, 2011, now Pat. No. 9,132,423.
(Continued)

(51) Int. Cl.
*B01L 3/00* (2006.01)
*B01L 7/00* (2006.01)
(Continued)

(52) U.S. Cl.
CPC ............ *B01L 3/50273* (2013.01); *B01L 3/52* (2013.01); *B01L 7/52* (2013.01); *B01L 7/525* (2013.01);
(Continued)

(58) Field of Classification Search
USPC .................................. 422/502–505; 436/180
See application file for complete search history.

(56) References Cited

U.S. PATENT DOCUMENTS 3,013,467 A    12/1961    Minsky
3,799,742 A     3/1974    Coleman
(Continued)

FOREIGN PATENT DOCUMENTS

CN    1146017 A    3/1997
CN    1253625 A    5/2000
(Continued)

OTHER PUBLICATIONS

Al Zahrani et al., "Accuracy and Utility of Commercially Available Amplification and Serologic Tests for the Diagnosis of Minimal Pulmonary Tuberculosis," *Am J Respir Crit Care Med* 162:1323-1329, 2000.
(Continued)

*Primary Examiner* — Dean Kwak
(74) *Attorney, Agent, or Firm* — Seed IP Law Group LLP

(57) ABSTRACT

A microfluidic cartridge and methods for performing a diagnostic, molecular or biochemical assay thereon, where all dried and/or liquid reagents necessary for the assay are contained in the cartridge and the assay requires only the addition of sample. Pneumohydraulic features, chamber and diaphragm technologies are introduced for overcoming the problems of bubble interference and reagent washout during operation of a microfluidic cartridge. The cartridges are inserted into a host instrument for performance of an assay and the cartridge is supplied as a consumable.

13 Claims, 21 Drawing Sheets

Related U.S. Application Data

(60) Provisional application No. 61/299,534, filed on Jan. 29, 2010.

(51) Int. Cl.
    *G01N 1/10*      (2006.01)
    *G01N 21/03*     (2006.01)
    *G01N 21/17*     (2006.01)
    *G01N 21/64*     (2006.01)

(52) U.S. Cl.
    CPC ... *B01L 2200/0684* (2013.01); *B01L 2200/14* (2013.01); *B01L 2200/16* (2013.01); *B01L 2300/044* (2013.01); *B01L 2300/0672* (2013.01); *B01L 2300/087* (2013.01); *B01L 2300/0816* (2013.01); *B01L 2300/0864* (2013.01); *B01L 2300/0887* (2013.01); *B01L 2300/123* (2013.01); *B01L 2400/0481* (2013.01); *B01L 2400/0487* (2013.01); *B01L 2400/0638* (2013.01); *G01N 21/03* (2013.01); *G01N 21/0332* (2013.01); *G01N 21/17* (2013.01); *G01N 21/64* (2013.01); *G01N 21/6428* (2013.01); *Y10T 137/0318* (2015.04)

(56) References Cited

U.S. PATENT DOCUMENTS

| | | |
|---|---|---|
| 3,996,345 A | 12/1976 | Ullman et al. |
| 4,104,029 A | 8/1978 | Maier, Jr. |
| 4,235,960 A | 11/1980 | Sasse et al. |
| 4,304,257 A | 12/1981 | Webster |
| 4,366,241 A | 12/1982 | Tom et al. |
| 4,373,932 A | 2/1983 | Gribnau et al. |
| 4,610,678 A | 9/1986 | Weisman et al. |
| 4,683,195 A | 7/1987 | Mullis et al. |
| 4,683,202 A | 7/1987 | Mullis |
| 4,788,729 A | 12/1988 | Walker |
| 4,798,703 A | 1/1989 | Minekane |
| 4,800,159 A | 1/1989 | Mullis et al. |
| 4,810,630 A | 3/1989 | Craig et al. |
| 4,833,332 A | 5/1989 | Robertson, Jr. et al. |
| 4,837,168 A | 6/1989 | de Jaeger et al. |
| 4,848,722 A | 7/1989 | Webster |
| 4,855,240 A | 8/1989 | Rosenstein et al. |
| 4,869,282 A | 9/1989 | Sittler et al. |
| 4,883,750 A | 11/1989 | Whiteley et al. |
| 4,943,522 A | 7/1990 | Eisinger et al. |
| 4,956,302 A | 9/1990 | Gordon et al. |
| 4,965,188 A | 10/1990 | Mullis et al. |
| 5,038,852 A | 8/1991 | Johnson et al. |
| 5,075,078 A | 12/1991 | Osikowicz et al. |
| 5,100,626 A | 3/1992 | Levin |
| 5,120,643 A | 6/1992 | Ching et al. |
| 5,130,238 A | 7/1992 | Malek et al. |
| 5,141,850 A | 8/1992 | Cole et al. |
| 5,160,701 A | 11/1992 | Brown, III et al. |
| 5,192,980 A | 3/1993 | Dixon et al. |
| 5,225,163 A | 7/1993 | Andrews |
| 5,234,809 A | 8/1993 | Boom et al. |
| 5,252,459 A | 10/1993 | Tarcha et al. |
| 5,270,183 A | 12/1993 | Corbett et al. |
| 5,275,785 A | 1/1994 | May et al. |
| 5,296,703 A | 3/1994 | Tsien |
| 5,304,487 A | 4/1994 | Wilding et al. |
| 5,354,668 A | 10/1994 | Auerbach |
| 5,415,994 A | 5/1995 | Imrich et al. |
| 5,420,016 A | 5/1995 | Boguslaski et al. |
| 5,427,930 A | 6/1995 | Birkenmeyer et al. |
| 5,443,890 A | 8/1995 | Öhman |
| 5,455,166 A | 10/1995 | Walker |
| 5,486,335 A | 1/1996 | Wilding et al. |
| 5,498,392 A | 3/1996 | Wilding et al. |
| 5,504,013 A | 4/1996 | Senior |
| 5,543,026 A | 8/1996 | Hoff et al. |
| 5,582,989 A | 12/1996 | Caskey et al. |
| 5,587,128 A | 12/1996 | Wilding et al. |
| 5,591,645 A | 1/1997 | Rosenstein |
| 5,602,040 A | 2/1997 | May et al. |
| 5,622,871 A | 4/1997 | May et al. |
| 5,631,734 A | 5/1997 | Stern et al. |
| 5,635,358 A | 6/1997 | Wilding et al. |
| 5,635,602 A | 6/1997 | Cantor et al. |
| 5,639,428 A | 6/1997 | Cottingham |
| 5,656,503 A | 8/1997 | May et al. |
| 5,658,723 A | 8/1997 | Oberhardt |
| 5,660,370 A | 8/1997 | Webster |
| 5,660,990 A | 8/1997 | Rao et al. |
| 5,670,381 A | 9/1997 | Jou et al. |
| 5,707,807 A | 1/1998 | Kato |
| 5,716,842 A | 2/1998 | Baier et al. |
| 5,716,852 A | 2/1998 | Yager et al. |
| 5,718,567 A | 2/1998 | Rapp et al. |
| 5,724,404 A | 3/1998 | Garcia et al. |
| 5,726,026 A | 3/1998 | Wilding et al. |
| 5,726,404 A | 3/1998 | Brody |
| 5,726,751 A | 3/1998 | Altendorf et al. |
| 5,730,850 A | 3/1998 | Kambara et al. |
| 5,747,349 A | 5/1998 | van den Engh et al. |
| 5,748,827 A | 5/1998 | Holl et al. |
| 5,759,014 A | 6/1998 | Van Lintel |
| 5,770,460 A | 6/1998 | Pawlak et al. |
| 5,798,273 A | 8/1998 | Shuler et al. |
| 5,856,174 A | 1/1999 | Lipshutz et al. |
| 5,863,502 A | 1/1999 | Southgate et al. |
| 5,863,801 A | 1/1999 | Southgate et al. |
| 5,872,710 A | 2/1999 | Kameyama |
| 5,906,602 A | 5/1999 | Weber et al. |
| 5,922,210 A | 7/1999 | Brody et al. |
| 5,922,591 A | 7/1999 | Anderson et al. |
| 5,932,100 A | 8/1999 | Yager et al. |
| 5,932,799 A | 8/1999 | Moles |
| 5,948,684 A | 9/1999 | Weigl et al. |
| 5,955,029 A | 9/1999 | Wilding et al. |
| 5,965,410 A | 10/1999 | Chow et al. |
| 5,971,158 A | 10/1999 | Yager et al. |
| 5,971,355 A | 10/1999 | Biegelsen et al. |
| 5,972,710 A | 10/1999 | Weigl et al. |
| 5,972,721 A | 10/1999 | Bruno et al. |
| 5,974,867 A | 11/1999 | Forster et al. |
| 5,989,813 A | 11/1999 | Gerdes |
| 6,001,307 A | 12/1999 | Naka et al. |
| 6,007,309 A | 12/1999 | Hartley |
| 6,007,775 A | 12/1999 | Yager |
| 6,018,616 A | 1/2000 | Schaper |
| 6,020,187 A | 2/2000 | Tam |
| 6,037,168 A | 3/2000 | Brown |
| 6,057,167 A | 5/2000 | Shieh et al. |
| 6,068,752 A | 5/2000 | Dubrow et al. |
| 6,086,740 A | 7/2000 | Kennedy |
| 6,158,712 A | 12/2000 | Craig |
| 6,168,948 B1 | 1/2001 | Anderson et al. |
| 6,171,865 B1 | 1/2001 | Weigl et al. |
| 6,184,029 B1 | 2/2001 | Wilding et al. |
| 6,210,514 B1 | 4/2001 | Cheung et al. |
| 6,210,882 B1 | 4/2001 | Landers et al. |
| 6,272,939 B1 | 8/2001 | Frye et al. |
| 6,287,850 B1 | 9/2001 | Besemer et al. |
| 6,303,389 B1 | 10/2001 | Levin et al. |
| 6,309,875 B1 | 10/2001 | Gordon |
| 6,325,975 B1 | 12/2001 | Naka et al. |
| 6,326,211 B1 | 12/2001 | Anderson et al. |
| 6,368,876 B1 | 4/2002 | Huang et al. |
| 6,387,290 B1 | 5/2002 | Brody et al. |
| 6,390,791 B1 | 5/2002 | Maillefer et al. |
| 6,399,398 B1 | 6/2002 | Cunningham et al. |
| 6,418,968 B1 | 7/2002 | Pezzuto et al. |
| 6,431,212 B1 | 8/2002 | Hayenga et al. |
| 6,439,036 B1 | 8/2002 | Mansky |
| 6,468,807 B1 | 10/2002 | Svensson et al. |
| 6,488,896 B2 | 12/2002 | Weigl et al. |
| 6,506,346 B1 | 1/2003 | Monro |
| 6,541,213 B1 | 4/2003 | Weigl et al. |
| 6,541,274 B2 | 4/2003 | Nagle et al. |

(56) References Cited

U.S. PATENT DOCUMENTS

| | | |
|---|---|---|
| 6,562,209 B1 | 5/2003 | Sullivan et al. |
| 6,569,674 B1 | 5/2003 | McGarry et al. |
| 6,576,459 B2 | 6/2003 | Miles et al. |
| 6,581,899 B2 | 6/2003 | Williams |
| 6,614,030 B2 | 9/2003 | Maher et al. |
| 6,620,273 B2 | 9/2003 | Dai et al. |
| 6,632,655 B1 | 10/2003 | Mehta et al. |
| 6,635,487 B1 | 10/2003 | Lee et al. |
| 6,637,463 B1 | 10/2003 | Lei et al. |
| 6,664,104 B2 | 12/2003 | Pourahmadi et al. |
| 6,720,411 B2 | 4/2004 | Mirkin et al. |
| 6,729,352 B2 | 5/2004 | O'Connor et al. |
| 6,731,178 B2 | 5/2004 | Gailhard et al. |
| 6,731,781 B1 | 5/2004 | Shams et al. |
| 6,743,399 B1 | 6/2004 | Weigl et al. |
| 6,748,975 B2 | 6/2004 | Hartshorne et al. |
| 6,758,107 B2 | 7/2004 | Cabuz |
| 6,767,194 B2 | 7/2004 | Jeon et al. |
| 6,787,338 B2 | 9/2004 | Wittwer et al. |
| 6,793,753 B2 | 9/2004 | Unger et al. |
| 6,815,160 B1 | 11/2004 | Chien et al. |
| 6,843,263 B2 | 1/2005 | Kuo et al. |
| 6,872,566 B2 | 3/2005 | Vischer et al. |
| 6,901,949 B2 | 6/2005 | Cox et al. |
| 6,916,113 B2 | 7/2005 | Van de Goor et al. |
| 6,951,632 B2 | 10/2005 | Unger et al. |
| 6,953,675 B2 | 10/2005 | Leung et al. |
| 6,953,676 B1 | 10/2005 | Wilding et al. |
| 6,955,738 B2 | 10/2005 | Derand et al. |
| 6,974,119 B2 | 12/2005 | Brendle et al. |
| 6,974,669 B2 | 12/2005 | Mirkin et al. |
| 7,010,391 B2 | 3/2006 | Handique et al. |
| 7,052,594 B2 | 5/2006 | Pelrine et al. |
| 7,087,414 B2 | 8/2006 | Gerdes et al. |
| 7,141,416 B2 | 11/2006 | Krutzik |
| 7,153,673 B2 | 12/2006 | Stern |
| 7,223,363 B2 | 5/2007 | McNeely et al. |
| 7,223,371 B2 | 5/2007 | Hayenga et al. |
| 7,226,562 B2 | 6/2007 | Holl et al. |
| 7,235,400 B2 | 6/2007 | Adey |
| 7,318,913 B2 | 1/2008 | Loeffler et al. |
| 7,416,892 B2 | 8/2008 | Battrell et al. |
| 7,445,926 B2 | 11/2008 | Mathies et al. |
| 7,514,212 B2 | 4/2009 | Prudent et al. |
| 7,517,651 B2 | 4/2009 | Marshall et al. |
| 7,541,147 B2 | 6/2009 | Marshall et al. |
| 7,544,506 B2 | 6/2009 | Breidford et al. |
| 7,607,641 B1 | 10/2009 | Yuan |
| 7,615,370 B2 | 11/2009 | Streit et al. |
| 7,648,835 B2 | 1/2010 | Breidford et al. |
| 7,695,683 B2 | 4/2010 | Quan et al. |
| 7,749,444 B2 | 7/2010 | Yamada et al. |
| 7,763,453 B2 | 7/2010 | Clemmens et al. |
| 7,785,776 B2 | 8/2010 | Wittwer et al. |
| 7,832,429 B2 | 11/2010 | Young et al. |
| 7,906,317 B2 | 3/2011 | Lee et al. |
| 7,955,836 B2 | 6/2011 | Clemmens et al. |
| 8,104,497 B2 | 1/2012 | Unger et al. |
| 8,104,514 B2 | 1/2012 | Fernandes et al. |
| 8,110,392 B2 | 2/2012 | Battrell et al. |
| 8,222,023 B2 | 7/2012 | Battrell et al. |
| 8,329,453 B2 | 12/2012 | Battrell et al. |
| 8,431,389 B2 | 4/2013 | Battrell et al. |
| 8,716,007 B2 | 5/2014 | Battrell et al. |
| 8,747,779 B2 | 6/2014 | Sprague et al. |
| 8,772,017 B2 | 7/2014 | Battrell et al. |
| 9,056,291 B2 | 6/2015 | Battrell et al. |
| 9,132,423 B2 | 9/2015 | Battrell et al. |
| 2001/0046701 A1 | 11/2001 | Schulte et al. |
| 2002/0081934 A1 | 6/2002 | Murao et al. |
| 2002/0086443 A1 | 7/2002 | Bamdad |
| 2002/0137196 A1 | 9/2002 | Miles et al. |
| 2002/0160518 A1 | 10/2002 | Hayenga et al. |
| 2002/0192676 A1 | 12/2002 | Madonna et al. |
| 2002/0195152 A1 | 12/2002 | Fernandes et al. |
| 2003/0008308 A1 | 1/2003 | Enzelberger et al. |
| 2003/0013184 A1 | 1/2003 | Streit et al. |
| 2003/0032028 A1 | 2/2003 | Dace et al. |
| 2003/0073229 A1 | 4/2003 | Greenstein et al. |
| 2003/0124619 A1 | 7/2003 | Weigl et al. |
| 2003/0129756 A1 | 7/2003 | Thorne et al. |
| 2003/0136178 A1 | 7/2003 | Cabuz |
| 2003/0152927 A1 | 8/2003 | Jakobsen et al. |
| 2003/0175990 A1 | 9/2003 | Hayenga et al. |
| 2003/0215825 A1 | 11/2003 | Tong |
| 2003/0224434 A1 | 12/2003 | Wittwer et al. |
| 2004/0005718 A1 | 1/2004 | Fukushima |
| 2004/0018611 A1 | 1/2004 | Ward et al. |
| 2004/0024051 A1 | 2/2004 | Holton |
| 2004/0037739 A1 | 2/2004 | McNeely et al. |
| 2004/0081997 A1 | 4/2004 | Stern |
| 2004/0115094 A1 | 6/2004 | Gumbrecht et al. |
| 2004/0121364 A1 | 6/2004 | Chee et al. |
| 2004/0124384 A1 | 7/2004 | Biegelsen et al. |
| 2004/0189311 A1 | 9/2004 | Glezer et al. |
| 2004/0209354 A1 | 10/2004 | Mathies et al. |
| 2004/0224339 A1 | 11/2004 | Numajiri et al. |
| 2004/0226348 A1 | 11/2004 | Bruce, III et al. |
| 2004/0248167 A1 | 12/2004 | Quake et al. |
| 2005/0013732 A1 | 1/2005 | Battrell et al. |
| 2005/0019792 A1 | 1/2005 | McBride et al. |
| 2005/0019898 A1 | 1/2005 | Adey et al. |
| 2005/0037397 A1 | 2/2005 | Mirkin et al. |
| 2005/0106066 A1 | 5/2005 | Saltsman et al. |
| 2005/0106742 A1 | 5/2005 | Wahl et al. |
| 2005/0129582 A1 | 6/2005 | Breidford et al. |
| 2005/0136552 A1 | 6/2005 | Buechler |
| 2005/0142582 A1 | 6/2005 | Doyle et al. |
| 2005/0157301 A1* | 7/2005 | Chediak .............. G01N 21/05 356/417 |
| 2005/0161669 A1 | 7/2005 | Jovanovich et al. |
| 2005/0164373 A1 | 7/2005 | Oldham et al. |
| 2005/0186585 A1 | 8/2005 | Juncosa et al. |
| 2005/0205816 A1 | 9/2005 | Hayenga et al. |
| 2005/0217741 A1 | 10/2005 | Bohm |
| 2005/0221281 A1 | 10/2005 | Ho |
| 2005/0284817 A1 | 12/2005 | Fernandez et al. |
| 2006/0003440 A1 | 1/2006 | Streit et al. |
| 2006/0073484 A1 | 4/2006 | Mathies et al. |
| 2006/0076068 A1 | 4/2006 | Young et al. |
| 2006/0127886 A1 | 6/2006 | Kaylor et al. |
| 2006/0166375 A1 | 7/2006 | Hawkins et al. |
| 2006/0178568 A1 | 8/2006 | Danna et al. |
| 2006/0246575 A1 | 11/2006 | Lancaster et al. |
| 2006/0263816 A1 | 11/2006 | Laikhter et al. |
| 2006/0264782 A1 | 11/2006 | Holmes et al. |
| 2006/0275852 A1 | 12/2006 | Montagu et al. |
| 2006/0275893 A1 | 12/2006 | Ishii et al. |
| 2006/0292588 A1 | 12/2006 | Chou et al. |
| 2006/0292630 A1 | 12/2006 | Fukumoto |
| 2007/0009383 A1 | 1/2007 | Bedingham et al. |
| 2007/0014695 A1 | 1/2007 | Yue et al. |
| 2007/0042427 A1 | 2/2007 | Gerdes et al. |
| 2007/0125947 A1 | 6/2007 | Sprinzak et al. |
| 2007/0154895 A1 | 7/2007 | Spaid et al. |
| 2007/0183935 A1 | 8/2007 | Clemmens et al. |
| 2007/0190525 A1 | 8/2007 | Gu et al. |
| 2007/0219366 A1 | 9/2007 | Gumbrecht et al. |
| 2007/0234785 A1 | 10/2007 | Beerling et al. |
| 2007/0243603 A1 | 10/2007 | Einsle et al. |
| 2007/0280856 A1 | 12/2007 | Ulmanella et al. |
| 2007/0292858 A1 | 12/2007 | Chen et al. |
| 2008/0050283 A1 | 2/2008 | Chou et al. |
| 2008/0081341 A1 | 4/2008 | Maher et al. |
| 2008/0226500 A1 | 9/2008 | Shikida et al. |
| 2008/0260586 A1 | 10/2008 | Boamfa |
| 2008/0274511 A1 | 11/2008 | Tan et al. |
| 2008/0297792 A1 | 12/2008 | Kim et al. |
| 2009/0000678 A1 | 1/2009 | Therriault et al. |
| 2009/0017483 A1 | 1/2009 | Yamaoka et al. |
| 2009/0047713 A1 | 2/2009 | Handique |
| 2009/0061450 A1 | 3/2009 | Hunter |
| 2009/0148847 A1 | 6/2009 | Kokoris et al. |

(56) References Cited

U.S. PATENT DOCUMENTS

| | | | |
|---|---|---|---|
| 2009/0148933 A1* | 6/2009 | Battrell | B01F 11/0071 435/287.2 |
| 2009/0181411 A1 | 7/2009 | Battrell et al. | |
| 2009/0298059 A1 | 12/2009 | Gumbrecht et al. | |
| 2009/0325203 A1 | 12/2009 | Jenny et al. | |
| 2009/0325276 A1 | 12/2009 | Battrell et al. | |
| 2010/0041049 A1 | 2/2010 | Smith et al. | |
| 2010/0112723 A1 | 5/2010 | Battrell et al. | |
| 2010/0291588 A1 | 11/2010 | McDevitt et al. | |
| 2011/0151479 A1 | 6/2011 | Stevens et al. | |
| 2011/0207621 A1 | 8/2011 | Montagu et al. | |
| 2012/0028342 A1 | 2/2012 | Ismagilov et al. | |
| 2012/0064597 A1 | 3/2012 | Clemmens et al. | |
| 2012/0071342 A1 | 3/2012 | Lochhead et al. | |
| 2012/0135511 A1 | 5/2012 | Battrell et al. | |
| 2012/0156750 A1 | 6/2012 | Battrell et al. | |
| 2012/0164383 A1 | 6/2012 | Sollmann | |
| 2012/0164627 A1 | 6/2012 | Battrell et al. | |
| 2012/0177543 A1 | 7/2012 | Battrell et al. | |
| 2012/0329142 A1 | 12/2012 | Battrell et al. | |
| 2013/0011912 A1 | 1/2013 | Battrell et al. | |
| 2014/0349381 A1 | 11/2014 | Battrell et al. | |
| 2015/0158026 A1 | 6/2015 | Battrell et al. | |
| 2015/0321193 A1 | 11/2015 | Sprague et al. | |
| 2015/0346097 A1 | 12/2015 | Battrell et al. | |
| 2015/0352549 A1 | 12/2015 | Kolb et al. | |
| 2016/0090588 A1 | 3/2016 | Lofquist et al. | |
| 2016/0102340 A1 | 4/2016 | Bouzek | |
| 2017/0113221 A1 | 4/2017 | Hoffman et al. | |

FOREIGN PATENT DOCUMENTS

| | | |
|---|---|---|
| CN | 102203605 A | 9/2011 |
| CN | 102602087 A | 7/2012 |
| DE | 20 2004 012 163 U1 | 11/2004 |
| EP | 0 320 308 A2 | 6/1989 |
| EP | 0 329 822 A2 | 8/1989 |
| EP | 0 399 859 A1 | 11/1990 |
| EP | 0 517 631 A1 | 12/1992 |
| EP | 1 180 135 B1 | 8/2005 |
| EP | 1 659 405 A1 | 5/2006 |
| EP | 1 707 965 A1 | 10/2006 |
| EP | 1 726 940 A1 | 11/2006 |
| EP | 1 792 654 A2 | 6/2007 |
| EP | 2 202 328 A1 | 6/2010 |
| GB | 2 202 328 A | 9/1988 |
| JP | 52-55679 A | 5/1977 |
| JP | 10-82773 A | 3/1998 |
| JP | 2000-314719 A | 11/2000 |
| JP | 2003-207454 A | 7/2003 |
| JP | 2004-028589 A | 1/2004 |
| JP | 2004-333452 A | 11/2004 |
| JP | 2005-512071 A | 4/2005 |
| JP | 2005-531006 A | 10/2005 |
| JP | 2006-73371 A | 3/2006 |
| JP | 2006-84459 A | 3/2006 |
| JP | 2006-90774 A | 4/2006 |
| JP | 2006-122743 A | 5/2006 |
| JP | 2006-517029 A | 7/2006 |
| JP | 2006-246777 A | 9/2006 |
| JP | 2006-520190 A | 9/2006 |
| JP | 2007-514142 A | 5/2007 |
| JP | 2007-532918 A | 11/2007 |
| JP | 2008-503722 A | 2/2008 |
| JP | 2008-89597 A | 4/2008 |
| JP | 2008-96375 A | 4/2008 |
| JP | 2008-537063 A | 9/2008 |
| JP | 2009-14529 A | 1/2009 |
| JP | 2009-019962 A | 1/2009 |
| JP | 2009-513966 A | 4/2009 |
| JP | 2009-529883 A | 8/2009 |
| JP | 2009-255083 A | 11/2009 |
| JP | 2010-78508 A | 4/2010 |
| WO | 86/06488 A1 | 11/1986 |
| WO | 88/08534 A1 | 11/1988 |
| WO | 88/10315 A1 | 12/1988 |
| WO | 89/06700 A1 | 7/1989 |
| WO | 89/09284 A1 | 10/1989 |
| WO | 91/12336 A1 | 8/1991 |
| WO | 96/33399 A1 | 10/1996 |
| WO | 98/49543 A1 | 11/1998 |
| WO | 00/63670 A1 | 10/2000 |
| WO | 01/070381 A2 | 9/2001 |
| WO | 02/001184 A1 | 1/2002 |
| WO | 02/012896 A1 | 2/2002 |
| WO | 02/041994 A2 | 5/2002 |
| WO | 02/072262 A1 | 9/2002 |
| WO | 02/081934 A2 | 10/2002 |
| WO | 03/015923 A1 | 2/2003 |
| WO | 03/031977 A2 | 4/2003 |
| WO | 03/049860 A1 | 6/2003 |
| WO | 03/054523 A2 | 7/2003 |
| WO | 03/097831 A1 | 11/2003 |
| WO | 03/101887 A2 | 12/2003 |
| WO | 03/102546 A2 | 12/2003 |
| WO | 2004/055198 A2 | 7/2004 |
| WO | 2004/061085 A2 | 7/2004 |
| WO | 2004/065010 A2 | 8/2004 |
| WO | 2004/065930 A2 | 8/2004 |
| WO | 2005/016529 A1 | 2/2005 |
| WO | 2005/022154 A1 | 3/2005 |
| WO | 2005/066638 A1 | 7/2005 |
| WO | 2005/069015 A1 | 7/2005 |
| WO | 2005/106024 A2 | 11/2005 |
| WO | 2006/018811 A1 | 2/2006 |
| WO | 2006/035830 A1 | 4/2006 |
| WO | 2006/052652 A2 | 5/2006 |
| WO | 2006/076567 A2 | 7/2006 |
| WO | 2006/083833 A2 | 8/2006 |
| WO | 2006/125767 A1 | 11/2006 |
| WO | 2007/049009 A1 | 5/2007 |
| WO | 2007/064635 A1 | 6/2007 |
| WO | 2007/106579 A2 | 9/2007 |
| WO | 2007/106580 A2 | 9/2007 |
| WO | 2007/109584 A1 | 9/2007 |
| WO | 2008/002462 A2 | 1/2008 |
| WO | 2008/070198 A2 | 6/2008 |
| WO | 2008/101732 A1 | 8/2008 |
| WO | 2008/147382 A1 | 12/2008 |
| WO | 2009/018473 A1 | 2/2009 |
| WO | 2009/037361 A1 | 3/2009 |
| WO | 2009/105711 A1 | 8/2009 |
| WO | 2010/025302 A2 | 3/2010 |
| WO | 2010/088514 A1 | 8/2010 |
| WO | 2011/094577 A2 | 8/2011 |
| WO | 2012/071069 A1 | 5/2012 |
| WO | 2013/052318 A1 | 4/2013 |
| WO | 2014/100732 A1 | 6/2014 |
| WO | 2014/182847 A1 | 11/2014 |

OTHER PUBLICATIONS

Aoki et al., "Serine Repeat Antigen (SERA5) Is Predominantly Expressed among the SERA Multigene Family of Plasmodium falciparum, and the Acquired Antibody Titers Correlate with Serum Inhibition of the Parasite Growth," *The Journal of Biological Chemistry* 277(49):47533-47540, Dec. 2002.

Arar et al., "Synthesis and Antiviral Activity of Peptide-Oligonucleotide Conjugates Prepared by Using $N_\alpha$-(Bromoacetyl)peptides," *Bioconjugate Chem.* 6(5):573-577, 1995.

Arikan et al., "Anti-Kp 90 IgA Antibodies in the Diagnosis of Active Tuberculosis," *CHEST* 114(5):1253-1257, Nov. 1998.

Birkelund, "The molecular biology and diagnostics of Chlamydia trachomatis," *Danish Medical Bulletin* 39(4):304-320, Aug. 1992.

Bongartz et al., "Improved biological activity of antisense oligonucleotides conjugated to a fusogenic peptide," *Nucleic Acids Research* 22(22):4681-4688, 1994.

Bowden et al., "Using Self-Administered Tampons to Diagnose STDs," *AIDS Patient Care and STDs* 12(1):29-32, 1998.

(56) References Cited

OTHER PUBLICATIONS

Carmona et al., "The use of fluorescence resonance energy transfer (FRET) peptides for measurement of clinically important proteolytic enzymes," *An Acad Bras Cienc* 81(3):381-392.

Chan et al., "Polymer surface modification by plasmas and photons," *Surface Science Reports* 24:1-54, 1996.

Chernesky et al., "Clinical Evaluation of the Sensitivity and Specificity of a Commercially Available Enzyme Immunoassay for Detection of Rubella Virus-Specific Immunoglobulin M," *J. Clin. Microbiol.* 20(3):400-404, Sep. 1984.

Chernesky et al., "Detection of Chlamydia trachomatis Antigens by Enzyme Immunoassay and Immunofluorescence in Genital Specimens from Symptomatic and Asymptomatic Men and Women," *The Journal of Infectious Diseases* 154(1):141-148, Jul. 1986.

Chou et al., "Prevention of pre-PCR mis-priming and primer dimerization improves low-copy-number amplifications," *Nucleic Acids Research* 20(7):1717-1723, 1992.

Crotchfelt et al., "Detection of Neisseria gonorrhoeae and Chlamydia trachomatis in Genitourinary Specimens from Men and Women by a Coamplification PCR Assay," *J. Clin. Microbiol.* 35(6):1536-1540, Jun. 1997.

Cuzzubbo et al., "Use of Recombinant Envelope Proteins for Serological Diagnosis of Dengue Virus Infection in an Immunochromatographic Assay," *Clin. Diagn. Lab. Immunol.* 8(6):1150-1155, 2001.

D'Aquila et al., "Maximizing sensitivity and specificity of PCR by pre-amplification heating," *Nucleic Acids Research* 19(13):3749, 1991.

Dean et al., "Comprehensive human genome amplification using multiple displacement amplification," *PNAS* 99(8):5261-5266, Apr. 2002.

Detter et al., "Isothermal Strand-Displacement Amplification Applications for High-Throughput Genomics," *Genomics* 80(6):691-698, Dec. 2002.

Edelstein et al., "The BARC biosensor applied to the detection of biological warfare agents," *Biosensors & Bioelectronics* 14:805-813, 2000.

Eritja et al., "Synthesis of Defined Peptide-Oligonucleotide Hybrids Containing a Nuclear Transport Signal Sequence," *Tetrahedron* 47(24):4113-4120, 1991.

Fontana et al., "Performance of Strand Displacement Amplification Assay in the Detection of Chlamydia trachomatis and Neisseria gonorrhoeae," *Jpn. J. Infect. Dis.* 58:283-288, 2005.

Frame et al., "Identification and Typing of Herpes Simplex Virus by Enzyme Immunoassay with Monoclonal Antibodies," *J. Clin. Microbiol.* 20(2):162-166, Aug. 1984.

Gallo et al., "Study of viral integration of HPV-16 in young patients with LSIL," *J Clin Pathol* 56:532-536, 2003.

Garbassi et al., *Polymer Surfaces-From Physics to Technology*, John Wiley and Sons, Baltimore, Md., 1998, pp. 238-241.

Ghai et al., "Identification, expression, and functional characterization of MAEBL, a sporozoite and asexual blood stage chimeric erythrocyte-binding protein of Plasmodium falciparum," *Molecular & Biochemical Parasitology* 123:35-45, 2002.

Gijs, "Magnetic bead handling on-chip: new opportunities for analytical applications," *Microfluid Nanofluid* 1:22-40, 2004.

Gomes et al., "Immunoreactivity and differential developmental expression of known and putative Chlamydia trachomatis membrane proteins for biologically variant serovars representing distinct disease groups," *Microbes and Infection* 7:410-420, 2005.

Graham et al., "Magnetoresistive-based biosensors and biochips," *TRENDS in Biotechnology* 22(9):455-462, Sep. 2004.

Graves et al., "Development of Antibody to Measles Virus Polypeptides During Complicated and Uncomplicated Measles Virus Infections," *Journal of Virology* 49(2):409-412, Feb. 1984.

Grover et al., "Monolithic membrane valves and diaphragm pumps for practical large-scale integration into glass microfluidic devices," *Sensors and Actuators B* 89:315-323, 2003.

Hardt et al., "Passive micromixers for applications in the microreactor and mTAS fields," *Microfluid Nanofluid* 1:108-118, 2005.

Harris et al., "Typing of Dengue Viruses in Clinical Specimens and Mosquitoes by Single-Tube Multiplex Reverse Transcriptase PCR," *J. Clin. Microbiol.* 36(9):2634-2639, Sep. 1998.

Harrison et al., "Synthesis and hybridization analysis of a small library of peptide—oligonucleotide conjugates," *Nucleic Acids Research* 26(13):3136-3145, 1998.

Hummel et al., "Development of quantitative gene-specific real-time RT-PCR assays for the detection of measles virus in clinical specimens," *Journal of Virological Methods* 132:166-173, 2006.

Hung et al., "A specificity enhancer for polymerase chain reaction," *Nucleic Acids Research* 18(16):4953, Jun. 1990.

Innis et al., (eds.), *PCR Protocols: A Guide to Methods and Applications*, Academic Press, Inc., San Diego, California, 1990, 480 pages.

Jacobs et al., "Detection of *Streptococcus pneumoniae* Antigen in Bronchoalveolar Lavage Fluid Samples by a Rapid Immunochromatographic Membrane Assay," *J. Clin. Microbiol.* 43(8):4037-4040, 2005.

Joung et al., "Micropumps Based on Alternating High-Gradient Magnetic Fields," *IEEE Transactions on Magnetics* 36(4):2012-2014, Jul. 2000.

Kanehisa, "Use of statistical criteria for screening potential homologies in nucleic acid sequences," *Nucleic Acids Research* 12(1):203-213, Jan. 1984.

Kellogg et al., "TaqStart Antibody: "Hot Start" PCR Facilitated by a Neutralizing Monoclonal Antibody Directed Against Taq DNA Polymerase," *BioTechniques* 16(6):1134-1137, Jun. 1994.

Kennedy et al., "Protein-Protein Coupling Reactions and the Applications of Protein Conjugates," *Clinica Chimica Acta* 70(1):1-31, Jul. 1976.

Khan et al., "Antibiotic Resistance, Virulence Gene, and Molecular Profiles of Shiga Toxin-Producing *Escherichia coli* Isolates from Diverse Sources in Calcutta, India," *J. Clin. Microbiol.* 40(6):2009-2015, Jun. 2002.

Khan et al., "Prevalence and Genetic Profiling of Virulence Determinants of Non-O157 Shiga Toxin-Producing *Escherichia coli* Isolated from Cattle, Beef, and Humans, Calcutta, India," *Emerging Infectious Diseases* 8(1):54-62, Jan. 2002.

Kittigul et al., "Use of a Rapid Immunochromatographic Test for Early Diagnosis of Dengue Virus Infection," *Eur. J. Clin. Microbiol. Infect. Dis.* 21(3):224-226, Mar. 2002.

Knox et al., "Evaluation of Self-Collected Samples in Contrast to Practitioner-Collected Samples for Detection of Chlamydia trachomatis, Neisseria gonorrhoeae, and Trichomonas vaginalis by Polymerase Chain Reaction Among Women Living in Remote Areas," *Sexually Transmitted Diseases* 29(11):647-654, Nov. 2002.

Kremer et al., "Measles Virus Genotyping by Nucleotide-Specific Multiplex PCR," *J. Clin. Microbiol.* 42(7):3017-3022, Jul. 2004.

Kuipers et al., "Detection of Chlamydia trachomatis in peripheral blood leukocytes of reactive arthritis patients by polymerase chain reaction," *Arthritis & Rheumatism* 41(10):1894-1895, Oct. 1998.

Kuipers et al., "Sensitivities of PCR, MicroTrak, ChlamydiaEIA, IDEIA, and PACE 2 for Purified Chlamydia trachomatis Elementary Bodies in Urine, Peripheral Blood, Peripheral Blood Leukocytes, and Synovial Fluid," *J. Clin. Microbiol.* 33(12):3186-3190, Dec. 1995.

Kuno, "Universal diagnostic RT-PCR protocol for arboviruses," *Journal of Virological Methods* 72:27-41, 1998.

Kwoh et al., "Transcription-based amplification system and detection of amplified human immunodeficiency virus type 1 with a bead-based sandwich hybridization format," *Proc. Natl. Acad. Sci. U.S.A.* 86:1173-1177, Feb. 1989.

Lage et al., "Whole Genome Analysis of Genetic Alterations in Small DNA Samples Using Hyperbranched Strand Displacement Amplification and Array-CGH," *Genome Research* 13:294-307, 2003.

Lanciotti et al., "Rapid Detection and Typing of Dengue Viruses from Clinical Samples by Using Reverse Transcriptase-Polymerase Chain Reaction," *J. Clin. Microbiol.* 30(3):545-551, Mar. 1992.

Leclerc et al., "Meager genetic variability of the human malaria agent Plasmodium vivax," *PNAS* 101(40):14455-14460, Oct. 5, 2004.

(56) References Cited

OTHER PUBLICATIONS

Lee et al., "Implementation of Force Differentiation in the Immunoassay," *Analytical Biochemistry* 287:261-271, 2000.
Leung et al., "Rapid antigen detection testing in diagnosing group A b-hemolytic streptococcal pharyngitis," *Expert. Rev. Mol. Diagn.* 6(5):761-766, 2006.
Lindegren et al., "Optimized Diagnosis of Acute Dengue Fever in Swedish Travelers by a Combination of Reverse Transcription-PCR and Immunoglobulin M Detection," *J. Clin. Microbiol.* 43(6):2850-2855, Jun. 2005.
Ling et al., "The Plasmodium falciparum clag9 gene encodes a rhoptry protein that is transferred to the host erythrocyte upon invasion," *Molecular Microbiology* 52(1):107-118, 2004.
Lundquist et al., "Human Recombinant Antibodies against Plasmodium falciparum Merozoite Surface Protein 3 Cloned from Peripheral Blood Leukocytes of Individuals with Immunity to Malaria Demonstrate Antiparasitic Properties," *Infect. Immun.* 74(6):3222-3231, Jun. 2006.
Luxton et al., "Use of External Magnetic Fields to Reduce Reaction Times in an Immunoassay Using Micrometer-Sized Paramagnetic Particles as Labels (Magnetoimmunoassay)," *Anal. Chem.* 76(6):1715-1719, Mar. 2004.
Mahony et al., "Chlamydia trachomatis confirmatory testing of PCR-positive genitourinary specimens using a second set of plasmid primers," *Molecular and Cellular Probes* 6:381-388, 1992.
Mahony et al., "Comparison of Plasmid- and Chromosome-Based Polymerase Chain Reaction Assays for Detecting Chlamydia trachomatis Nucleic Acids," *J. Clin. Microbiol.* 31(7):1753-1758, Jul. 1993.
Mahony et al., "Detection of Antichlamydial Immunoglobulin G and M Antibodies by Enzyme-Linked Immunosorbent Assay," *J. Clin. Microbiol.* 18(2):270-275, Aug. 1983.
Mahony et al., "Multiplex PCR for Detection of Chlamydia trachomatis and Neisseria gonorrhoeae in Genitourinary Specimens," *J. Clin. Microbiol.* 33(11):3049-3053, Nov. 1995.
Mahony, "Multiplex Polymerase Chain Reaction for the Diagnosis of Sexually Transmitted Diseases," *Clinics in Laboratory Medicine* 16(1):61-71, Mar. 1996.
Mayta et al., "Use of a reliable PCR assay for the detection of Neisseria gonorrhoeae in Peruvian patients," *Clinical Microbiology and Infection* 12(8):809-812, Aug. 2006.
Michon et al., "Naturally Acquired and Vaccine-Elicited Antibodies Block Erythrocyte Cytoadherence of the Plasmodium vivax Duffy Binding Protein," *Infect. Immun.* 68(6):3164-3171, Jun. 2000.
Migot-Nabias et al., "Immune Responses Against Plasmodium Falciparum Asexual Blood-Stage Antigens and Disease Susceptibility in Gabonese and Cameroonian Children," *Am. J. Trop. Med. Hyg.* 61(3):488-494, 1999.
Mitrani-Rosenbaum et al., "Simultaneous detection of three common sexually transmitted agents by polymerase chain reaction," *Am J Obstet Gynecol* 171(3):784-790, Sep. 1994.
Mohmmed et al., "Identification of karyopherin b as an immunogenic antigen of the malaria parasite using immune mice and human sera," *Parasite Immunology* 27:197-203, 2005.
Monis et al., "Nucleic acid amplification-based techniques for pathogen detection and identification," *Infection, Genetics and Evolution* 6:2-12, 2006.
Morré et al., "RNA Amplification by Nucleic Acid Sequence-Based Amplification with an Internal Standard Enables Reliable Detection of Chlamydia trachomatis in Cervical Scrapings and Urine Samples," *J. Clin. Microbiol.* 34(12):3108-3114, Dec. 1996.
Narum et al., "A novel Plasmodium falciparum erythrocyte binding protein-2 (EBP2/BAEBL) involved in erythrocyte receptor binding," *Molecular & Biochemical Parasitology* 119:159-168, 2002.
NCBI Database, GenBank Accession No. ACOL01000910, Jun. 9, 2009.
NCBI Database, GenBank Accession No. ACOL01004315, Jun. 9, 2009.
NCBI Database, GenBank Accession No. ACOL01004318, Jun. 9, 2009.
NCBI Database, GenBank Accession No. ACOL01004329, Jun. 9, 2009.
NCBI Database, GenBank Accession No. ACOL01004331, Jun. 9, 2009.
NCBI Database, GenBank Accession No. NP_473155, Jan. 3, 2007.
Nielsen et al., "Detection of Immunoglobulin G Antibodies to Cytomegalovirus Antigens by Antibody Capture Enzyme-Linked Immunosorbent Assay," *J. Clin. Microbiol.* 24(6):998-1003, Dec. 1986.
Notomi et al., "Loop-mediated isothermal amplification of DNA," *Nucleic Acids Research* 28(12):2-7, 2000.
Oeuvray et al., "Merozoite Surface Protein-3: A Malaria Protein Inducing Antibodies that Promote Plasmodium falciparum Killing by Cooperation With Blood Monocytes," *Blood* 84(5):1594-1602, Sep. 1994.
Ohara et al., "One-sided polymerase chain reaction: The amplification of cDNA," *Proc. Natl. Acad. Sci. U.S.A.* 86:5673-5677, Aug. 1989.
Ohta et al., "Enzyme-Linked Immunosorbent Assay of Influenza Specific IgA Antibody in Nasal Mucus," *Acta Paediatr Jpn.* 33(5):617-622, Oct. 1991.
Østergaard et al., "A novel approach to the automation of clinical chemistry by controlled manipulation of magnetic particles," *Journal of Magnetism and Magnetic Materials* 194:156-162, 1999.
Ozoemena et al., "Comparative Evaluation of Measles Virus Specific TaqMan PCR and Conventional PCR Using Synthetic and Natural RNA Templates," *Journal of Medical Virology* 73:79-84, 2004.
Park et al., "Polymorphisms of p53, p21 and IRF-1 and cervical cancer susceptibility in Korean women," *Proceedings of the American Association of Cancer Research 44*, Second Edition, p. 1081, Jul. 2003.
Pfyffer et al., "Diagnostic Performance of Amplified Mycobacterium tuberculosis Direct Test with Cerebrospinal Fluid, Other Nonrespiratory, and Respiratory Specimens," *Journal of Clinical Microbiology* 34(4):834-841, Apr. 1996.
Pinder et al., "Immunoglobulin G Antibodies to Merozoite Surface Antigens Are Associated with Recovery from Choroquine-Resistant Plasmodium falciparum in Gambian Children," *Infect. Immun.* 74(5):2887-2893, May 2006.
Pingle et al., "Multiplexed Identification of Blood-Borne Bacterial Pathogens by Use of a Novel 16S rRNA Gene PCR-Ligase Detection Reaction-Capillary Electrophoresis Assay," *J. Clin. Microbiol.* 45(6):1927-1935, Jun. 2007.
Polley et al., "Vaccination for vivax malaria: targeting the invaders," *TRENDS in Parasitology* 20(3):99-102, Mar. 2004.
Porstmann et al., "Comparison of Chromogens for the Determination of Horseradish Peroxidase as a Marker in Enzyme Immunoassay," *J. Clin. Chem. Clin. Biochem.* 19(7):435-439, 1981.
Ranjan et al., "Mapping regions containing binding residues within functional domains of Plasmodium vivax and Plasmodium knowlesi erythrocyte-binding proteins," *PNAS* 96(24):14067-14072, Nov. 1999.
Rida et al., "Long-range transport of magnetic microbeads using simple planar coils placed in a uniform magnetostatic field," *Applied Physics Letters* 83(12):2396-2398, Sep. 2003.
Roosendaal et al., "Comparison of different primer sets for detection of Chlamydia trachomatis by the polymerase chain reaction," *J. Med. Microbiol.* 38:426-433, 1993.
Schachter et al., "Ligase Chain Reaction to Detect Chlamydia trachomatis Infection of the Cervix," *J. Clin. Microbiol.* 32(10):2540-2543, Oct. 1994.
Shi et al., "Fabrication and optimization of the multiplex PCR-based oligonucleotide microarray for detection of Neisseria gonorrhoeae, Chlamydia trachomatis and Ureaplasma urealyticum," *Journal of Microbiological Methods* 62:245-256, 2005.
Shi et al., "Natural Immune Response to the C-Terminal 19-Kilodalton Domain of Plasmodium falciparum Merozoite Surface Protein 1," *Infect. Immun.* 64(7):2716-2723, Jul. 1996.
Shu et al., "Development of Group- and Serotype-Specific One-Step SYBR Green I-Based Real-Time Reverse Transcription-PCR Assay for Dengue Virus," *J. Clin. Microbiol.* 41(6):2408-2416, Jun. 2003.

(56) References Cited

OTHER PUBLICATIONS

Snounou et al., "High sensitivity of detection of human malaria parasites by the use of nested polymerase chain reaction," *Molecular and Biochemical Parasitology* 61:315-320, 1993.
Soukchareun et al., "Use of Na-Fmoc-cysteine(S-thiobutyl) Derivatized Oligodeoxynucleotides for the Preparation of Oligodeoxynucleotide—Peptide Hybrid Molecules," *Bioconjugate Chem.* 9:466-475, 1998.
Staben et al., "Particle transport in Poiseuille flow in narrow channels," *International Journal of Multiphase Flow* 31:529-547, 2005.
Stetsenko et al., "Efficient Conjugation of Peptides to Oligonucleotides by 'Native Ligation'," *J. Org. Chem.* 65:4900-4908, 2000.
Sturm et al., "Vaginal tampons as specimen collection device for the molecular diagnosis of non-ulcerative sexually transmitted infections in antenatal clinic attendees," *International Journal of STD & AIDS* 15:94-98, Feb. 2004.
Tai et al., "Artificial Receptors in Serologic Tests for the Early Diagnosis of Dengue Virus Infection," *Clinical Chemistry* 52(8):1486-1491, 2006.
Tamim et al., "Cervicovaginal coinfections with human papillomavirus and chlamydia trachomatis," *Diagnostic Microbiology and Infectious Disease* 43:277-281, 2002.
TechNote 303, "Lateral Flow Tests," Bangs Laboratories, Inc., Rev. #002, Apr. 11, 2008, pp. 1-7.
Tongren et al., "Target Antigen, Age, and Duration of Antigen Exposure Independently Regulate Immunoglobulin G Subclass Switching in Malaria," *Infect. Immun.* 74(1):257-264, Jan. 2006.
Trenholme et al., "Antibody Reactivity to Linear Epitopes of Plasmodium Falciparum Cytoadherence-linked asexual gene 9 in asymptomatic children and adults from Papua New Guinea," *Am. J. Trop. Med. Hyg.* 72(6):708-713, 2005.
Tung et al., "Preparation and Applications of Peptide—Oligonucleotide Conjugates," *Bioconjugate Chem.* 11(5):605-618, Sep./Oct. 2000.
Tung et al., "Preparation of Oligonucleotide-Peptide Conjugates," *Bioconjugate Chem.* 2:464-465, 1991.
Unger et al., "Monolithic Microfabricated Valves and Pumps by Multilayer Soft Lithography," *Science* 288:113-116, Apr. 2000.
van Gemen et al., "Quantification of HIV-1 RNA in plasma using NASBAä during HIV-1 primary infection," *Journal of Virological Methods* 43:177-188, 1993.
Vinayagamoorthy et al., "Nucleotide Sequence-Based Multitarget Identification," *J. Clin. Microbiol.* 41(7):3284-3292, Jul. 2003.
Vivès et al., "Selective Coupling of a Highly Basic Peptide to an Oligonucleotide," *Tetrahedron Letters* 38(7):1183-1186, 1997.
Walker et al., "Strand displacement amplification—an isothermal, in vitro DNA amplification technique," *Nucleic Acids Research* 20(7):1691-1696, 1992.
Walker, "Empirical Aspects of Strand Displacement Amplification," *PCR Methods and Applications* 3:1-6, 1993.
Wang et al., "Molecular engineering of DNA:molecular beacons," *Angew Chem Int Ed Engl* 48(5):856-870, 2009.
Watson et al., Molecular Biology of the Gene, 4th Ed., Benjamin Cummings Publishing Company, Menlo Park, California, Jan. 1987.
Weinstock et al., "Sexually Transmitted Diseases Among American Youth: Incidence and Prevalence Estimates, 2000," *Perspectives on Sexual and Reproductive Heath* 36(1):6-10, Jan./Feb. 2004.
Whiley et al., "Comparison of three in-house multiplex PCR assays for the detection of Neisseria gonorrhoeae and Chlamydia trachomatis using real-time and conventional detection methodologies," *Pathology* 37(5):364-370, Oct. 2005.
Witkin et al., "Detection of Chlamydia trachomatis by the polymerase chain reaction in the cervices of women with acute salpingitis," *Am J Obstet Gynecol* 168(5):1438-1442, May 1993.
Woehlbier et al., "Analysis of Antibodies Directed against Merozoite Surface Protein 1 of the Human Malaria Parasite Plasmodium falciparum," *Infect. Immun.* 74(2):1313-1322, Feb. 2006.
Wu et al., "The Ligation Amplification Reaction (LAR)—Amplification of Specific DNA Sequences Using Sequential Rounds of Template-Dependent Ligation," *Genomics* 4:560-569, 1989.
Yogi et al., "Clinical Evaluation of the Bladder Tumor Marker "TU-MARK-BTA"," *Hinyokika Kiyo* 37(4):335-339, Apr. 1991.
Khanna et al., "Transformation of *Bacillus subtilis* by DNA Bound on Montmorillonite and Effect of DNase on the Transforming Ability of Bound DNA," *Applied and Environmental Microbiology* 58(6):1930-1939, Jun. 1992.
Cady, "Quantum dot Molecular Beacons for DNA Detection," in Micro and Nano Technologies in Bioanalysis, Lee et al., (eds.), Humana Press, 2009, pp. 367-379.
Cissell et al., "Resonance energy transfer methods of RNA detection," *Analytical and Bioanalytical Chemistry* 393(1):125-135, 2009.
Freund et al., "Film buckling, bulging and peeling," in *Thin film materials—Stress Defect Formation and Surface Evolution*, Cambridge University Press, 2003, pp. 312-386.
Frohman, "Race: Rapid Amplification of cDNA Ends," in *PCR Protocols: A Guide to Methods and Applications*, Innis et al., (eds.), New York, Academic Press, Inc., 1990, pp. 28-38.
Krasnoperov et al., "Luminescent Probes for Ultrasensitive Detection of Nucleic Acids," *Bioconjug. Chem.* 21(2):319-327, Feb. 2010.
Li et al., "Molecular Beacons: an optimal multifunctional biological probe," *Biochemical and Biophysical Research Communications* 373:457-461, 2008.
Van Lintel, "A Piezoelectric Micropump Based on Micromachining of Silicon," *Sensors and Actuators* 15:153-167, 1988.
Huft et al., "Fabrication of High-Quality Microfluidic Solid-Phase Chromatography Columns," *Analytical Chemistry* 85:1797-1802, 2013.

\* cited by examiner

*Fig. 6A*
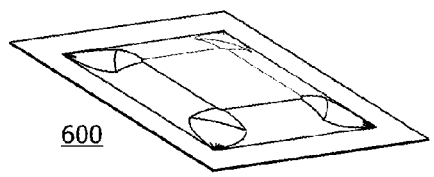
600
*Fig. 6B*
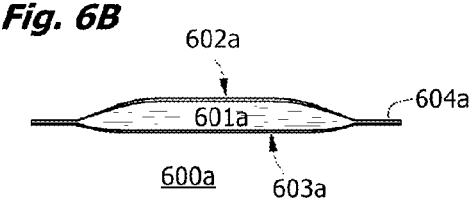
*Fig. 6C*
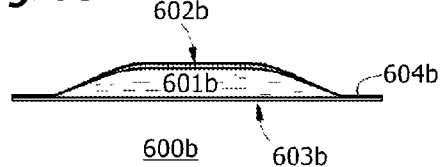
*Fig. 6D*
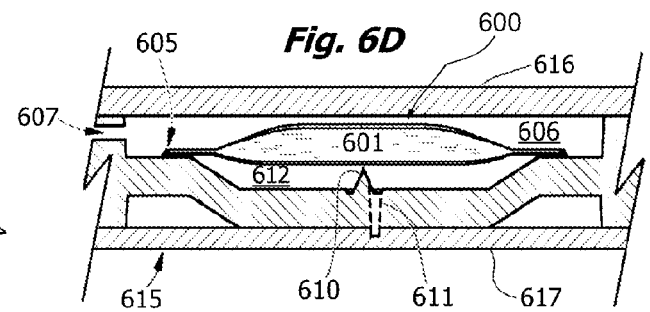
*Fig. 6E*     *Fig. 6F*
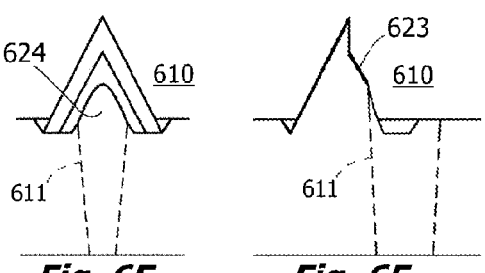
*Fig. 6G*
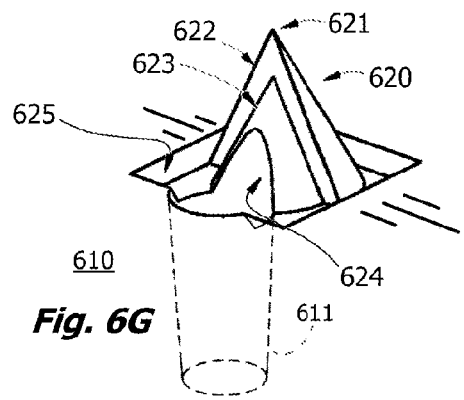
*Fig. 7A*
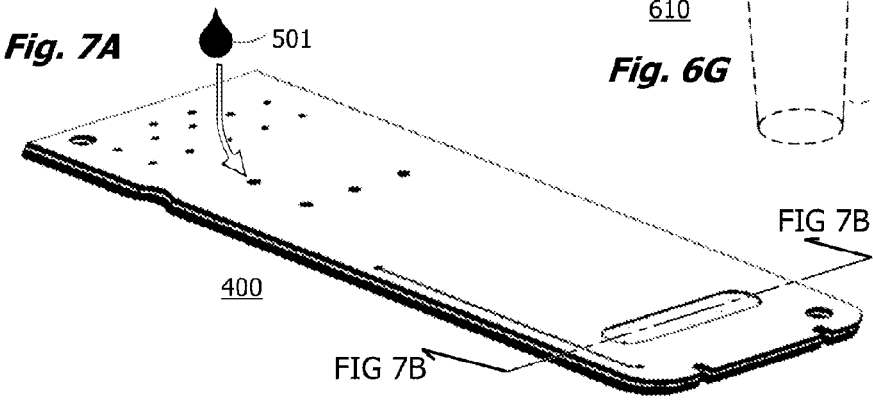
*Fig. 7B*
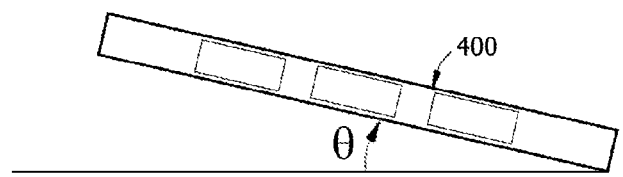

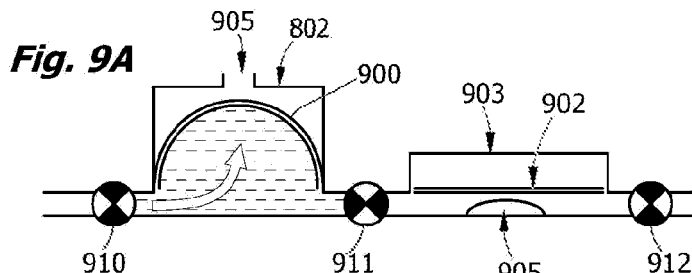
*Fig. 9A*
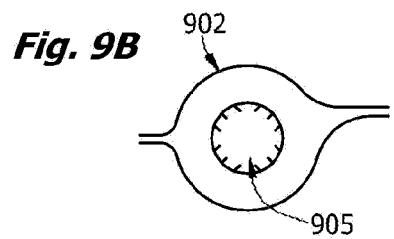
*Fig. 9B*
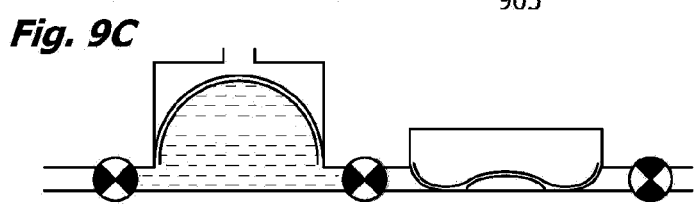
*Fig. 9C*
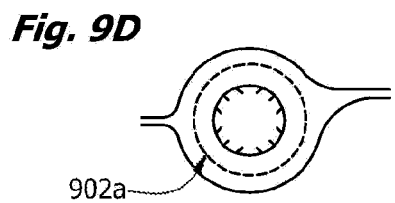
*Fig. 9D*
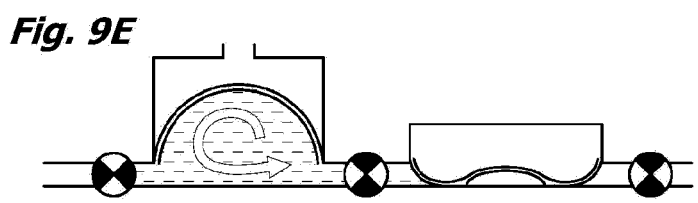
*Fig. 9E*
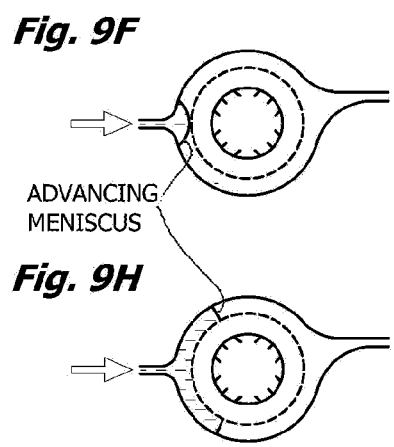
*Fig. 9F*
*Fig. 9H*
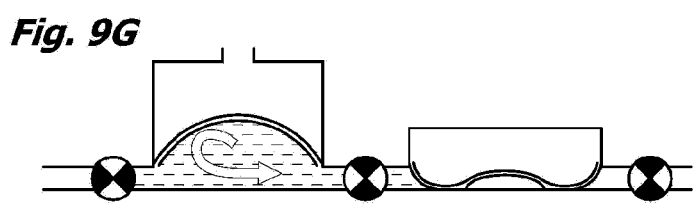
*Fig. 9G*
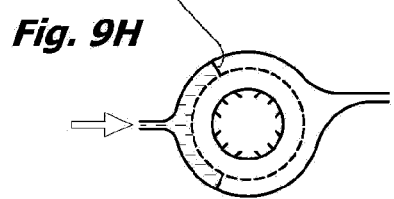
*Fig. 9I*
*Fig. 9J*
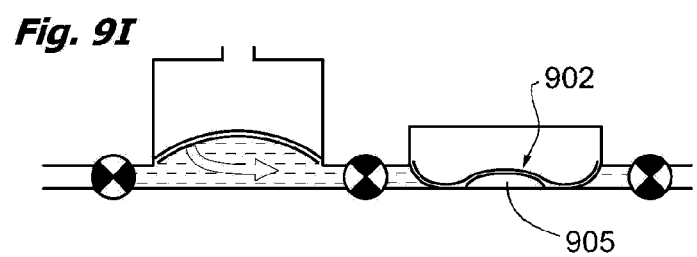
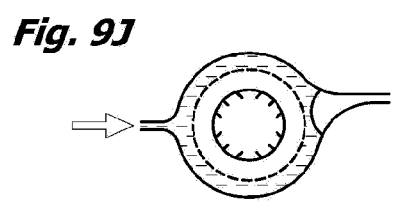
*Fig. 9K*
*Fig. 9L*
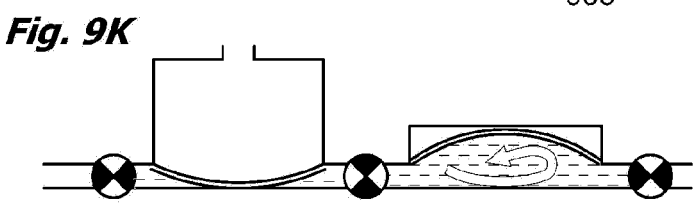
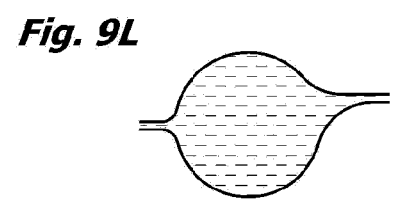

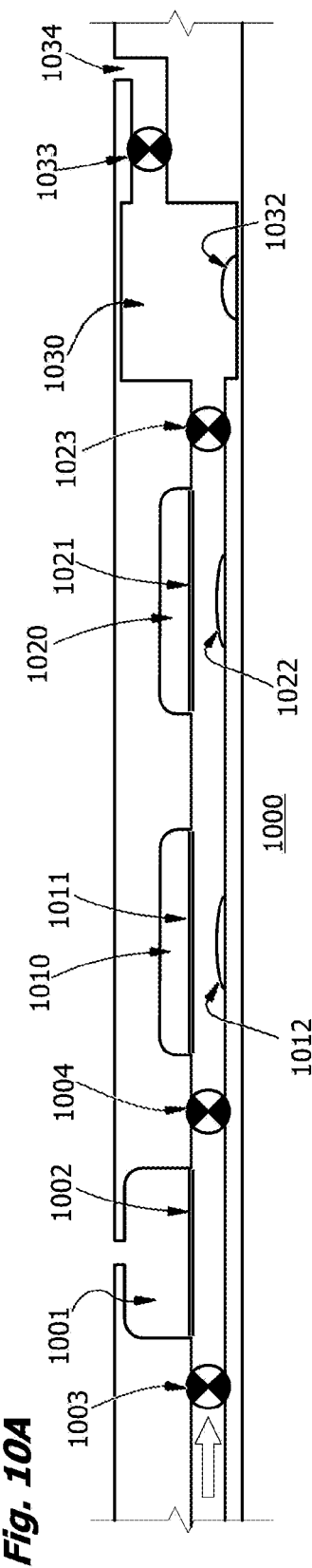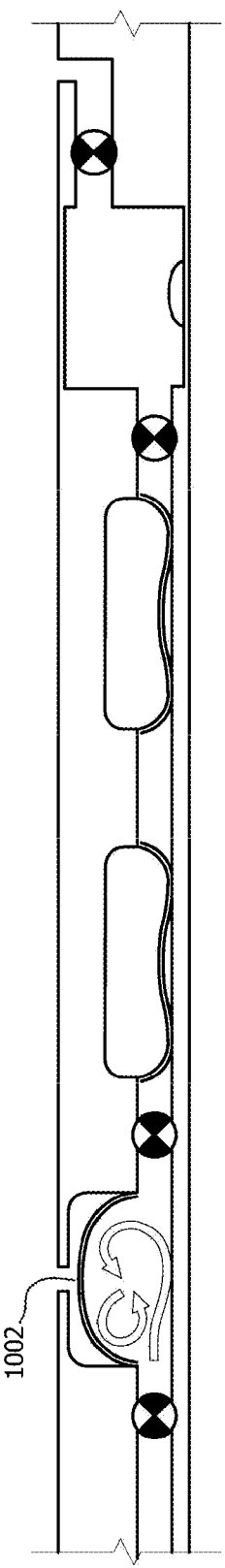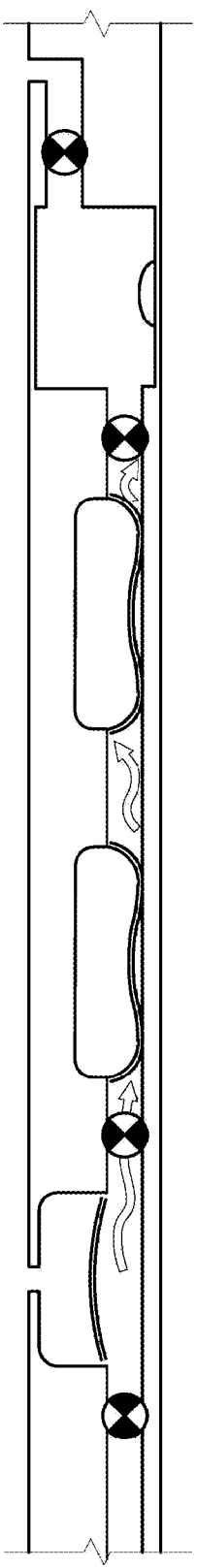

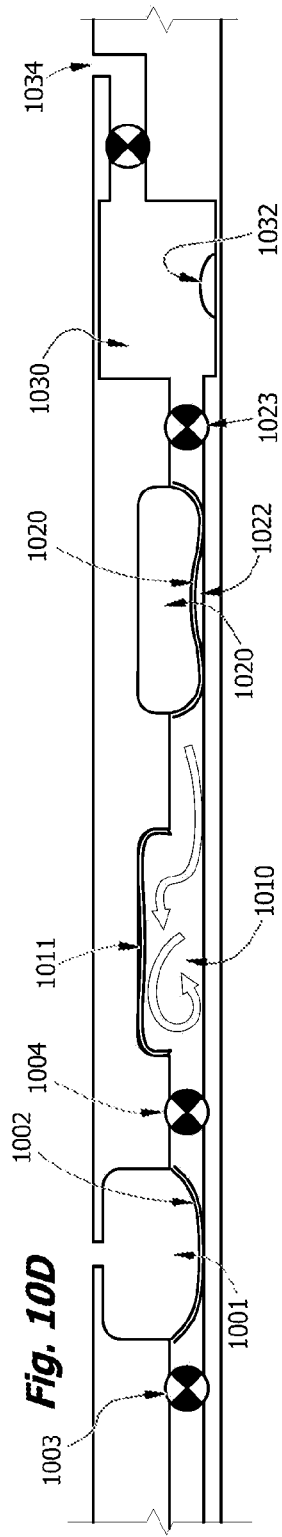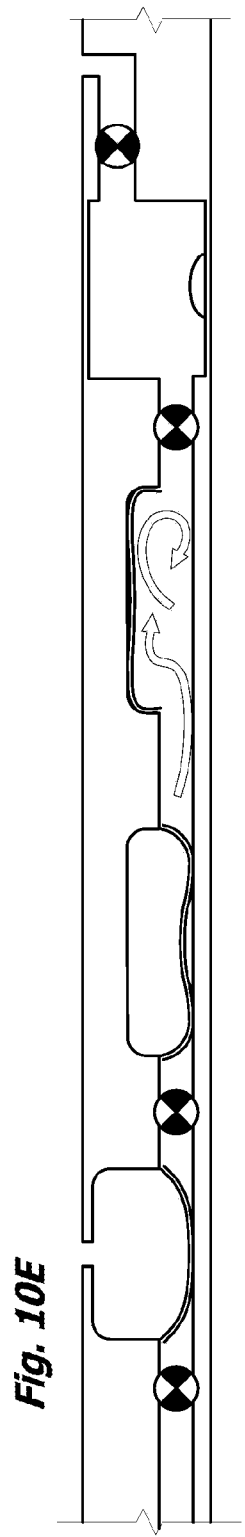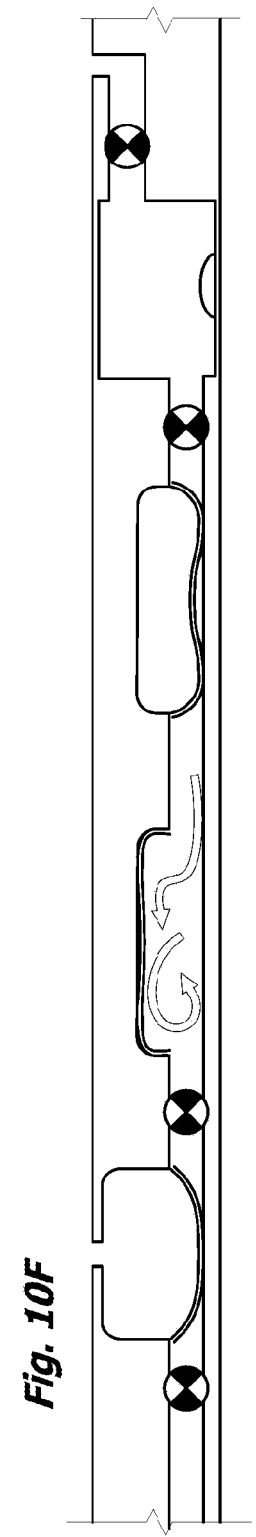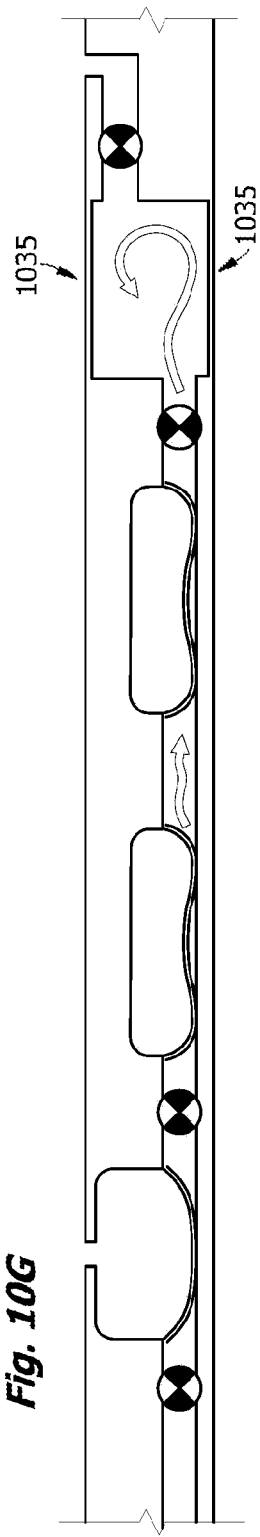

FIRST METHOD FOR PRIMING MICROFLUIDIC CHANNELS AND CHAMBERS WITHOUT BUBBLE ENTRAINMENT

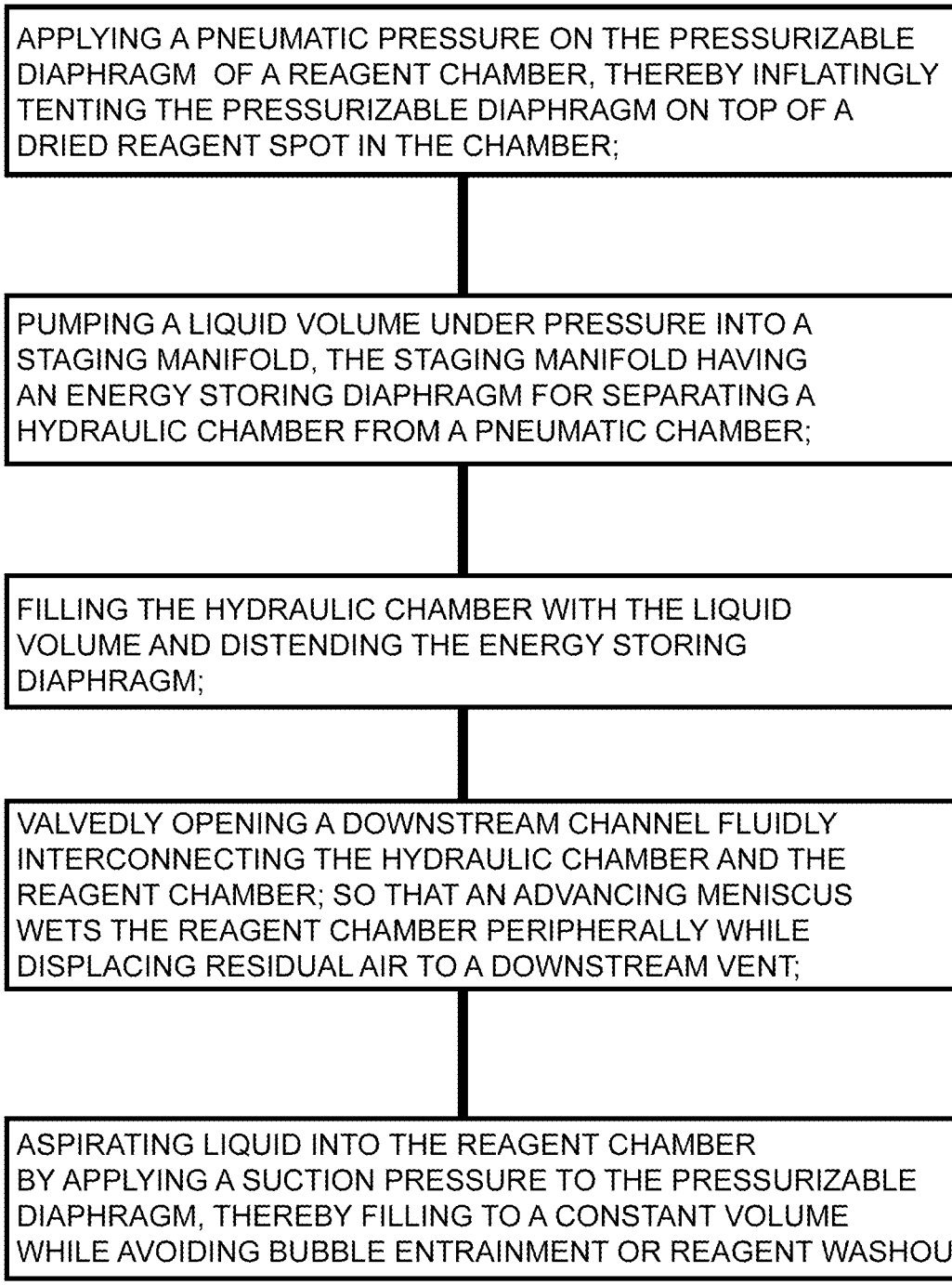

SAMPLE-TO-ANSWER MICROFLUIDIC CARTRIDGE

CROSS-REFERENCE TO RELATED APPLICATION

This application is a Continuation of U.S. patent application Ser. No. 13/575,897, filed Feb. 5, 2013, which is a National Stage Filing of PCT/US2011/022973, filed Jan. 28, 2011, which claims the benefit under 35 USC § 119(e) to U.S. Provisional Patent Application No. 61/299,534 filed Jan. 29, 2010, which application is incorporated herein by reference in its entirety.

BACKGROUND

Field

This disclosure is directed to microfluidic devices and methods for diagnostic, molecular, and biochemical assays and, more particularly, to microfluidic technologies for dispensing and distributing fluid from on-cartridge reagent reservoirs, for pumping, heating and mixing, and for rehydrating dried reagents without bubble entrainment and without reagent washout.

Description of Related Art

Microfluidic devices have found increasing use as tools for diagnostic assays. The devices described by Wilding in U.S. Pat. No. 5,304,487 consisted of "mesoscale" channels and chambers formed on reusable silicon substrates which were infused with fluid reagents from off-cartridge syringe pumps. No consideration was given to on-cartridge fluid and reagent storage and delivery. However, practical commercial applications have lead in the direction of "consumable" cartridges—disposable, single use "sample-to-answer" cartridges that are self-contained for all reagents needed for a particular assay or panel of assays. This is particularly true in the case of molecular biological assay applications, where contamination associated with sample carryover or handling absolutely must be avoided.

On board reagents may include both liquid and dry reagent forms. Both such reagent classes have been subject to certain problems in realization of successful products. Here we address liquid handling issues associated with initial wetout of the channels and chambers of the cartridge and with rehydration of dried reagents. During filling and operation of a cartridge containing microfluidic channels and chambers, particularly those cartridges having a plastic body, liquid wetout is often uneven, such that air pockets are not infrequently entrained in the fluid column by the advancing meniscus against surfaces and in corners. During pumping and mixing of biological samples, foam and bubbles may form that negatively impact the assay performance of the device. Bubbles may arise due to uneven filling of channels or chambers containing dried reagents. Reagent rehydration, wetout and venting are interlinked with the problem of bubble formation. The problem is exacerbated in more complex fluid networks such as described in U.S. Pat. No. 6,068,752 to Dubrow and U.S. Pat. No. 6,086,740 to Kennedy, for example, and in capillary flow-driven devices such as described by Buechler in US Patent Application No. 2005/0136552 or Wyzgol in US Patent Application No. 2004/024051, which have proved notoriously difficult in plastic body devices.

Bubbles may also arise during heating of a sample liquid due to degassing. It is well known that gas solubility is inversely related to temperature and that solutions which are heated readily become supersaturated. Also a source of bubbles by degassing is cavitation, where a fluid is sheared, such as during mechanical or ultrasonic mixing in microfluidic cavities.

Bubbles interfere with optical interrogation of liquids in microfluidic "cuvettes". The path of light may be altered due to a lensing effect created by the curvature of the gas bubble surface and/or due to the gas bubble refracting the light. Bubbles may also interfere with biochemical reactions by altering solute concentrations at bubble interfaces, by denaturing protein structure, and by impacting bulk heating rate and the homogeneity of temperature in a liquid. For example, in the PCR reaction, in which a thermostable polymerase is used to amplify copies of a target nucleic acid, heating and cooling is uneven in the presence of bubbles in the fluid, reducing the efficiency of the process and limiting sensitivity. The presence of bubbles also reduces the volume of fluid in the reaction chambers, and in assays which rely on detecting analyte in volumes of 10-50 uL or less, the presence of a large trapped bubble in a reaction chamber can effectively kill the assay.

In reactions that rely on rate determination, bubbles can drastically interfere with optical determination of slopes and with homogeneous rapid rehydration of dried reagents as is needed to start the reaction with proper availability of substrates. A variety of dried reagents, such as a fluorescent probe, enzyme, buffer or control analyte, may be placed within chambers of a microfluidic device and are needed for proper conduct of the assay. During wetout, entrapment of one or more bubbles may result in incomplete dissolution and mixing of the dry reagent and the sample, thereby impairing the reaction efficiency and reducing the sensitivity of the test.

Lei, in U.S. Pat. No. 6,637,463 proposes varying flow impedance in parallel channels through use of surface tension features and/or cross-sectional area so as to equalize pressure drops, and hence flow, through the multiple flow paths. In one instance, a plurality of exit channels is used to drain fluid from a well so as to avoid formation of recirculating currents or fluid stagnation that would otherwise tend to inefficient washing of fluid and trapping of air bubbles. However, each such feature must be designed by trial and error, and the designs are thus not robust or readily adapted for different assays. Because microscopic variations in dimensions and surface chemistry are difficult to control in microfluidic circuit manufacture, the methods have not been proven a practical solution to the problem of equally dividing flow between parallel subcircuits within a microfluidic card. No description of the use of diaphragms with features for improving wetout was offered.

Ulmanella (US Patent Application No. 2007/0280856) reported efforts to control the meniscus of a fluid filling a microfluidic chamber by physically modifying the bottom surface of the chamber, for example by installing an energy barrier to slow down or stop the leading edge of the meniscus as it crosses the floor of the chamber, or by use of a plurality of grooves or posts on the bottom surface, or by sculpting the depth of the chamber so as to modulate capillary action, or by using a syringe pump, by centrifugation, or by application of a vacuum on the outlet side of the chamber. None of these methods has proved a practical solution to the problem. Capillary action is highly unpredictable and tends to promote formation of air pockets and use of a syringe pump or application of vacuum, as commonly practiced in the prior art, tends to shear the fluid and drive fluid down the path of least resistance, further exacerbating the problem. For example, when two or more microfluidic channels branching from a single inlet are presented to a fluid, such as is useful for splitting a sample or reagent between multiple diagnostic assays pathways in parallel, the fluid may fill the path most readily wetted and leave empty the path having higher fluid resistance. Very tiny differences in resistance between channels lead to preferential wetting of a single channel and no wetting of branching parallel channels, a problem well known to those skilled in the art.

Ulmanella further addresses the effect of dried reagents in wetout of microfluidic chambers and concludes that filling efficiency of chambers containing center-spotted dried reagent was less than 50%, chambers having inlet side spotted reagent were wetted at 65% efficiency, but for chambers having outlet side spotted reagent, the filling efficiency without bubbles increased to 95%. However, positioning of reagent spots with millimeter accuracy during manufacturing is neither a necessary nor a satisfactory means of achieving wetout in the presence of dried reagent spots because it is preferential that the chamber be fully wetted before the reagent is rehydrated so that the concentration of the reagent is not diluted by washout into a downstream channel, as is highly likely if the dry reagent is positioned at the downstream outlet from the chamber!

It is further known that reduction in interfacial and surface tensions in the microfluidic channels or chambers can be achieved, for example, by plasma treatment of the substrate(s) or incorporation of surfactants to decrease hydrophobicity, and by applying a radius to channel intersections. These treatments are also known to improve wettability, but are not effective in eliminating mechanically entrained bubbles and bubbles resulting from thermal degassing, cavitation or stagnation zones. In fact, surfactants can increase the propensity of the gaseous phase to form stable bubbles and foams which can defeat performance of the assay by their persistence. Moreover, the modification of surfaces by processes such as plasma treatment are anticipated to be difficult to control in manufacturing and may be impermanent, degrading progressively during device storage. Therefore it is desirable and is an object of this invention to develop mechanical means and methods for reducing the formation and entrainment of bubbles during initial wetout of assay channels, during rehydration of dry reagents, and for preventing or reducing accumulation and interference of bubbles during operation of the device.

BRIEF SUMMARY

Microfluidic cartridges of the invention, herein termed more generally "devices", are generally formed of a flexible plastic body which houses fluidic channels and chambers patterned and fluidly intercommunicating according to the needs of a diagnostic or biochemical assay to be performed therein. The assay is conducted by reacting a sample with one or more reagents in one or more steps, typically in one or more channels or chambers of the device, for times and at temperatures effective in forming a detectable product that indicates the presence or absence of an analyte in the sample. The cartridges are typically consumables; i.e., they are used once and then discarded; and contain all reagents needed for one or more assays.

To perform an assay, a device of the invention is inserted into a host instrument which relies on optical detection (or other detection means), such as a spectrophotometer or fluorometer for the detection of a chromogen or fluorophore indicative of the presence, absence, and/or amount of any target analytes of interest. In a preferred embodiment, optical windows in the device are interfaced with detection means in the host instrument. However, the presence of one or more gas bubbles in an optical window may impair the detection of the analyte. Bubbles may also interfere with the reactions required to form a detectable product, such as for example an amplicon or other product of a biochemical or molecular reaction, where a bubble may be responsible for uneven heating of a reaction mixture, inadequate mixing, or incomplete or untimely reconstitution of a dry reagent.

In use, a sample fluid is introduced into the inventive device, and the fluidly intercommunicating channels and chambers of the device are then wetted with either a biological liquid sample alone, with liquid reagents, or with a mixture of a sample and one or more liquid reagents. The wettable, fluidly intercommunicating aspects of the device are termed the "hydraulic works" of the device and comprise one or more microfluidic subcircuits having channels and chambers. Control of the hydraulics is effected through pneumatically actuated valves, pumps and diaphragms superimposed as a separate, secondary network or manifold of chambers and channels in the device and supplied by external sources of pressurized air and vacuum. This secondary network is termed the "pneumatic works" of the device. Thus the device is composed of a primary "hydraulic network" for conveying a liquid or liquids and a secondary "pneumatic network" for conveying a gas. The pneumatic network provides a) process control and b) positive and negative pressure for driving the liquid or liquids through the hydraulic network, according to valve and pump logic of a host instrument with which the cartridge is interfaced for performing an assay.

Sample handling and mixing of liquid reagents, including rehydration of any dry reagents disposed within the hydraulic channels and chambers of the device, has been problematic in that bubbles readily become entrained in the fluid during wetting of the hydraulics. This particularly occurs during initial wetout, where bubbles are engulfed by a meniscus advancing rapidly through the device, and subsequently such as by cavitation or degassing associated with mixing and heating. The present invention addresses this problem through one or more fluid handling mechanisms and methods.

Inventive mechanisms, features and methods include pneumohydraulic diaphragms characterized as:

1) an elastic, energy-storing pneumohydraulic diaphragm configured for passively storing a liquid volume under a hydraulic pressure and releasing the liquid volume during wetout of a downstream channel or chamber of the wettable microfluidic subcircuit;

2) a duplexedly layered pneumohydraulic diaphragm having a liquid center for storing and releasing a liquid reagent;

3) a pneumohydraulic diaphragm configured for eliminating headspace from a hydraulic chamber during wetout; or 4) a pair of pneumohydraulic diaphragms comprising a first pneumohydraulic diaphragm interfacing a first hydraulic chamber with valved inlet and a second pneumohydraulic diaphragm interfacing a second hydraulic chamber with valved outlet, and an elevated directly intercommunicating channel between the first and second hydraulic chambers, wherein the pair is configured for reciprocally exchanging fluid through the intercommunicating channel by applying opposing pressure differentials across the first and second pneumohydraulic diaphragms; and where the hydraulic chambers and diaphragms are configured for preventing or reducing bubble entrainment or reagent washout during wetout, fill, pumping or rehydration steps of an assay.

In accordance with various exemplary embodiments, one or more liquid reagents are disposed in sealed reservoirs on the device as manufactured. Dry reagents are printed or "spotted" in channels or chambers and are rehydrated at the time of use. The liquid reagents function as buffers, diluents, solvents, eluants, wash reagents, and as rehydrating reagents. In these capacities, the liquids are dispensed as required from their sealed reservoirs into the hydraulics of the device by pneumatic actuation.

In a preferred liquid reagent embodiment, a sealed liquid storage reservoir of the invention is structured as a two-layered diaphragm with a liquid center, the duplex diaphragm sealedly separating the pneumatics works and the hydraulic works of the device. The duplex diaphragm is composed of two impermeable film layers separated by a liquid center and crimped or fused around the edges and sealed in the device so that the diaphragm separates a hydraulic chamber and a pneumatic chamber. The upper layer, which faces the pneumatics works of the device, is formed of a film having a composition for resisting puncture and the lower layer, which faces the hydraulic works of the device, is composed of a film having a composition that is more susceptible to puncture. Pressurizing the pneumatic side of the diaphragm forces the liquid-filled reservoir against a sharp or "barb" disposed in a fluid receiving basin and punctures the lower layer, but not the upper layer. Following rupture, liquid then flows into the hydraulic chamber and from there into the microfluidic wettable channels of the device. By applying pressure on the pneumatic side of the diaphragm, one or more volumes of reagent can be forced under pressure into the hydraulic works, and by reversing pressure, the fluid can be cause to reflux.

In this aspect, an inventive assay cartridge is characterized as having therein:
a) a duplexedly layered diaphragm sealedly separating a pneumatic chamber of a pneumatic works and a hydraulic chamber of a hydraulic works, the duplexedly layered diaphragm having a first side facing the pneumatic works and a second side facing the hydraulic works, a first layer forming the first side thereof, and a second layer forming the second side thereof, the first and second layers enclosing therebetween a liquid volume as a liquid center;
b) a fluid outlet for receiving and conveying the liquid volume to the downstream microfluidic subcircuit; and
c) a sharp or "barb" disposed in the hydraulic chamber, the sharp for selectively rupturing the second layer and for releasing the liquid volume into the hydraulic works when the duplexedly layered diaphragm is piercingly urged into contact with sharp by application of a pressure differential across the diaphragm.

Surprisingly, the liquid may be released from the on-board reagent reservoir in a series of smaller liquid volumes by the action of serial pulses of pneumatic pressure applied to the first layer of the diaphragm, which remains intact.

Optionally the first layer of the duplexedly layered diaphragm is a rupture-resistant layer and the second layer is a rupture-sensitive layer. The liquid center may contain a liquid reactant, a buffer, a rehydrating fluid, a solvent, or a diluent. On-board storage of liquid is useful for, for example, rehydrating a dry reagent disposed in a downstream chamber or channel, for rinsing a solid phase, for eluting a target analyte or analytes from a solid phase substrate, for making a dilution, for making a chromatographic separation, for actuating or stopping a reaction, or for detecting the target analyte or analytes, and minimizes the possibility of carryover contamination. Optionally the liquid volume is degassed and the duplexedly layered diaphragm is gas impervious. Advantageously, any entrained bubbles are likely to be resorbed in degassed liquids, and degassed liquids are not susceptible to degassing on heating, such as is useful for thermocycling in PCR.

While the devices are generally planar, they may be mounted in the host instrument in a canted position (i.e. angularly with respect to a ground plane), typically at about 15 degrees from flat and are vented at a downstream aspect of each microfluidic subcircuit. As a liquid sample or reagent is introduced upstream into the hydraulic subcircuitry, air is displaced downstream and is vented. The liquid sample and reagents progressively fill and move through the device. By canting the card at an angle of 10 to 35 degrees, air in the device during priming (termed here "wetout") is found to be more readily displaced from the hydraulic works. By careful management of the advancing meniscus during initial fill of the canted card, the problem of bubble entrainment, particularly during fill, is substantially reduced or prevented.

Thus optionally, the hydraulic works may be configured for operation when mounted at an angle of 10-35 degrees relative to the ground plane on a tilted stage of a host instrument and at least one hydraulic chamber is configured with an outlet and intercommunicating channel positioned superiorly relative to that chamber for venting a gas or discharging a bubble from the chamber.

In another aspect of the invention, entrainment of bubbles during wetout is limited by a filling mechanism that involves passive relaxation of an elastically stretched or distended pneumohydraulic diaphragm. This passive mechanism was found to be superior to fill by capillarity and to fill by positive displacement pump action or vacuum. A liquid is first forced under pressure into a specially designed manifold having a "pneumatic chamber" stacked on top of a "hydraulic chamber", where the two chambers are separated by an elastic diaphragm stretched over the roof of the hydraulic chamber. Optionally, liquid may instead be aspirated into the lower chamber, but advantageously, the upper pneumatic chamber is vented and open to atmospheric pressure. The position of the two chambers, while termed "upper" and "lower" or "top" and "bottom" chambers for purposes of explanation, is relative, and is not limiting on the operation of the device. As a liquid volume enters the liquid-receiving chamber, the diaphragm is stretched to hold the volume and resiliently stores the energy of deformation, a form of potential energy having a returning force and a spring constant. Diaphragm material and deformation conditions are chosen so that the "elastic limit" of the material is not exceeded. Then by opening a valve to a downstream channel or channels, the distendedly stretched diaphragm returns to its relaxed state and fluid gently fills the downstream fluid structures without entrainment of bubbles in the advancing meniscus.

This mechanism and method has proved startlingly advantageous where flow is split into multiple channels. By providing an upstream staging manifold with multiple liquid-receiving chambers having elastic diaphragms, each with separately valved outlets that are opened in synchrony, the hydraulic pressure for initiating and sustaining liquid flow into multiple downstream fluidic subcircuits in parallel is segregated or "quantized" so that the flow into all channels is essentially equal and sufficient. Total pressure and volume per downstream channel can be precisely calibrated by selection of the spring constant and the deformation of the elastic diaphragm member so that the restoring flow of liquid into the downstream channel is the volume required to fill the downstream channel to a desired mark; the displaced volume delivered by each diaphragm of the staging manifold is neither insufficient nor in excess for the fluidic operation of splitting flow equally among multiple parallel channels or subcircuits, a necessary fluidic operation in devices intended for multiple assays in parallel. This is a technological advance in the art. Any air downstream is readily displaced by the advancing meniscus and is conveyed to a downstream vent by this means.

In this aspect, an inventive assay cartridge includes:

a) a staging manifold having a plurality of chambers, wherein each chamber of the plurality of chambers is separated into a hydraulic chamber and a pneumatic chamber by an elastic, energy-storing pneumohydraulic diaphragm sealedly mounted therebetween, such that a liquid volume admitted through an inlet into each hydraulic chamber in series or in parallel distends each energy-storing pneumohydraulic diaphragm according to an isobaric pressure proportionate throughout said staging manifold to the displacement volume thereof;

b) the inlet is valvedly closeable for equilibrating the hydraulic pressure throughout the staging manifold after filling is complete; and, c) a plurality of vented downstream channels in parallel, wherein one the channel of the plurality of channels is in fluidic communication with each hydraulic chamber of the staging manifold, each vented downstream channel having a valve for closing during filling and pressurization and for opening during draining and depressurization, whereby the hydraulic pressure of the elastic, pneumohydraulic diaphragm in a distended state is passively converted to the work of advancing a meniscus during initial wetout of the plurality of vented downstream channels equally in parallel.

More generally, wetout or 'priming' is improved by harnessing the mechanical properties an elastic, pneumohydraulic diaphragm in a fluidly distended state to do the work of advancing a meniscus through a wettable downstream microfluidic circuit fluidly connected thereto and thereby displacing any gas therein to a downstream vent without bubble entrainment. This principle is particularly advantageous in equally splitting a fluid into a plurality of downstream microfluidic subcircuits in parallel. In this way, multiple assays may be conducted in parallel and a single sample may be split equally for parallel assays having separate downstream detection means. Surprisingly, the mechanical properties of the elastic diaphragm can be calibrated to fill one or more downstream microfluidic subcircuits to a mark, as is useful in reconstituting a defined mass of a dried reagent in a defined volume, for example.

Microfluidic devices may typically also include at least one dried reagent disposed within the downstream hydraulic network. These reagents are typically spotted or printed during manufacture. During an assay, the dried reagents are rehydrated by sample or by contact with a liquid reagent dispensed as described above. Serendipitously, we have found that the passive liquid wetting mechanism and method described here is advantageously suited to the rehydration of dry reagents without entrainment of bubbles, another technological advance in the art.

In a related embodiment, we have found that by providing pneumatically actuated diaphragms in downstream chambers where dried reagents are spotted, the diaphragms overlying those reagent spots can be pressurized so as to a) temporarily seal the reagent zone (typically central to and on the floor of the chamber) from contact with bulk fluid during the chamber wetting process and b) remove or expel essentially all of the headspace above the dried reagent. When deformed so as to fill the hydraulic chamber, the diaphragm is not fully sealed around the periphery of the chamber. Liquid entering the chamber around the diaphragm is shunted around the lower edges of the chamber and readily displaces any residual air, which is vented from the hydraulics during filling. By relaxing or by reversing the pressure differential across the diaphragm, additional fluid is readily aspirated into the chamber without the formation or entrapment of gas bubbles. Reagents are rehydrated only after the downstream outlet of the chamber is valvedly closed, thereby reducing reagent losses to washout. The reduced dead volume of the dry reagent chambers is thus turned to advantage. Happily, in this way, dry reagent spots can be precisely reconstituted with a desired volume of rehydrating reagent or sample, ensuring that the biological activity of the reagent is quantitatively correct for the assay conditions, a useful refinement in art.

Thus the invention also may feature at least one microfluidic subcircuit having a downstream reaction chamber with upstream inlet and downstream vent, the downstream reaction chamber containing a dried reagent spot or spots, further characterized in that the pneumohydraulic diaphragm is configured to operate with a first position wherein the diaphragm is distended against the floor of the chamber so as to displace headspace air and form a protective temporary tent around and over the reagent spot or spots during wetout, and a second position wherein the diaphragm is relaxedly positioned or aspirated against the roof of the chamber so as to fill the chamber with the liquid volume and uncover and dissolve the reagent spot at full strength without bubble entrainment or reagent washout. The dried reagent spot may be a buffer, an enzyme, a co-enzyme, a co-factor, a polymerase, a primer, a molecular beacon, a probe, a fluorophore, a dehydrogenase, an oxidase, a reactant, a chromogen, a substrate, an antibody, an antigen, or a control.

Also claimed is a method for wetting a microfluidic cartridge while limiting bubble entrainment therein, which comprises:

a) pumping a liquid volume through an inlet and into a plurality of hydraulic chambers forming a staging manifold of a microfluidic card so that an elastic pneumohydraulic diaphragm overlying the liquid volume in each said hydraulic chamber is stretchedly distended, thereby isobarically pressurizing the liquid volume in the plurality of hydraulic chambers;

b) valvedly opening an outlet from each of the hydraulic chambers of the staging manifold, each outlet with fluidic connection to a vented downstream microfluidic subcircuit; and c) splitting the liquid volume substantially in equal measure into each said wettable downstream microfluidic subcircuit by passive relaxing the distended elastic diaphragm—without bubble entrainment.

Wetting a microfluidic device by passive relaxation of an elastic diaphragm is readily distinguished from wetting by capillary action or by active pumping, and has proven surprisingly advantageous in overcoming difficulties with bubble entrainment as are known in the art.

Also claimed is a method for wetting a microfluidic cartridge which contains dried reagent spots, while limiting bubble entrainment therein, which comprises:

a) pumping a liquid volume through an inlet and into a plurality of hydraulic chambers of a microfluidic card so that an elastic pneumohydraulic diaphragm overlying the liquid volume in each the hydraulic chamber is distended, thereby isobarically pressurizing the liquid volume;

b) pressurizing a second diaphragm in a plurality of downstream reaction chambers, each downstream reaction chamber containing a dried reagent spot, the second diaphragm forming a protective temporary tent for sealing around and over the reagent spot and for displacing headspace air from the downstream reaction chamber;

c) valvedly opening an outlet from each the hydraulic chamber, each the outlet with fluidic connection to one of the plurality of downstream reaction chambers;

d) wetting the downstream reaction chamber around the temporary tent and displacing any residual air from the reaction chamber by allowing the distended elastic pneumohydraulic diaphragm to relax, the liquid volume forming an advancing meniscus;

e) optionally closing a valve downstream from the downstream reaction chamber;

f) lifting the temporary tent and conveying a remaining part of the liquid volume into each reaction chamber, thereby dissolving the reagent spot at full strength without bubble entrainment or reagent washout. The temporary tent is lifted by relaxing or by reversing the pressure differential across the second diaphragm member.

In another method, pairs of chambers with pneumohydraulic diaphragms may be used to aid wetout and reagent dissolution for PCR, and for reciprocally pumping fluid when interconnected in series by a channel. By application of alternating positive and negative pneumatic pulses to a first diaphragm in a first chamber, a second diaphragm in a second chamber is driven in synchrony. The second diaphragm may be an elastic diaphragm that functions in accommodating and elastically storing the pulsed energy of the first diaphragm. Mixing is readily achieved by conveying a liquid volume back and forth between the two chambers. By providing each hydraulic chamber with a thin heat exchange film and suitable contact heating elements, "two-zone" PCR is readily achieved. In an improved device, the intercommunicating channel between the chambers is contoured and elevatedly positioned so that bubbles are gravitationally urged to clear the chambers during initial wetout and pumping, and will trap any additional bubbles that form during heating. The intercommunicating channel is preferably configured and contoured to be operated at a tilt of 10-35 degrees and is positioned on the high side of the paired chambers so as to reduce interference from bubbles. Fluid is cycled between a first chamber at a denaturing temperature of a target nucleic acid and a second at an annealing temperature. The plastic body of the device limits parasitic heat capacitance of the device during PCR. Nucleic acid amplification at rates of 8 seconds or less per thermal cycle is readily achieved.

For PCR, amplification reagents are provided with the device. Typically the first chamber contains a first reagent or reagents and the second chamber contains a second reagent or reagents. Typically the reagents are spotted in a centric or pericentric zone in each chamber. During initial wetout, the diaphragms in the chambers are inflatedly distended to press down on and cover the reagents so as to limit rehydration and any washout that would otherwise occur as the meniscus of the rehydrating fluid or sample dissolves the spotted reagents and carries them downstream with the solvent front. After initial wetout, a suction pressure may be applied to the diaphragm so as to aspirate a fluid into the chamber and dissolve the reagents therein. Alternatively, an upstream chamber may be pressurized so as to hydraulically inflate the downstream chamber and dissolve the reagents. Fluid direction of flow may be reversed one or more times so at to improve mixing and rehydration.

Thus the invention may also include a cartridge for use with a host instrument having thermal interfaces for "two-zone thermocycling" and a pneumatic interface with pneumatic means for driving and controlling a PCR amplification. The device works by reciprocating pneumohydraulic action of paired diaphragms in two interconnected hydraulic chambers so as to cyclically denature and anneal a target nucleic acid, the cartridge advantageously having one or more wettability features of the invention for improving wetout of the chambers with liquid without entrainment of bubbles. The device is also advantageous for dissolving reagents in a fixed volume without washout losses during wetout, ensuring that primers, buffers and other reagents are at a fixed strength when reconstituted.

Thus the various aspects of the invention offer novel utility in operation of microfluidic cartridges for diagnostic and biochemical assays and are found to be advantageous as mechanisms and methods for limitation of the bubble interferences that have been a longstanding source of problems with these devices.

In the following description, certain aspects and embodiments of the invention will become evident. It should be understood that these aspects and embodiments are merely exemplary and explanatory and are not restrictive of the invention. Other features and advantages will become apparent from the detailed description which follows.

BRIEF DESCRIPTION OF THE DRAWINGS

FIGS. 6A-G provide views of a reagent reservoir formed of a bilayered duplex diaphragm with liquid reagent center and a sharp or "barb" for puncturing and releasing the liquid into the hydraulic works of the microfluidic device.

FIGS. 7A and 7B show a microfluidic cartridge canted with a tilt as mounted in a host instrument.

FIGS. 9A-9L schematically depict a passive initial wetout mechanism with staging manifold.

FIGS. 10A-10C depict the operation of a staging manifold whereby reagents are rehydrated in preparation for PCR. The operational sequence is continued in FIGS. 10D-G.

FIGS. 10D-10G illustrate a PCR amplification using dual chambers with reciprocating diaphragm action.

FIG. 13 describes the steps of a method for rehydrating dry reagents without bubble entrainment.

DETAILED DESCRIPTION

Figure 1A:
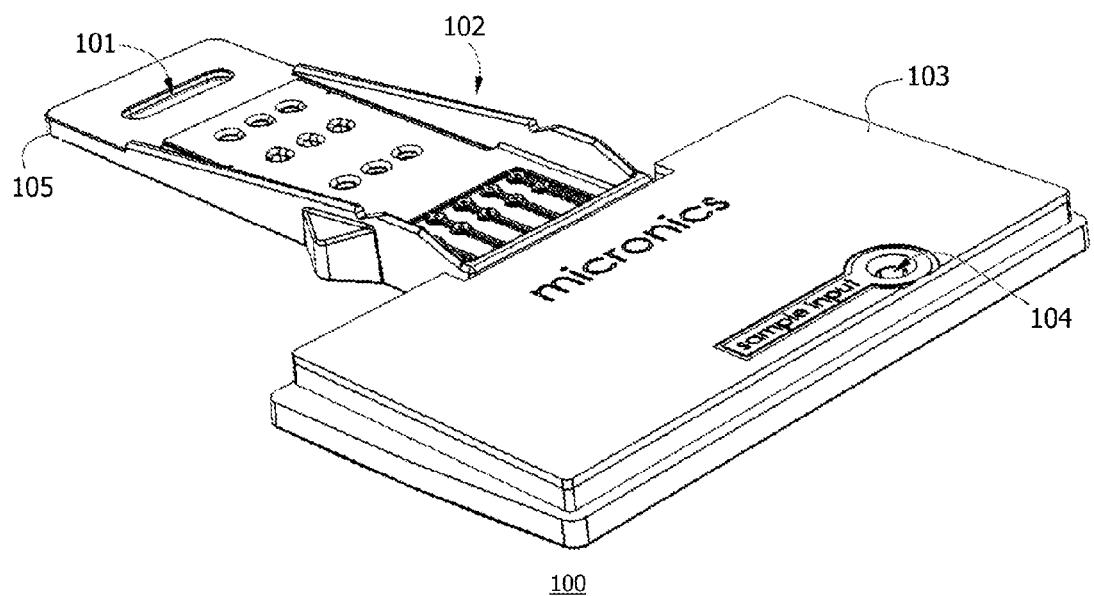
FIGS. 1A and 1B show two perspective views of a disposable, single-use, sample-to-answer microfluidic cartridge of the invention, the cartridge containing all reagents for an assay and requiring only introduction of a biological sample.

Although the following detailed description contains specific details for the purposes of illustration, one of skill in the art will appreciate that many variations and alterations to the following details are within the scope of the claimed invention. The following definitions are set forth as an aid in explaining the invention as claimed.

Definitions

A "cartridge" is an analytical device designed for operation by insertion into a host instrument. The host instrument supplies the pneumatic pressure, pulses, and detection means for performance of the assay. The cartridge contains hydraulic works and pneumatic works, and may include embedded microfluidic "cards" with embedded microfluidic channels and chambers. Sample and reagent liquids are conveyed in a hydraulic network of the cartridge or card; fluid flow is controlled and driven by a pneumatic network that interfaces with the hydraulics at selected junctions, channels and chambers. Typically, the body of the cartridge or card is made of a flexible plastic and may be formed by lamination, molding or a combination thereof. Plastics may include, but are not limited to, polycarbonate, polyethylene terephthalate, cyclic polyolefins, acrylates, methacrylates, polystyrene, graft and block copolymers, and composites thereof. A preferred cartridge is made from rollstock and includes dry reagents printed thereon.

"Hydraulic works" of a device: includes the network or networks of intercommunicating channels and chambers that are intended to be wetted by sample or liquid reagents in the course of an assay. The hydraulic networks are configured with microfluidic subcircuits for performing the steps of an assay.

"Pneumatic works" of a device: includes the network or networks of pneumatically actuated valves, pumps and diaphragms and interconnecting circuitry and manifolds that are useful for powering and controlling the hydraulics of the device. The pneumatic works of the cartridge device interface with positive and negative pressure sources on the host instrument and with valves, diaphragms, pumps and other pneumatically actuated elements that control and drive liquids in the hydraulic network.

"Microfluidic works" of a device: include the hydraulic works formed of a network or networks of internal channels and chambers wetted in the course of the assay and the pneumatic works formed of valve control and pump driving circuits powered by positive and negative pressure sources on the host instrument.

The microfluidic works may be divided into microfluidic subcircuits, where each subcircuit comprises channels and chambers for performing a particular function on a liquid sample or reagent. The microfluidic subcircuits may be organized into serial subcircuits (such as for extraction, amplification and detection of a nucleic acid target or targets) and parallel subcircuits and networks such as for simultaneous assay for multiple targets on a single sample by splitting the sample.

"Top", "bottom", "up", "down", "above", "below", "upward", "downward", "superior to", "floor", "roof", and so forth are indications of relative position and not absolute position, unless reference is made to a specific frame of reference, such as the "ground plane", which is taken as orthogonal to an intersecting plumb line.

"Wetout" ("wet out") refers to the initial hydration of a plastic surface interior to the hydraulic works of a cartridge. Because of interfacial tension effects, initial wetout can involve overcoming a substantial energy barrier and is a major factor in resistance to capillary flow in these devices.

"Target analyte": or "analyte of interest", or "target molecule", may include a nucleic acid, a protein, an antigen, an antibody, a carbohydrate, a cell component, a lipid, a receptor ligand, a small molecule such as a drug, and so forth. Target nucleic acids include genes, portions of genes, regulatory sequences of genes, mRNAs, rRNAs, tRNAs, siRNAs, cDNA and may be single stranded, double stranded or triple stranded. Some nucleic acid targets have polymorphisms, single nucleotide polymorphisms, deletions and alternate splice sequences, such as allelic variants. Multiple target domains may exist in a single molecule, for example an immunogen may include multiple antigenic determinants. An antibody includes variable regions, constant regions, and the Fc region, which is of value in immobilizing antibodies. Target analytes are not generally provided with the cartridge as manufactured, but are contained in the liquid sample to be assayed; in contrast, "control analytes" are typically provided with the cartridge or are routinely present in a sample of a particular type and are assayed in order to ensure proper performance of the assay. Spiked samples may be used in certain quality control testing and for calibration, as is well known in the art.

"Means for Amplifying:" of which the grandfather technique is the polymerase chain reaction (referred to as PCR) which is described in detail in U.S. Pat. Nos. 4,683,195, 4,683,202 and 4,800,159, Ausubel et al. (Current Protocols in Molecular Biology, John Wiley and Sons, Baltimore, Md. 1989), and in Innis et al., ("PCR Protocols", Academic Press, Inc., San Diego Calif., 1990). Polymerase chain reaction methodologies require thermocycling and are well known in the art. Briefly, in PCR, two primer sequences are prepared that are complementary to regions on opposite complementary strands of a target sequence. An excess of deoxynucleoside triphosphates are added to a reaction mixture along with a DNA polymerase, e.g., Taq polymerase. If the target sequence is present in a sample, the primers will bind to the target and the polymerase will cause the primers to be extended along the marker sequence by adding on nucleotides. By raising and lowering the temperature of the reaction mixture, the extended primers will dissociate from the template to form reaction products, excess primers will bind to the template and to the reaction products and the process is repeated. By adding fluorescent intercalating agents, PCR products can be detected in real time.

Other amplification protocols include LAMP (loop-mediated isothermal amplification of DNA) reverse transcription polymerase chain reaction (RT-PCR), ligase chain reaction ("LCR"), transcription-based amplification systems (TAS), including nucleic acid sequence based amplification (NASBA), "Rolling Circle", "RACE" and "one-sided PCR", also termed "asymmetrical PCR" may also be used, having the advantage that the strand complementary to a detectable probe is synthesized in excess.

These various non-PCR amplification protocols have various advantages in diagnostic assays, but PCR remains the workhorse in the molecular biology laboratory and in clinical diagnostics. Embodiments disclosed here for microfluidic PCR should be considered representative and exemplary of a general class of microfluidic devices capable of executing one or various amplification protocols.

Typically, nucleic acid amplification or extension involves mixing one or more target nucleic acids which can have different sequences with a "master mix" containing the reaction components for performing the amplification reaction and subjecting this reaction mixture to temperature conditions that allow for the amplification of the target nucleic acid. The reaction components in the master mix can include a buffer which regulates the pH of the reaction mixture, one or more of the natural nucleotides (corresponding to A, C, G, and T or U—often present in equal concentrations), that provide the energy and nucleosides necessary for the synthesis of nucleic acids, primers or primer pairs that bind to the template in order to facilitate the initiation of nucleic acid synthesis and a polymerase that adds the nucleotides to the complementary nucleic acid strand being synthesized. However, means for amplication also include the use of modified or "non-standard" or "non-natural" bases such as described in U.S. Pat. No. 7,514,212 to Prudent and U.S. Pat. Nos. 7,517,651 and 7,541,147 to Marshall as an aid to detecting a nucleic acid target.

"Means for detection": as used herein, refers to an apparatus for displaying an endpoint, ie. the result of an assay, which may be qualitative or quantitative, and may include a machine equipped with a spectrophotometer, fluorometer, luminometer, photomultiplier tube, photodiode, nephlometer, photon counter, voltmeter, ammeter, pH meter, capacitative sensor, radio-frequency transmitter, magnetoresistometer, or Hall-effect device. Magnifying lenses in the cover plate, optical filters, colored fluids and labelled probes may be used to improve detection and interpretation of assay results. "Labels" or "tags" include, but not limited to, dyes such as chromophores and fluorophores; and chemoluminescence as is known in the prior art. QDots, such as CdSe coated with ZnS, decorated on magnetic beads, or amalgamations of QDots and paramagnetic $Fe_3O_4$ microparticles, are a convenient method of improving the sensitivity of an assay of the present invention. Fluorescence quenching detection endpoints are also anticipated. A variety of substrate and product chromophores associated with enzyme-linked immunoassays are also well known in the art and provide a means for amplifying a detection signal so as to improve the sensitivity of the assay, for example "up-converting" fluorophores.

"Molecular beacon": is a single stranded hairpin-shaped oligonucleotide probe designed to report the presence of specific nucleic acids in a solution. A molecular beacon consists of four components; a stem, hairpin loop, end labelled fluorophore and opposite end-labelled quencher. When the hairpin-like beacon is not bound to a target, the fluorophore and quencher lie close together and fluorescence is suppressed. In the presence of a complementary target nucleotide sequence, the stem of the beacon opens to hybridize to the target. This separates the fluorophore and quencher, allowing the fluorophore to fluoresce. Alternatively, molecular beacons also include fluorophores that emit in the proximity of an end-labelled donor. 'Wavelength-shifting Molecular Beacons' incorporate an additional harvester fluorophore enabling the fluorophore to emit more strongly. Current reviews of molecular beacons include Wang K et al, 2009, Molecular engineering of DNA:molecular beacons. Angew Chem Int Ed Engl, 48(5):856-870; Cissell K A et al, 2009, Resonance energy transfer methods of RNA detection, Anal Bioanal Chem 393(1):125-35 and Li Y, et al, 2008, Molecular Beacons: an optimal multifunctional biological probe, Biochem Biophys Res Comm 373 (4):457-61. Recent advances include Cady N C, 2009, Quantum dot molecular beacons for DNA detection. Methods Mol Biol 554:367-79.

Fluorescence nucleic acid assays include amplification with tagged primers and probe-based detection chemistries. Fluorescent products can be assayed at the end of the assay, or by measuring the amount of amplified product in real time. While not limiting, TaqMan Probe (Applied Biosystems) which relies on displacement and polymerase-mediated hydrolysis of a 5' reporter dye with 3' quencher construct, FRET hybridization probes, dual oligo FRET-based probes (Roche), minor groove binder-conjugated hybridization probes (MGB probes, Applied Biosystems), Eclipse probes, Locked NA Probes (Exiqon/Roche), Amplifluor primer chemistries, Scorpions primer chemistries, LUX primers, Qzyme primers, RT-PCR, among others, are all suitable in the present invention. Fluorescent probes include intercalating probes, such as Syber Green® (Molecular Probes), ethidium bromide, or thiazole orange, FRET probes, TaqMan® probes (Roche Molecular Systems), molecular beacon probes, Black Hole Quencher™ (Biosearch Technologies), MGB-Eclipse® probes (Nanogen), Scorpions™ (DxS Ltd) probes, LUX™ primer-probes (Invitrogen), Sunrise™ probes (Oncor), MGB-Pleiades (Nanogen), and so forth. Recent advances in probe technologies are reviewed by Lukhtanov E A et al, 2007, Novel DNA probes with low background and high hybridization-triggered fluorescence, Nucl Acids Res 35:e30, for example. Reverse transcriptase is used to analyze RNA targets and requires a separate step to form cDNA. Recent advances include Krasnoperov L N et al. [2010. Luminescent probes for ultrasensitive detection of nucleic acids. Bioconjug Chem 2010 Jan. 19 epub].

In addition to chemical dyes, probes include green fluorescent proteins, quantum dots, and nanodots, all of which are fluorescent. Molecules such as nucleic acids and antibodies, and other molecules having affinity for an assay target, may be tagged with a fluorophore to form a probe useful in fluorescent assays of the invention.

"FRET" (Fluorescence Resonance Energy Transfer)—is a fluorescence technique that enables investigation of molecular interactions. It depends on the transfer of energy from one fluorophore to another fluorophore (ie. a donor and a quencher) when the two molecules are in close proximity such a when hybridized. Recent advances include Carmona A K et al, 2009, The use of fluorescence resonance energy transfer (FRET) peptides for measurement of clinically important proteolytic enzymes, Ann Acad Bras Cienc 81(3): 381-92.

Unless the context requires otherwise, throughout the specification and claims which follow, the word "comprise" and variations thereof, such as, "comprises" and "comprising" are to be construed in an open, inclusive sense, that is as "including, but not limited to". Reference throughout this specification to "one embodiment", "an embodiment", "one aspect", or "an aspect" means that a particular feature, structure or characteristic described in connection with the embodiment or aspect may be included one embodiment but not necessarily all embodiments of the invention. Furthermore, the features, structures, or characteristics of the invention disclosed here may be combined in any suitable manner in one or more embodiments. "Conventional" is a term designating that which is known in the prior art to which this invention relates. "About" and "generally" are broadening expressions of inexactitude, describing a condition of being "more or less", "approximately", or "almost" in the sense of "just about", where variation would be insignificant, obvious, or of equivalent utility or function, and further indicating the existence of obvious minor exceptions to a norm, rule or limit.

DESCRIPTION OF THE DRAWINGS

Figure 1B:
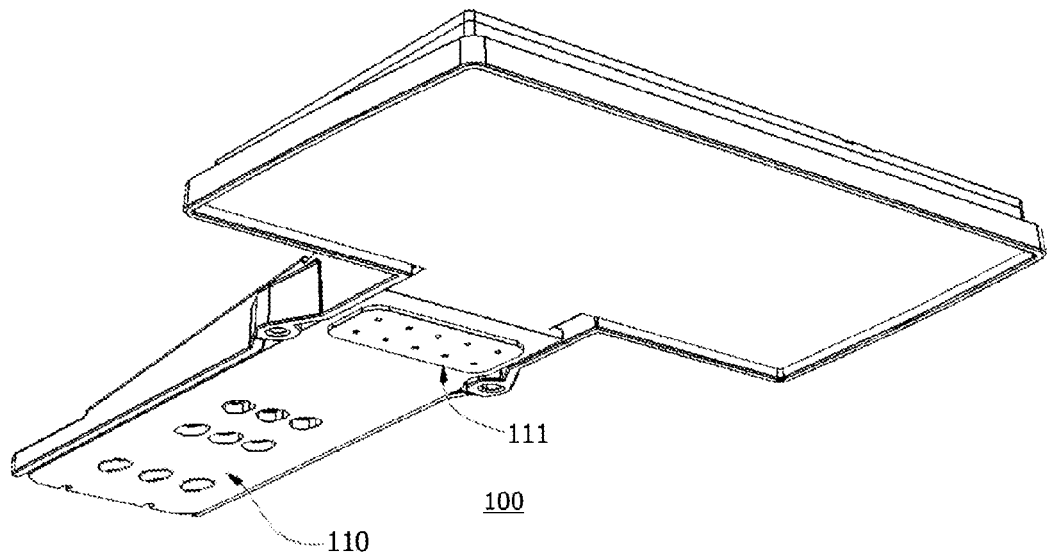
Figure 2:
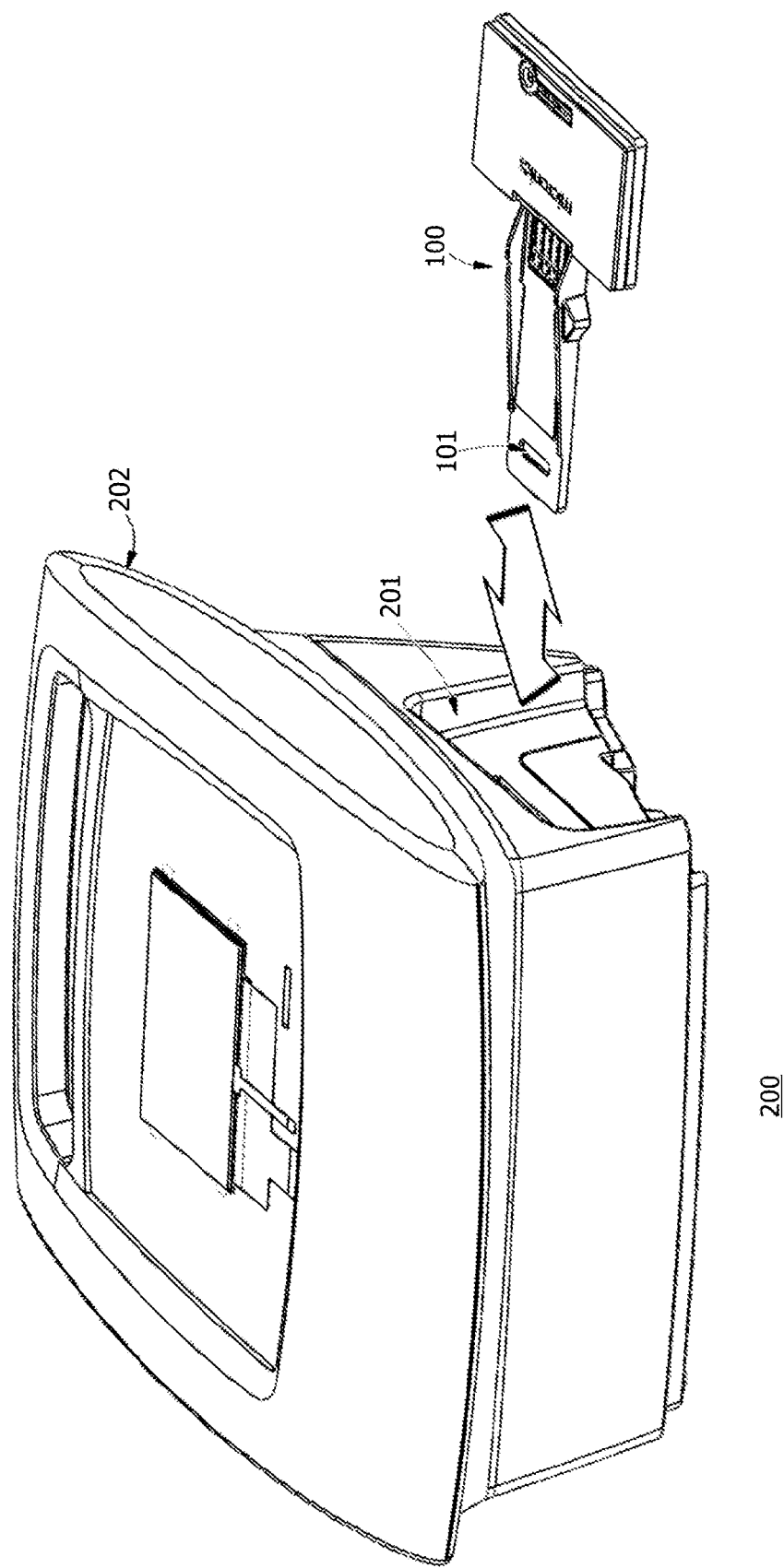
FIG. 2 demonstrates insertion of the assay cartridge in a host instrument for performance of an assay thereon.
Figure 16:
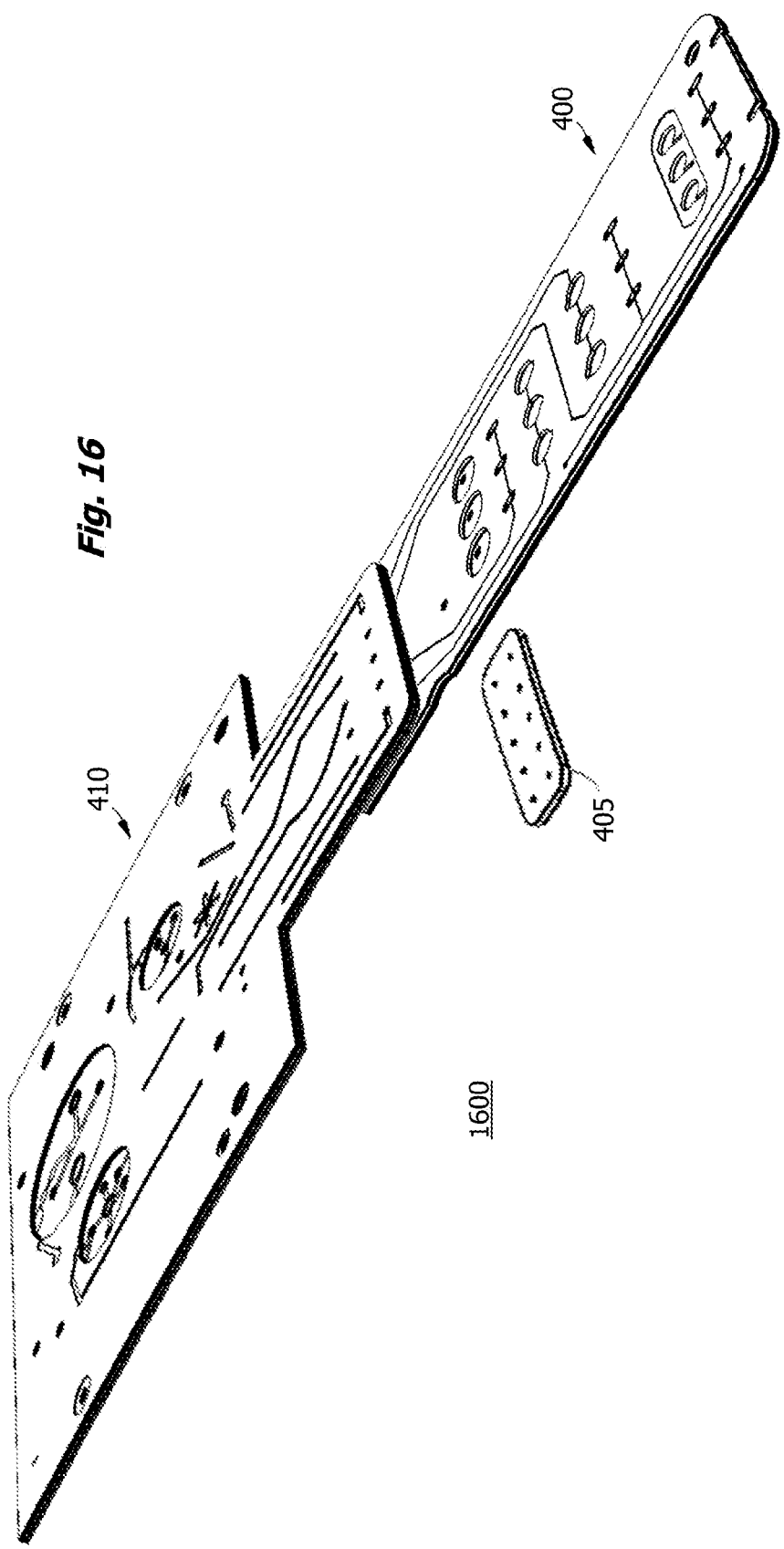
FIG. 16 depicts more detail of a two piece microfluidic card assembly for performing PCR and a pneumatic interface with gasket for interfacing the cards with a compatible host instrument.

Turning to the figures, FIGS. 1A and 1B show two perspective views of a disposable, single-use, sample-to-answer microfluidic cartridge of the invention, the cartridge containing all reagents for an assay and requiring only introduction of a biological sample. In this representative embodiment, the cartridge 100 includes a protective chassis or body 102 with coverplate 103 for convenience in handling. The coverplate includes and contains an inlet port 104 for addition of sample. The projecting nose 105 of the cartridge is inserted into a docking bay of a host instrument (FIG. 2). The projecting nose of the cartridge body includes optical window cutout 101 that aligns with a backside mirror of the docking bay for reflective transillumination and fluorescence detection, while not limited thereto, of a target analyte when inserted into the host instrument. Also on the underside of the cartridge is a thermal interface 110 for heating zones of the microfluidic cartridge and a disposable gasket 111 for sealedly seating the cartridge to a pneumatic control interface of the host instrument in the docking bay. The cartridge body may include microfluidic cards as shown in FIG. 16; however microfluidic works may optionally be integral to the cartridge body.

FIG. 2 demonstrates reversible insertion (double arrow) of the assay cartridge 100 in a docking bay 201 of a host instrument 200. Performance of an assay is controlled with an operator interface generally as shown. Optical window 101 aligns with a detection apparatus inside the chassis 202 of the host instrument.

Figure 3A:
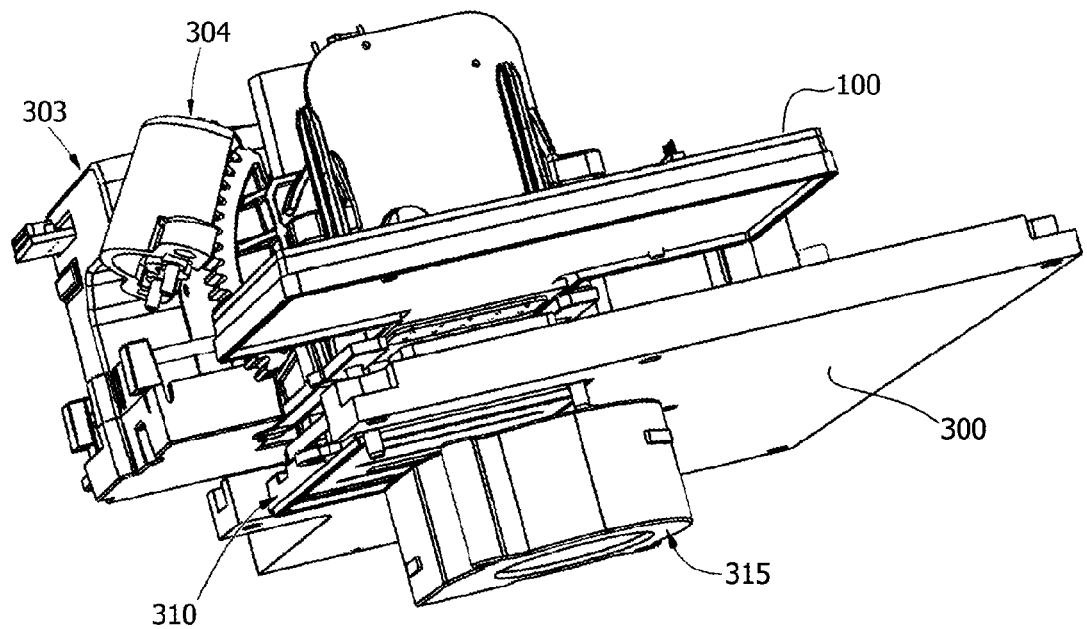
FIG. 3A is a detailed view of the cartridge as inserted in a mechanism of a host instrument. The mechanism includes a heating manifold shown in FIG. 3B and a pneumatic control interface.

FIG. 3A is a detailed view of the cartridge as inserted into a mechanism of a host instrument. An inclined mounting plate 300 is used to angle the mechanism (and the cartridge) at a fixed angle theta (cf. FIG. 7B), which aids in venting air and entrainment of bubbles during initial wetout. The host instrument includes an optics assembly with track-mounted scanning detector head 303 and motorized clamping mechanism 304 for interfacing with optical window 101 of the cartridge. The optics assembly and docking bay are mounted as part of a floating stage that is bolted to the inclined mounting plate but is suspension-mounted so that the cartridge may be clamped against the thermal control module 310 and pneumatics interface ports 330 shown in FIG. 3B. Further description of a host instrument, docking bay, and optics package is provided in copending World Patent Appl. Publ. No. WO 2010/088514, titled "PORTABLE HIGH GAIN FLUORESCENCE DETECTION SYSTEM," which is incorporated herein in full by reference.

Figure 3B:
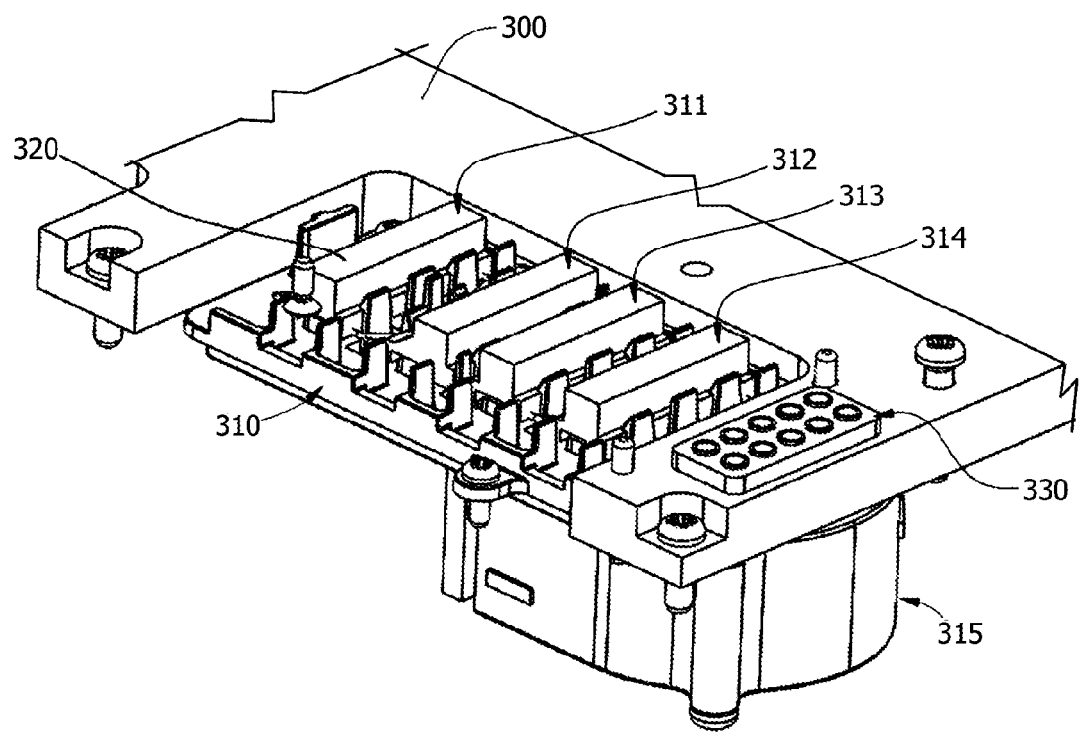

A thermal control module 310 and pneumatic control interface 330 with ten pneumatic ports are shown in more detail in FIG. 3B, which includes a partial view of inclined mounting plate 300. The underside of a cartridge (which is sealed with a thin layer of a heat-conductive polymer as a thermal interface) contacts the upper surfaces of first, second, third and fourth "zone" heating elements (311, 312, 313, 314). A fan 315 is provided for cooling. The top face of the first heating element is provided with a mirror face 320 and operates in conjunction with the optics of host instrument for transillumination and capturing reflected light and/or fluorescent emissions through the optical window 101 of the cartridge when aligned in the docking bay.

Figure 4:
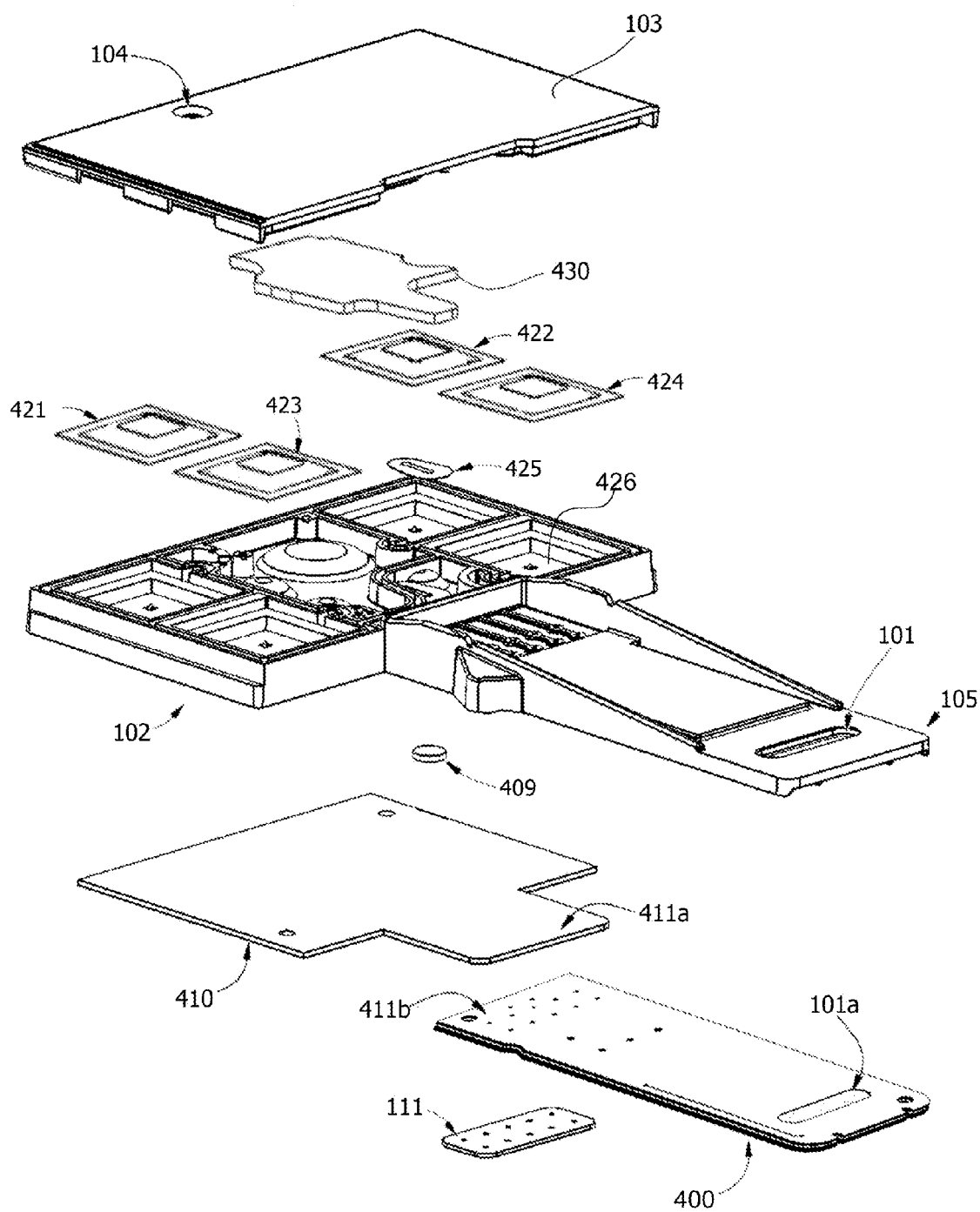
FIG. 4 is an exploded view of disposable microfluidic cartridge with liquid center foil diaphragm packs carrying liquid reagents.

FIG. 4 is an exploded view of a disposable microfluidic cartridge 100 with on-board liquid reagents in frangible liquid reservoirs. Each reagent reservoir is a bilayered duplex diaphragm pack carrying a liquid reagent. The cartridge chassis supports reagent reservoirs (421, 422, 423, 424) in separate wells 426 within the housing. The cartridge as illustrated here is a cartridge designed for PCR and includes four liquid reagents. Optical window cutout 101 on the anterior nose 105 of the cartridge chassis 102 is again shown. Also inside the chassis under the coverplate 103 is an adsorbent pad 430 for sequestering liquid wastes generated in the assay. The cartridge 100 is disposable and is sealed to prevent loss of biohazardous waste. The sample inlet 104 on the coverlid 103 of the device is the sole externally accessible fluid port in the device. All reagents (including any dry reagents and any liquids reagents or rehydrating fluids) are provided within the structure of the device.

On the underside of the cartridge chassis, two "cards" containing microfluidic works are provided, an "outboard card" 410 and an "inboard card" 400. These cards are built up of laminated and/or molded layers and contain hydraulic and pneumatic networks designed for a PCR assay. They are generally flexible and made of plastics such as polyethylene terephthalate and polycarbonate, although not limited thereto. Disk 409 is a glass solid phase adsorbent used in the extraction of nucleic acids from the sample. A seal patch 425 is needed to seal the hydraulic works of the outboard card after installation of the solid phase disk 409.

Figure 5A:
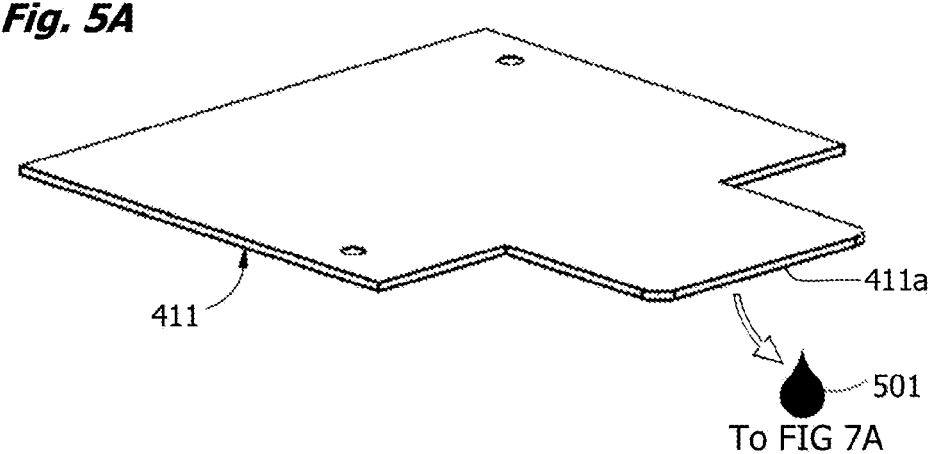
FIG. 5A is a perspective view of a microfluidic circuit for extraction of a nucleic acid target from a biosample.
Figure 5B:
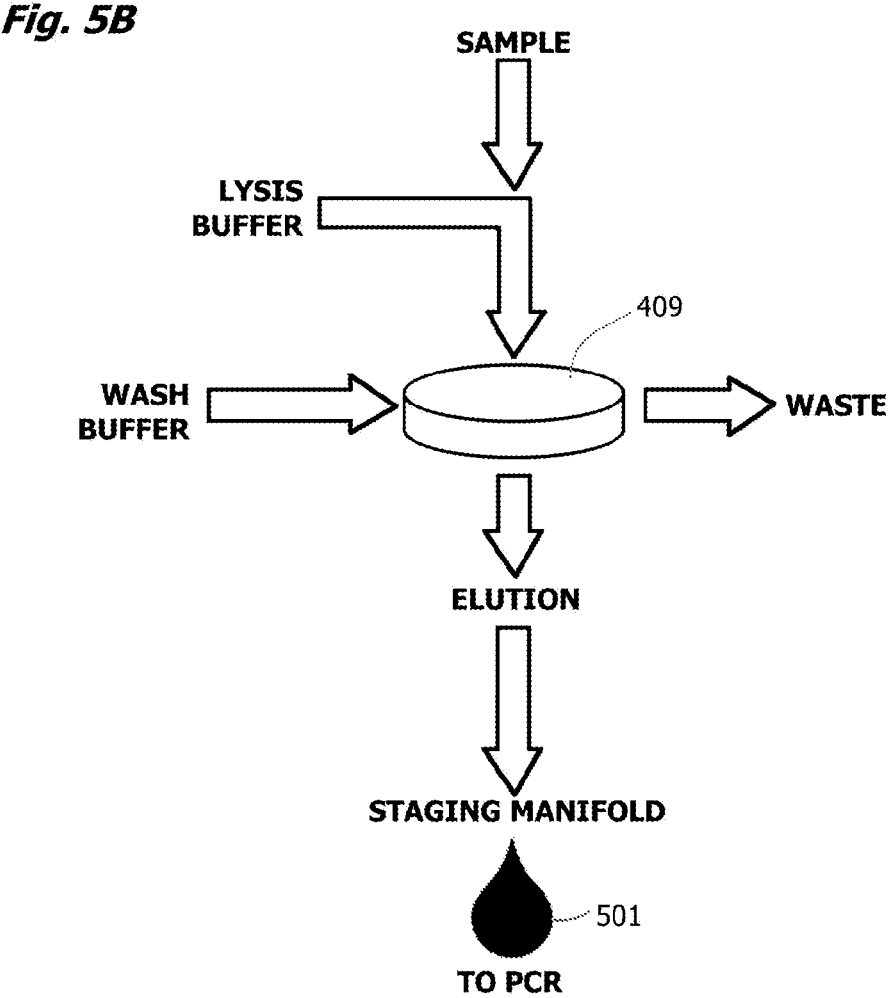
FIG. 5B is a schematic of the extraction process.

The outboard card 410 contains a fluidic circuit that works in conjunction with liquid reagent reservoirs 421, 422, 423, 424 and solid phase adsorbent disk 409 to extract nucleic acids by the protocol outlined in FIG. 5B. The inboard card 400 receives purified nucleic acids via the fluidic interface (overlapping tongues 411a/411b for forming a card junction) between the two cards 400 and 410 and conducts amplification and detection within the hydraulic network of microfluidic channels embedded in the card. The inboard card includes thin surface films that form a detection window 101a sealing the top and bottom of detection chambers enclosed within the card body. These chambers contain less than 50 uL of fluid and are heated by contact with the heating blocks of FIG. 3B. Gasket 111 is provided for sealing the pneumatic control interface to the undersurface of the inboard card at card tongue 411b, which connects to and extends the pneumatic distribution manifold of the host instrument within the microfluidic device.

FIG. 5A is a perspective view of the outboard card 411, which interfaces with the cartridge chassis and liquid reagent reservoirs for extraction of a nucleic acid target from a biosample; FIG. 5B is a schematic of the extraction process. In the extraction process, which is based on the Boom method (U.S. Pat. No. 5,234,809), the sample is first mixed with a lysis buffer, consisting of a mixture of a chaotropic agent and a detergent, and contacted with solid phase adsorbent 409. Following washing with multiple aliquots of wash buffer, which are conveyed to waste, the adsorbed nucleic acids 501 are eluted with a dilute buffer solution and transferred (open arrow, to FIG. 7A) through a fluidically communicating port system under tongue 411a to a staging manifold on the inboard card 400. The liquid contents of this staging manifold are used for nucleic acid amplification as described below. In each step of the extraction, a liquid reagent is required. Each liquid reagent is stored in a bilayer foil diaphragm with a liquid center and the liquid is released under control of a pneumatic actuator that impels the two-layer diaphragm against a sharp, which ruptures (only) the lower layer of the diaphragm and forces the liquid into the hydraulic works of the cards. This process is illustrated in FIGS. 6A-6G.

FIGS. 6A-6G provide various views of a reagent reservoir pouch 600 formed of a bilayered (i.e. two-layered) diaphragm (layers 602, 603) with liquid reagent center 601 and a "sharp" 610 or "barb" disposed below the reservoir, the sharp tip pointing upwards against the lower of the two diaphragm layers 603a/603b, in a sealed internal chamber 615 formed with well 426. The sharp member 610 is shaped for puncturing and releasing the liquid contents into the hydraulic works of the microfluidic cartridge or card.

FIG. 6A illustrates a fluid-filled pouch or reservoir consisting of two diaphragm layers surrounding a liquid center. The two layers are illustrated in a cross-section through the pouch in FIGS. 6B and 6C. Layers 602 and 603 enclose liquid center 601. The two layers are sealed at the edges 604. Foil coated layers of polyester and other plastics were used in forming the diaphragm layers 602, 603. Top layer 602 is generally tough, flexible and resists puncture. Contrastingly, bottom layer 603 is designed to be punctured by sharp 610 and to release its contents into the microfluidic works of the cartridge via reagent outlet channel 611 (FIG. 6D), shown here not to scale. FIG. 6B describes a biconvex reservoir with diaphragm layers 602a and 603a surrounding liquid center 601a with sealed edge 604a, FIG. 6C describes a planoconvex reservoir with diaphragm layers 602b and 603b surrounding liquid center 601b with sealed edge 604b, each having particular advantages in assembly and use.

In FIG. 6D the reagent reservoir is shown mounted as a duplex diaphragm enclosing a liquid center 601 in a reagent chamber 615 of the cartridge housing. Lip seals 605 isolate the pneumatic works 606 from the hydraulic works 612. While not limited thereto, lip seals 605 may be formed by gluing with a UV-actuated adhesive or other sealing method known in the art. When pressurized by air through pneumatic control port 607, the lower surface of the duplex diaphragm assembly (600) is pressed against sharp 610 so that the bottom film layer 603 is ruptured, but not top film layer 602 (FIGS. 6B-6C). In this way, the mechanism becomes a micro-dimensioned pneumatic diaphragm-actuated liquid dispenser. Surprisingly, once the liquid center is pierced, serial pneumatic pulses may be used to force successive microliter volumes of liquid through outlet channel 611 and into the hydraulic works. The reagent outlet channel 611 is in fluidic communication with channels and chambers of the hydraulic network involved in assay reactions dependent on wetting, mixing, eluting and so forth. Plastic cover layers 616 and 617 seal the chamber 615.

FIGS. 6E-6G provide detailed views of the sharp member 610, which is designed so that puncture of lower film layer 602 is not self-sealing around the contour of the sharp. FIG. 6E is a face elevation view; FIG. 6F is a side elevation view, and FIG. 6G is a CAD-generated isometric view. While not limited to the precise form and detailed dimension shown, the sharp is formed as a bisected cone 620 or frustrum of a cone with a barb tip 621, a planar first face 622 that is modified by the molded addition of a protruding convex $2^{nd}$ facet 623 and a recessed concave 3d facet 624, which forms the mouth of outlet channel 611. The delicately molded concavity (concave 3d facet 624) in the projecting tip of the sharp, particularly in combination with the male convexity of the $2^{nd}$ facet 623, confounds the tendency of the film layer to close the rupture in diaphragm 603, thus ensuring operation as what is essentially a pneumatically actuated "spigot" formed for piercing and draining the liquid centered diaphragm. The spigot remains open and fluid flows freely in response to controlled pneumatic pressure applied via port 607. Pan 625 aids in draining the fluid of the reservoir into outlet channel 611.

After extensive experimentation, the piercing action of the sharp was found to be most advantageously effective when the barb tip 621 of the frustrated cone was brought to a radius of from 0.004 to 0.0045 inches, and a preferred radius for this feature as determined to be 0.004 inches (four thousandths of an inch). Sharps outside the range where not found to be as effective by comparison. A microfluidic cartridge of the invention optionally may be characterized as having a sharp for piercing a reagent reservoir where the sharp is a frustrum section of a cone, the cone formed with a tip for selectively piercing a puncture sensitive layer of a duplex diaphragm, the tip having a cutting point with radius of 0.0040 to 0.0045 inches.

The frustrum section of the cone is provided with a planar first facet, a convex second facet formed on the planar first facet, and a concave third facet formed on the concave second facet, the concave third facet forming a mouth of a fluid outlet descending therefrom for draining the released liquid into the hydraulic works.

In a preferred embodiment of the reagent reservoir with liquid center, the first layer of the duplexedly layered diaphragm is rupture resistant and the second layer, proximate to the sharp, is rupture sensitive. The first layer may be a laminated polymer with outer nylon film configured to be puncture resistant and the second layer may be a laminated polymer with outer polyethylene terephthalate film configured to be puncture susceptible. Suitable polymer layers may also contain a sandwiched metallized layer, and are available for example from Technipaq Inc (Crystal Lake, Ill.), with a laminated polyethylene/metal/polymer backing sandwich trilayer structure. An opposable polyethylene film between the two diaphragm members of the fluid pouch is useful to permit heat sealing. UV-activated glues may be used to form a seal or gasket for assembling the diaphragm in a cartridge housing.

FIGS. 7A and 7B show the inboard microfluidic card 400 canted with a tilt as mounted in a host instrument. The card is inclined at about 15 degrees ($\theta$) on its side as detailed in FIG. 7B, which is a sectional view through three detection chambers enclosed in the card. The tilt of the card is configured so air in the card is buoyantly directed to one or more venting ports during wetout and fill, and any bubbles that do arise are trapped in upstream channels and chambers of the card and are limited in entry into the heated zones and detection chambers of the card. Fluid 501 from the nucleic acid elution operation of FIG. 5B enters the inboard card as shown and is routed into a network of microfluidic channels and chambers described in the following figure. A tilt of 10 to 35 degrees has been found to be useful in reducing interference by bubble entrainment and may be implemented for automated assay systems by configuring the host instrument to accommodate a canted stage whereupon a microfluidic card or cartridge is supported during the assay. A vibration assist may also be provided to further isolate bubbles from critical paths. These features also aid in removing air during initial wetout, thus reducing the overall air available for bubble formation.

Figure 8A:
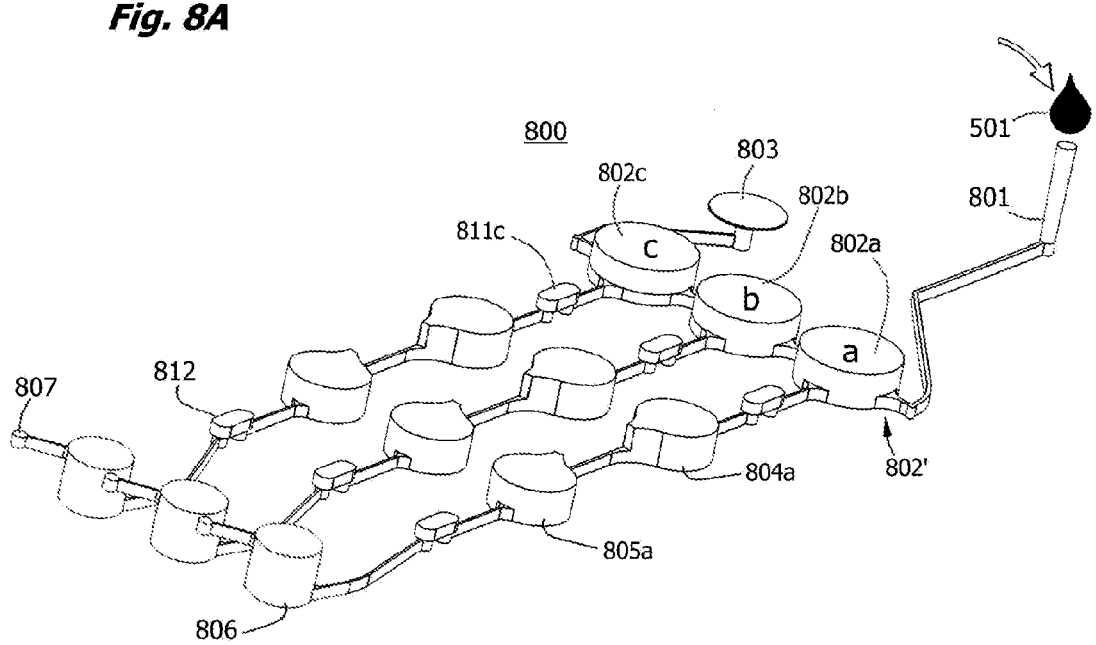
FIGS. 8A and 8B show a worms-eye view of a network of channels and chambers for performing PCR on a microfluidic cartridge; the positions of dry reagents are also marked.
Figure 8B:
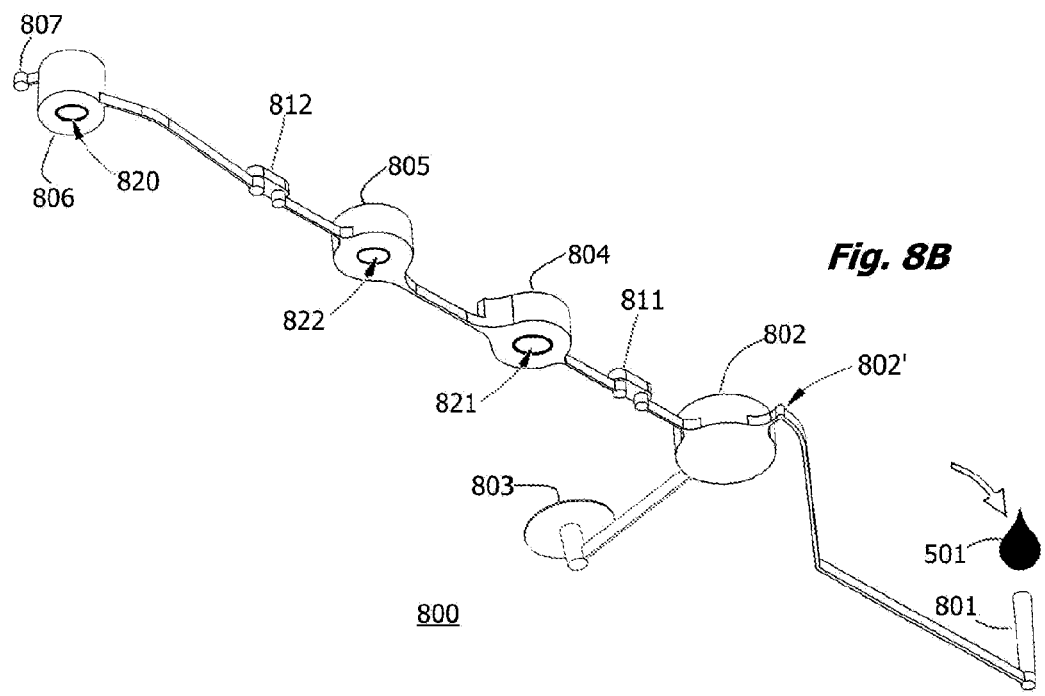

FIGS. 8A and 8B show a "worms-eye" view of a network 800 of channels and chambers for performing PCR as within a microfluidic card 400. The illustration depicts the appearance of the internal wettable surfaces forming a microfluidic subcircuit, but depth of the channels and chambers is exaggerated for clarity. As shown in FIG. 8A, where three channels a, b and c are depicted, eluate 501 (containing any nucleic acids of a sample) is ported into the card through via 801 and enters a three-chambered staging manifold 802', the purpose of which is to split the fluid into three downstream channels equally and to gently and evenly urge the fluid into downstream chambers 804 and 805 while avoiding entrainment of bubbles during initial wetout of internal plastic surfaces. Valves 811 are initially closed. The mechanism of FIG. 8B depicts a single channel.

The splitting of a liquid volume 501 between multiple channels initially was found to be problematic because of uneven wetting, but is desirable so that multiple amplifications or assays can be performed in parallel. As reduced to practice, during the first stage of the filling process, liquid 501 enters three chambered manifold 802' under pressure. Each of chambers 802*a*, 802*b*, 802*c* is bisected horizontally by an elastic diaphragm (see FIGS. 9I-9L, 900) that segregates the fluid contents from an interfacing pneumatic chamber (i.e., the vented upper cavity in a stack of two cavities separated by a diaphragm) and passively stretches during fill. During this step, pressure is equalized between the multiple channels. During the fill, air beneath the diaphragms exits through vent 803, which contains as a sanitary feature a gas permeable, liquid impermeable filter membrane that seals when wetted. Continued pressurization inflates the diaphragms in chambers 802, so that when released by opening valves 811 (and all downstream valves thereto), the pressurized liquid flows evenly into the three (or more) parallel channels as urged by a restorative spring force or pressure exerted by the elastic diaphragm 900, which is distended during filling of chambers 802. Because the restorative pressure can be precisely controlled and limited, and is a function of the spring constant of the diaphragm, and because the displacement volume of the elastic diaphragms can be precisely controlled, the extent of wetout or "priming" of the downstream channels can be precisely calibrated in the manner of volumetrically filling a pipet, a clear advance in the art. Elastomeric diaphragms were achieved with polyurethane, polyvinylidene chloride, and/or polyester as diaphragm material. One such material is Saranex™ (Dow Chemical), which is a polyvinylidene chloride extruded sheet sandwiched between polyolefin layers as a composite thin film. Other materials may be used.

Advantageously, the passively stretching diaphragms 900 (FIGS. 9A-9L) of each chamber 802 thus become an energy storing device for distributing fluid into one or more parallel downstream channels without entrainment of bubbles. By knowing the downstream volume, the energy in the stretched diaphragms may be adjusted so that each parallel channel is filled to a mark, as in a volumetric pipet, the fill volume generally falling short of the detection chambers 806 and final valve structure 812 in each branch, but fully wetting chambers 804 and 805. During wetout, all downstream structures are cleared of air ahead of a steadily advancing meniscus via terminal vent 807, which may be operated under sanitary conditions by capping with a hydrophobic liquid impermeable gas-permeable membrane in the manner illustrated for vent 803, if desired. Because the flow of liquid during relaxation of the diaphragms is not forced by pneumatic overpressure, does not depend on capillary flow, and is finite, the advance of the meniscus is progressive and orderly, limiting entrainment of air pockets in its wake. This is a technological advance in the art, permitting precise filling of parallel downstream networks without entrainment of bubbles. The method is facilitated by the tilt of the card and by removing corner radii (as are sometimes associated with localized increases in surface tension that may impede wetting) from junctions of channels and chambers.

In a further refinement of this method, chambers 804 and 805 are also fitted with internal diaphragms. Unlike the passively flexing diaphragm of chamber 802, the pneumatic face of the diaphragms of chambers 804 and 805 are not vented to atmosphere and can be driven by positive pneumatic pressure or negative pneumatic pressure supplied from a pressure manifold, thus serving as pumps. During the fill cycle, the diaphragms are "tented" or "inflated" downward to occupy volume of the lower hydraulic chamber so to as to reduce or eliminate any dead volume of the chambers. Liquid seeping past these diaphragms on the outside bottom edges of the chambers fully wets the chambers and displaces any residual air. Then upon releasing the diaphragms after closing valve 812, liquid is aspirated from upstream to fill and make up the volume of the chamber.

In a further refinement of this method, dry reagents are placed in chambers 804 and 805, the nature of the dry reagents relating to the nature of the assay to be performed. The reagents are generally spotted near the center of the chamber. During initial wetout, the diaphragm is fully tented downward to occupy the volume of the lower hydraulic chamber so as to reduce the dead volume therein and protectively covers and protects the dry reagent spots from dissolution and washout as the chamber residual dead volume is wetted. After valve 812 is closed and the chamber is flooded with liquid by reversing pressure differential across the diaphragm, the reagent dissolves rapidly and at full strength.

The positions of dry reagents are marked in FIG. 8B. As can be seen, dry reagents having specific functions are placed in designated chambers. Dry reagent spot 821 contains for example master mix and primers that are advantageously mixed with and denatured in the presence of target template. This chamber 804 is preferentially heated at a temperature sufficient for the denaturing of template nucleic acid. Chamber 805 contains for example dried polymerase 822 and is at a temperature suitable for annealing of primers and target and for initiation of polymerization. In the detection chamber 806, dry reagent spot 820 contains probes such as, for example, "molecular beacons" or intercalation dyes which are used to detect amplicon produced in the amplification. Detection chamber 806 is bounded at a "top" and a "bottom" by thin film optical windows and is reflectively transilluminated for fluorometric detection of amplified target. Synergically, the bottom thin film layer is also effective in heat transfer from the mirror faced heating element shown in FIG. 3B, with which the card interfaces during the assay, and can thus be termed a "thermo-optical window", such as is useful in assaying by thermal melting curve as will be described below.

Figure 8C:
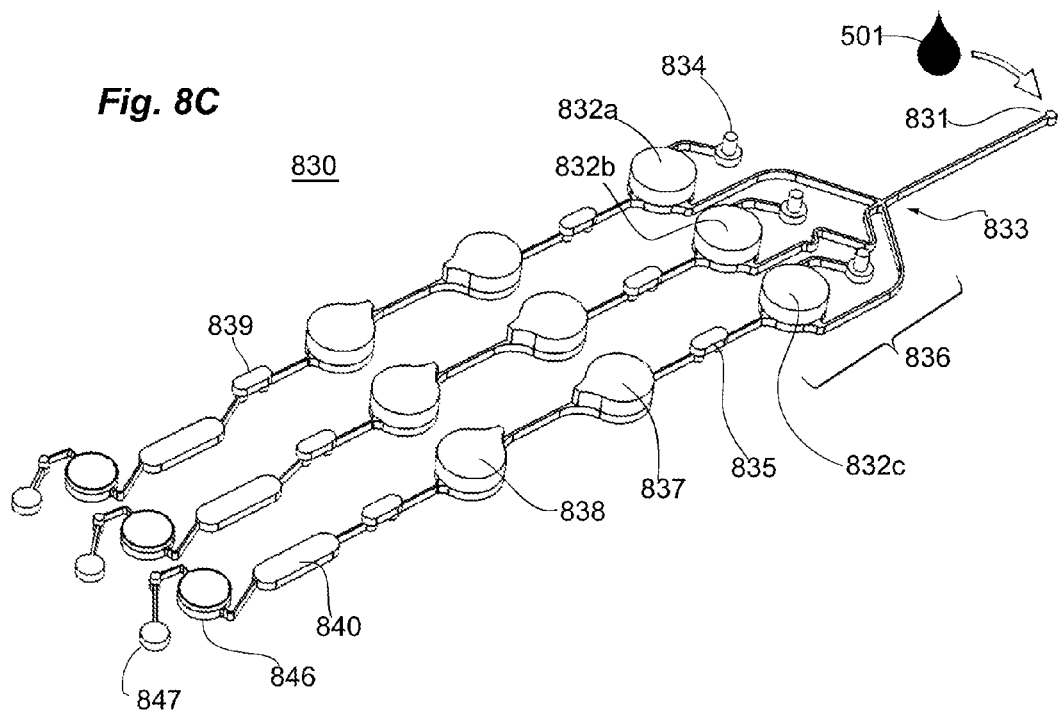
FIGS. 8C and 8D illustrate an alternative cartridge configuration in worm's-eye view.
Figure 8D:
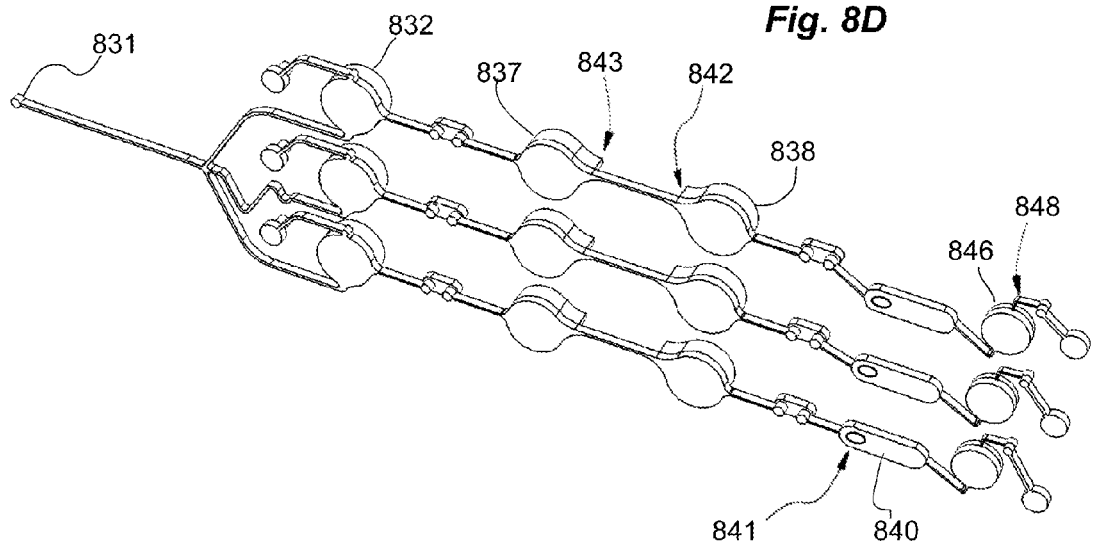

FIGS. 8C and 8D describe an alternative cartridge 830 for PCR. In this cartridge, sample 501 entering the cartridge under pressure at sample inlet 831 is split at trifurcation 833 and fills each of three chambers 832a, 832b, 832c, which are independently vented at hydrophobic vents 834. Each chamber 832 contains an elastic pneumohydraulic diaphragm, which when stretched during fill exerts a pressure on the liquid volume contained in the chamber. The chambers may be filled by injecting a series of pressurized volumes from an upstream pump. Fluid flow into the three branches of the distribution manifold is not necessarily split equally, but volume and pressure in each chamber (832a, 832b, 832c) become isobaric and equalized as the staging manifold equilibrates. During the fill process, downstream valves 835 are closed.

After pressurization of the staging manifold 836 is completed and equilibrated, valves 835 are opened so that the elastic diaphragm of chambers 832 can relax while passively urging the liquid contents into amplification chambers 837 and 838. During this process, the diaphragm elements of chambers 837 and 838 are inflated to occupy the lower hydraulic chamber so that headspace is removed and any dried reagents in the chambers are protected from being washed away by the advancing meniscus. PCR amplification is performed as described for FIGS. 8A and 8B. Downstream valve 839 is opened to convey any amplification products through an antechamber 840 to a detection chamber 846 by pressurizing diaphragms in both chambers 837 and 838 while valve 835 is closed. Any air is flushed out of the system through terminal vent 847. Advantageously, dried probe 841 printed or spotted in the antechamber is dissolved and mixed with amplicon prior to injection into the detection chamber, which improves the transparency of the thermo-optical window bounding the detection chamber and reduces or prevents autofluorescence of certain dyes useful as molecular beacons or FRET probes. By operating the card at a tilt angle θ as described in FIG. 7, air is advantageously purged to a vented port superiorly disposed on the detection chamber.

As can be seen in FIG. 8D, the inlet, outlet, and venting ports of detection chamber 846 and the amplification chambers 837 and 838 are asymmetrically placed. When the cartridge or card is canted on a tilted stage of the host instrument (referencing FIGS. 3A and 7B), communicating ports (842, 843) between the amplification chambers and at the terminal venting port (848) associated with the detection chamber are elevated relative to the chambers themselves and are contoured to overcome any surface tension effects of the geometry. Air in the system is thus preferentially flushed from the system by the advancing liquid during wetout, which fills the lower aspects of the chambers first, and any bubbles generated by heating-associated degassing of the liquid during PCR are preferentially trapped between the amplification chambers so as to not interfere with heat transfer, and do not enter the detection chamber.

In more methodological detail, FIGS. 9A-9L present a simplified chronology and schematic of the steps or stages of passive initial wetout with staging manifold. Cross-sectional and plan views are shown so that the progress of the advancing meniscus may be seen. In the first view, FIG. 9A, the diaphragm 900 in the staging manifold chamber 802 is shown to be upwardly distended, turgid with a liquid reagent entering from the left through open valve 910, and the pneumatic face of the diaphragm is vented at 905 to atmosphere. Downstream chamber 903 is dry, valve 911 is closed. The initial dry state of reagent spot 905 is monitored in plan view in FIG. 9B on the right.

In FIG. 9C, both valves 910 and valve 911 are closed and valve 912 is open for venting. Diaphragm 900 is pressurized and is tented down over reagent spot 905; the footprint of the diaphragm in contact with the base of chamber 903 is illustrated by a dotted line 902a in FIG. 9D.

In FIG. 9E, valve 910 remains closed and valves 911 and 912 are open. As shown in plan view in FIG. 9F, an advancing meniscus begins to enter chamber 903.

In FIG. 9G, liquid continues to wet chamber 903 and fill any dead volume on the periphery of the chamber around the collapsed roof formed by the diaphragm. This process continues as shown by snapshot in FIG. 9I. The progressive deflation of the passively stretched diaphragm 900 in chamber 802 is shown on the left in timelapse snapshots in FIGS. 9G, and 9I. It can be seen in FIG. 9K that pressure applied across diaphragm 902 can be reversed when valves 910 and 912 are closed so that liquid is aspirated from the staging manifold chamber 901 and fills chamber 903, dissolving dried reagent 905. Complete dissolution is shown figuratively in FIG. 9L. During this process, air has been effectively displaced from the wetted areas, first by elimination of deadspace in chamber 903, then by the progressive elimination of residual air by the relaxation of diaphragm 900, and finally by sealing the purged system and aspirating the contents of chamber 802 into chamber 903 to solubilize and to be mixed quantitatively as a reagent solution. The volume of liquid filling downstream chambers can be precisely controlled by configuring a displacement volume of elastic diaphragm 900 and chamber 802; the rate of passive downstream fluid wetout is controlled by selecting a spring constant for the elastic diaphragm 900.

FIGS. 10A-10C demonstrate a further advantageous use of the above inventive mechanism for priming a PCR reaction, where a system having two zones for thermal cycling of the nucleic acid substrate and polymerase is demonstrated. All fluidic systems are contained in a card or cartridge body 1000. Staging manifold chamber 1001 is vented to atmosphere and contains a passive elastic diaphragm 1002 capable of storing a pressurized liquid, which enters from the left through valve 1003. As shown in FIG. 10B, this diaphragm 1002 becomes distended during fluid entry and valve 1003 is then closed. Diaphragms 1011 and 1021 in chambers 1010 and 1020, respectively, are pressurized to form a protective tent over dried reagent spots 1012 and 1022, and to displace deadspace air from the chambers as shown in FIG. 10B. Downstream valves 1023 and 1033 are open at this stage so that displaced air is vented from the system via terminal vent 1034. In FIG. 10C, valve 1004 is opened and liquid enters the two chambers where PCR will occur, first in amounts sufficient for priming the chambers. This sequence is continued in FIGS. 10D through G. Fluid is introduced in an amount sufficient to fill the denaturation hot chamber 1010 but no more; applying a vacuum to diaphragm 1011 aids this process. FIG. 10D shows that the "hot" or "denaturing" chamber 1010 is under vacuum and liquid has been aspirated to fill the chamber. After any dry reagent 1012 is quantitatively dissolved and nucleic acid denaturation is sufficient, the liquid contents of chamber 1010 are transferred to the second chamber 1020 at a temperature suitable for annealing of primers so that polymerase-mediated extension may begin upon dissolution of reagent spot 1022. FIG. 10E shows liquid pumped from the hot chamber to the "annealing" chamber by reversing the pressure differential across the two diaphragms. This process is again reversed in FIG. 10F, demonstrating the reciprocating pumping action of the two diaphragms in forcing the liquid back and forth between the hot zone at 1010 (which is contacted with heating block 313, FIG. 3B) and the annealing zone at 1020 (which is contacted with heating block 312). This reciprocating pneumohydraulic action is the basis of nucleic acid amplification by thermocycling in the apparatus. Finally, the fluid with any amplicons is ejected into the detection chamber as shown in FIG. 10G. The detection chamber as shown here is fitted with a pair of optical windows 1035.

In a more complex configuration, an additional temperature station and associated thermal interface with thermal block 314 (FIG. 3B) is used, for example, for reverse transcriptase mediated synthesis of cDNA prior to a PCR-type amplification process. Thus additional chambers may be useful and the geometry and configuration may be varied, mutatis mutandi, by logical extensions of the teachings of the invention. During wetout, diaphragms in each chamber are used to reduce initial deadspace volume. Subsequently, application of pressure differentials across the diaphragms are used to harness serial diaphragm assemblies and valve elements as pumps and mixing elements for hydraulic movement of fluid volumes through the hydraulic works of the devices. A first embodiment of a reverse-transcriptase device is shown in FIGS. 14A-14C, and will be described in more detail below.

Figure 11:
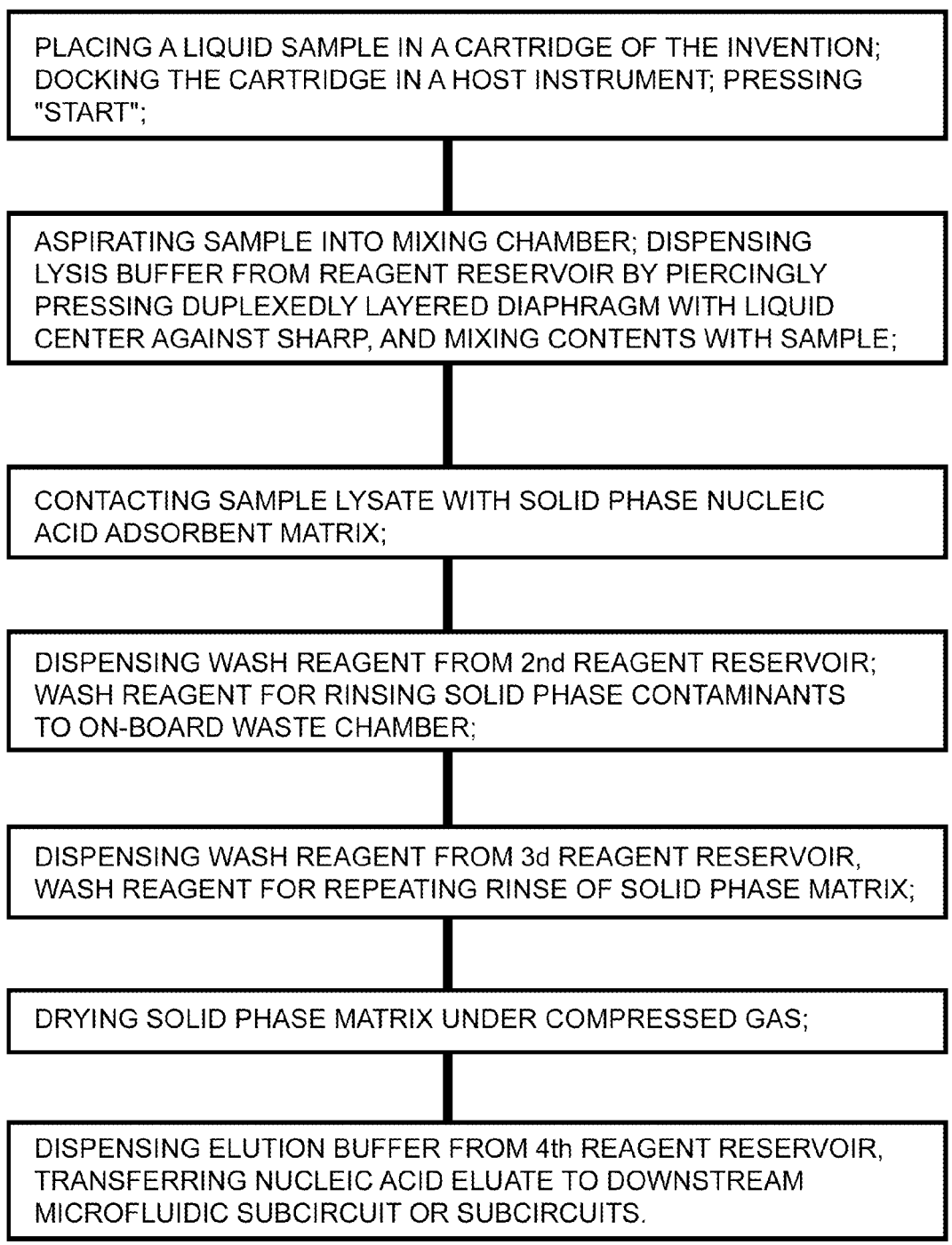
FIG. 11 describes the steps of a method for extracting nucleic acids from a sample, where a bilayered duplex diaphragm with liquid center is used to dispense the reagents.
Figure 12:
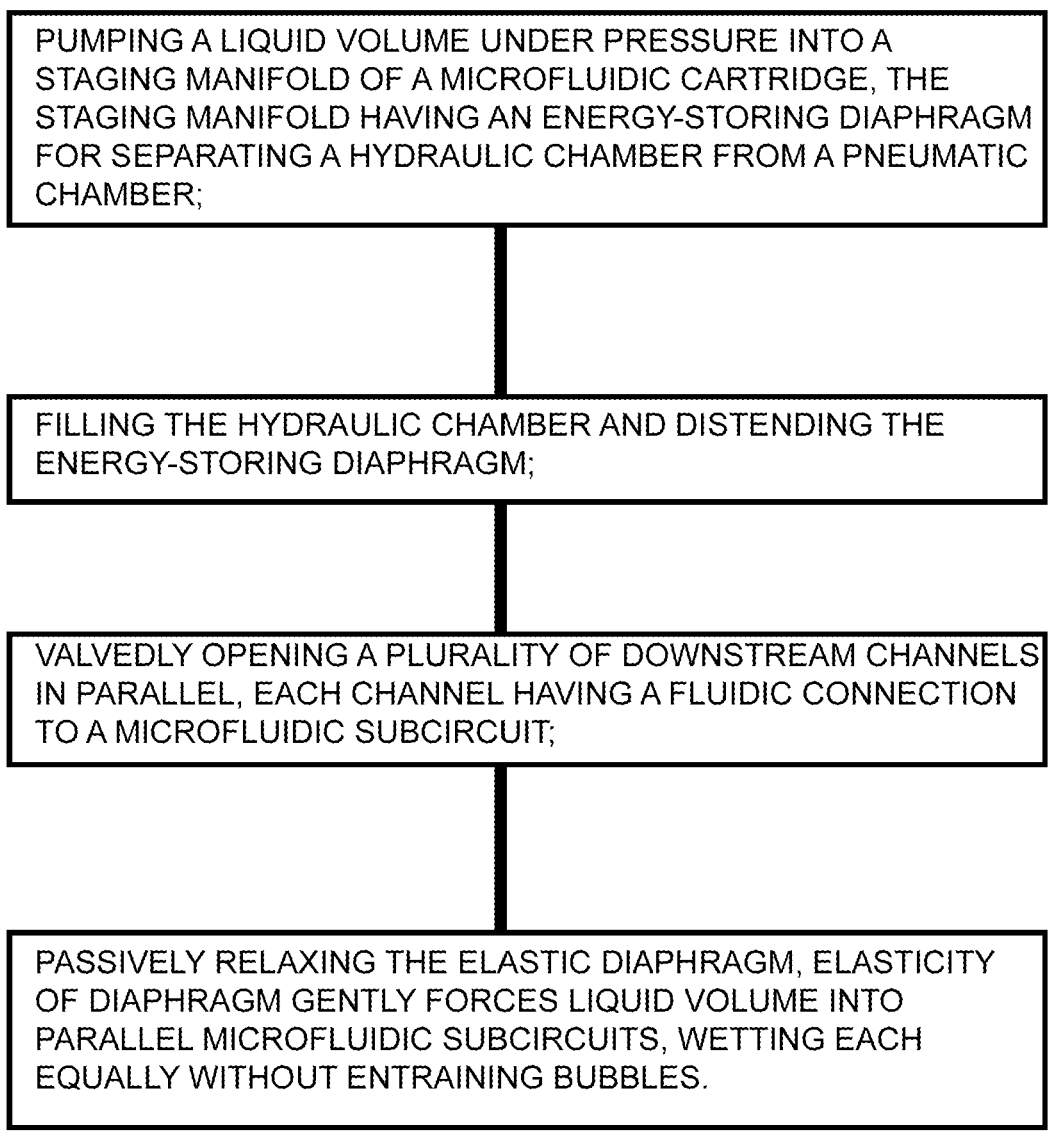
FIG. 12 describes the steps of a method for priming the microfluidic channels of a hydraulic works with liquids dispensed from a bilayered duplex diaphragm with liquid center.

FIGS. 11-13 summarize the steps of the methods described above. FIG. 11 describes the steps of a method for extracting nucleic acids from a sample, where a bilayered duplex diaphragm with liquid center is used to dispense the reagents. After starting the host instrument, a liquid sample is placed in a microfluidic cartridge and the cartridge is inserted in the docking bay of the instrument. The host instrument reads a bar code on the microfluidic cartridge indicating the type of assay to be run. The liquid sample is aspirated into a mixing chamber and cell lysis buffer is dispensed and mixed with the liquid sample. To dispense the lysis buffer a "liquid-centered diaphragm" is urged by pneumatic actuation against a sharp, rupturing the lower layer of the diaphragm and pumping the liquid into the card. The sample lysate is then contacted with a solid phase nucleic acid adsorbent positioned in a chamber in the card and the depleted sample lysate is directed to on-board waste. Ethanolic solution is dispensed from a second liquid-centered diaphragm member and used to wash contaminants from the solid phase adsorbent. The wash step may be repeated. The washes are sequestered to on-board waste. The solid phase matrix is briefly dried under a stream of air to remove residual solvent. Elution buffer is then dispensed from a final liquid-centered diaphragm reservoir and contacted with the solid phase matrix. The eluate with eluted nucleic acids 501 is then transferred to a staging manifold for entry into a detection subcircuit. In the example provided here, a nucleic acid assay with PCR amplification is conducted on the eluate. Other nucleic acid amplification methods are known in the art and, as would be understood from the teachings and drawings herein, may be practiced by reconfiguration of the various components of the devices of the invention FIG. 12 describes steps of a method for "priming" (i.e., wettingly loading) channels and chambers of a hydraulic works with liquids dispensed from a bilayered duplex diaphragm with liquid center 601 as pictured in FIG. 6D. After eluting a nucleic acid extract 501 with an elution buffer released by rupturing a reagent reservoir containing the buffer, the fluid can be oscillated when contacting solid phase absorbent 409 (FIG. 4) so as to efficiently take up adsorbed nucleic acids. The eluate is then pumped under pressure into a staging chamber of a microfluidic card so that an elastic diaphragm which covers the chamber becomes distended and stores the potential energy. The staging chamber inlet is sealed and pressure throughout the staging manifold equalizes rapidly. A downstream valve to each channel is then opened. All downstream fluid channels and chambers are vented during this operation, which is useful to wet out or prime the downstream wettable surfaces. Advantageously, as the elastic diaphragm relaxes, releasing its stored energy, the elasticity of the diaphragm gently but firmly forces a liquid volume into the downstream channels and chambers equally in parallel, the advancing meniscus displacing any residual air without bubble entrainment, an advance in the art. The liquid volume is split into branching parallel fluid pathways in this way.

FIG. 13 describes steps of a method for rehydrating dry reagents without bubble entrainment or reagent washout. During manufacture of a cartridge of the invention, a dried reagent spot is printed in the center of a reagent chamber. The reagent chamber is configured with an overlying pressurizable diaphragm. A liquid sample is added and the cartridge is inserted into the docking bay of a host instrument, which supplies pressure and valve commands for operation of the cartridge. The sample is first pumped under pressure into an unvented staging chamber, which distends an elastic energy-storing diaphragm covering the liquid in the staging chamber. The aforementioned downstream reagent chamber is vented and the pressurizable diaphragm therein is pressurized so as to form a protective temporary seal around and over the dried reagent spot. The downstream valve of the staging chamber is then opened; the elastic diaphragm relaxes and elastic energy of the diaphragm's recovery gently forces sample fluid into the downstream reagent chamber, displacing any residual air around the protective temporary seal. Finally, the pressure differential across the pressurizable diaphragm is reversed or relaxed, uncovering the reagent spot and aspirating a full volume of liquid into the reagent chamber so that the reagent spot advantageously dissolves at full strength in the sample fluid without bubble entrainment, an advance in the art.

Figure 14A:
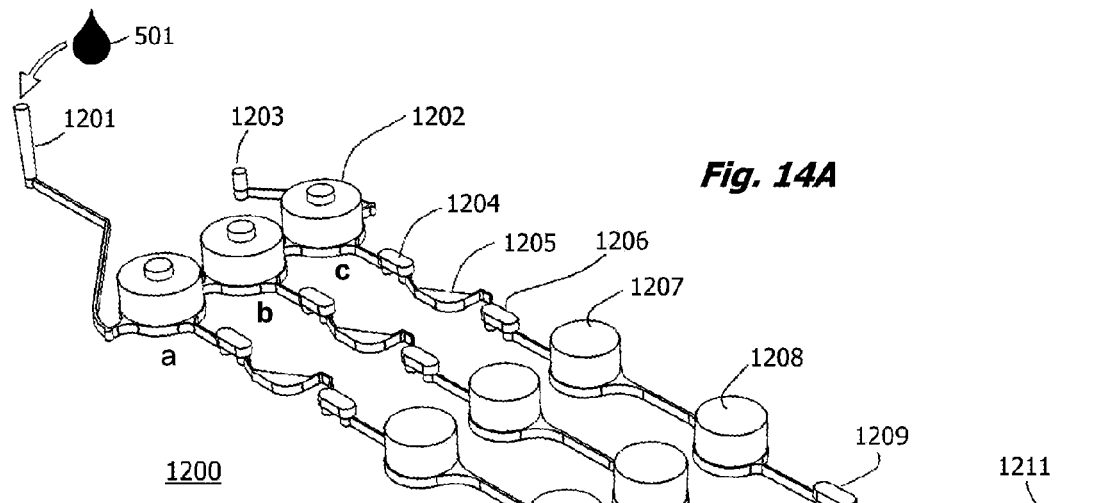
FIGS. 14A and 14C are worm's eye views of a network of microfluidic channels and chambers for reverse-transcriptase-mediate PCR.
Figure 14B:
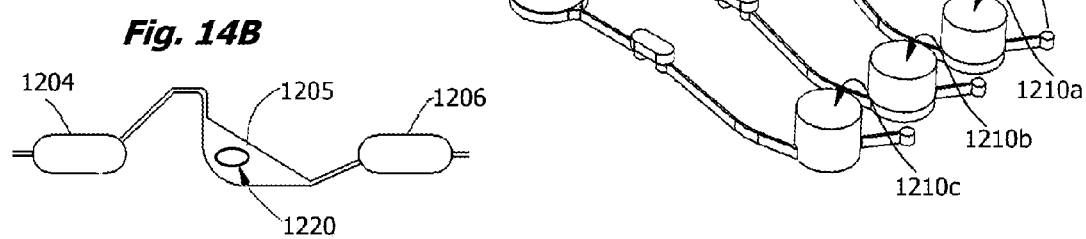
FIG. 14B is a detail view of an in-line chamber for production of cDNA.
Figure 14C:
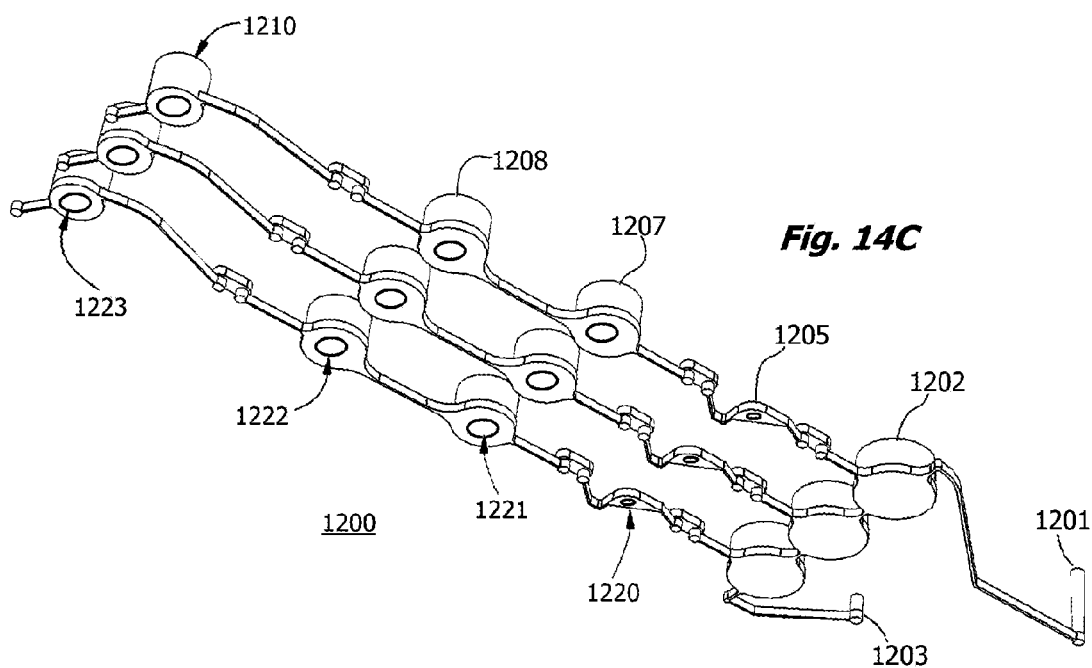

FIGS. 14A and 14C are worm's eye views of a network of microfluidic channels and chambers for reverse-transcriptase-mediated PCR. A device having three parallel channels a, b, and c is shown. Sample 501 is split between the channels so that three (or more) separate multiplex assays may be performed in parallel, for example. Unlike previously depicted embodiments, here a reagent 1220 is printed in a channel 1205 rather than in a diaphragm-actuated chamber. The passive wetting principle articulated in FIG. 9, however, is retained: liquid is expelled into the channel by the passive relaxation of an energy storing diaphragm that had been primed by an upstream pump. This principle is effective in limiting entrained air and in balancing fluid flow in parallel channels branching from a common staging manifold, where each channel provided with a discrete passive diaphragm. Devices utilizing this passively driven wetting principle, as realized herein, are an advance in the art, overcoming deficiencies associated with both capillary-wetted and actively-wetted devices of the prior art.

In one embodiment, FIGS. 14A and 14C show a network 1200 of channels and chambers for performing rtPCR within another microfluidic card of the invention. Depths of the channels and chambers in this "worms-eye" view are exaggerated for clarity. Eluate 501 (containing any nucleic acids of a sample) is ported into the card through via 1201 and enters a fluidly interconnected three-chambered staging manifold 1202, the purpose of which is to split the fluid into three downstream fluid pathways equally and to gently and evenly urge the fluid through downstream valves 1204, reagent channel 1205, valve 1206 and into chamber 1207 while avoiding entrainment of bubbles during initial wetout of internal plastic surfaces. Valves 1204 are initially closed.

During the first stage of the filling process, liquid 501 enters the poly-chambered manifold 1202 under pressure. Each chamber 1202 is bisected horizontally by an elastic diaphragm (see FIG. 9, 900) that segregates the fluid contents from a vented upper pneumatic cavity in the chamber and passively stretches during fill. During the fill, air beneath the diaphragms exits through vent 1203, which contains as a sanitary feature a gas permeable, liquid impermeable filter membrane that seals when wetted and allows an increase in pressure, distending the diaphragms. Continued pressurization inflates the diaphragms in chambers 1202 with liquid, so that when released by opening valves 1204 (and all downstream valves thereto), the pressurized liquid flows evenly into the three (or more) parallel downstream channels as urged by a restorative force exerted by the elastic diaphragms. The restorative pressure can be controlled and limited, and is a function of the spring constant of the diaphragm. The volumetric displacement of the elastic diaphragms can be controlled, so that the extent of wetout (or "priming") of the downstream channels is calibrated in the manner of volumetrically filling a pipet q.s. to a mark. The capacity to equally split a sample is advantageous in performing assays in parallel in a microfluidic device and has been problematic when attempted by capillary flow and by suction or positive displacement methods (such as a syringe pump) because there is no assurance that flow in each of the channels will progress at an equal rate. Surprisingly, using the principle of wetout driven by passive relaxation of mated diaphragms in a staging manifold, this problem is advantageously solved for multiple parallel channels.

Chambers 1207 and 1208 are fitted with internal diaphragms that interface between a hydraulic chamber and a pneumatic chamber. However, unlike the passively flexing diaphragm of chamber 1202, the pneumatic faces of the diaphragms of chambers 1207 and 1208 are not vented to atmosphere and can be actively driven by positive pneumatic pressure or negative pneumatic pressure supplied from an external source, thus serving as pumps. During the fill cycle, the diaphragms are fully distended down into the hydraulic cavity to as to reduce or eliminate any dead volume of the chambers. Liquid seeping past these diaphragms on the outside bottom edges of the chambers fully wets the chambers and displaces any residual air. Then upon releasing the diaphragms after closing valves 1209, liquid is aspirated under suction pressure from upstream and fills the entire volume of hydraulic chamber 1207, air having been entirely flushed from the system.

In a variant, one of the pneumatic chambers is vented to atmosphere, and is slaved to the action of the unvented diaphragm. The two chambers are isolated from the remaining circuit elements by valves. When the active diaphragm is pulsed with positive pressure, liquid is forced to the adjoining chamber; when the active diaphragm is pulsed with negative pressure, liquid is aspirated from the adjoining chamber. Optionally, the passive diaphragm may be an elastic diaphragm.

In a further refinement of this method, dry reagents are placed in chambers 1207 and 1208 and in channel 1205. The reagents are generally spotted on the floor of a hydraulic chamber or channel where the breadth of the passageway permits access by a printing head. The reagent 1220 spotted in channel 1205 comprises a reverse transcriptase and nucleotide substrates in a suitable buffer. Typically a PCR master mix and suitable primers are provided as reagent spot 1221 in chamber 1207. Spot 1222 is a dehydrated Taq reagent spot. Spot 1223 includes optional detection reagents, such as a fluorescent probe. Multiple separate spots may be printed using a roll-type or sheet-type process in each chamber or channel.

RNA target in the eluate 501 is converted to cDNA by the action of reverse transcriptase, generally at a temperature of 20 to 45° C. This action is effected within channel 1205 in the elution buffer, and is depicted in more detail in FIG. 14B, where valves 1204 and 1206 are separated by a modified channel segment 1205 containing a dried reagent spot 1220. The reagent, for example a reverse transcriptase, is dissolved in sample transiting the specially modified channel segment. Substrates and any cofactors for full enzyme activity are also provided.

During initial wetout, diaphragms in chamber 1207 and 1208 are fully distended down into the hydraulic chamber so as to reduce the dead volume therein and the covering provided by the diaphragm protectively seals the underlying dry reagent spot or spots from premature dissolution and washout during wetting. Vent 1211 is open to exhaust air that is displaced by entry of the fluid, generally as a smoothly advancing meniscus. After valve 1209 is closed and the chamber 1207 is filled with liquid by reversing pressure across the diaphragm (i.e. aspirating the liquid into the chamber), valve 1206 is also closed. Any spotted reagent dissolves rapidly and at full strength, without dilution, essentially as described with respect to FIG. 8 for a direct PCR process, where there was no need to form a cDNA from an RNA target. Reconfiguration of the device is thus flexible and may be adapted to a variety of molecular assay processes.

Figure 17:
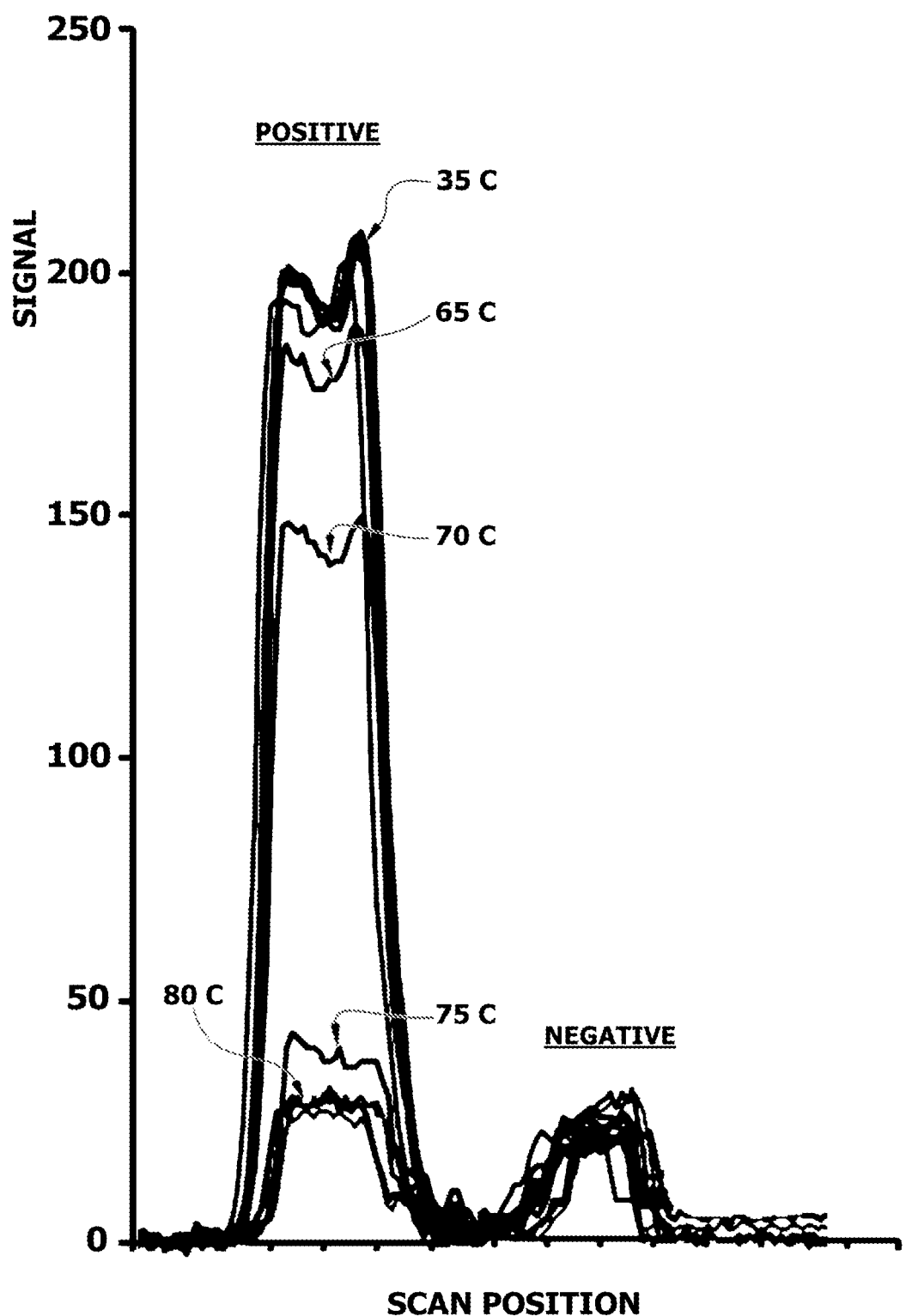
FIG. 17 is a plot showing a positive and negative fluorescence assay in the detection chambers of the cartridge, including multiple scans of the sample while increasing the temperature of the reaction mix.
Figure 18A:
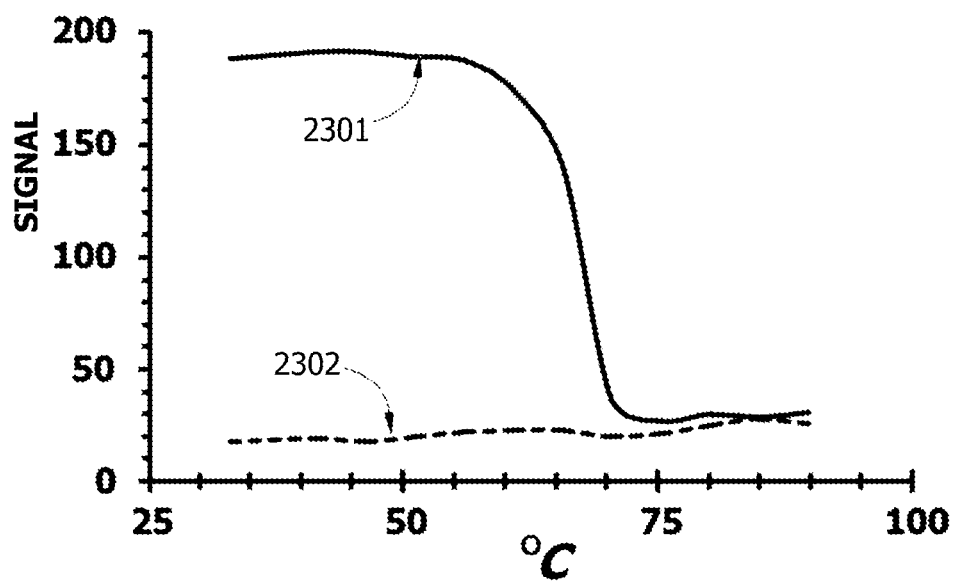
FIGS. 18A and 18B analyze the pooled data of FIG. 17. Scans of a molecular beacon-amplicon duplex demonstrate a FRET melting curve capability of the cartridge when interfaced with a compatible host instrument.
Figure 18B:
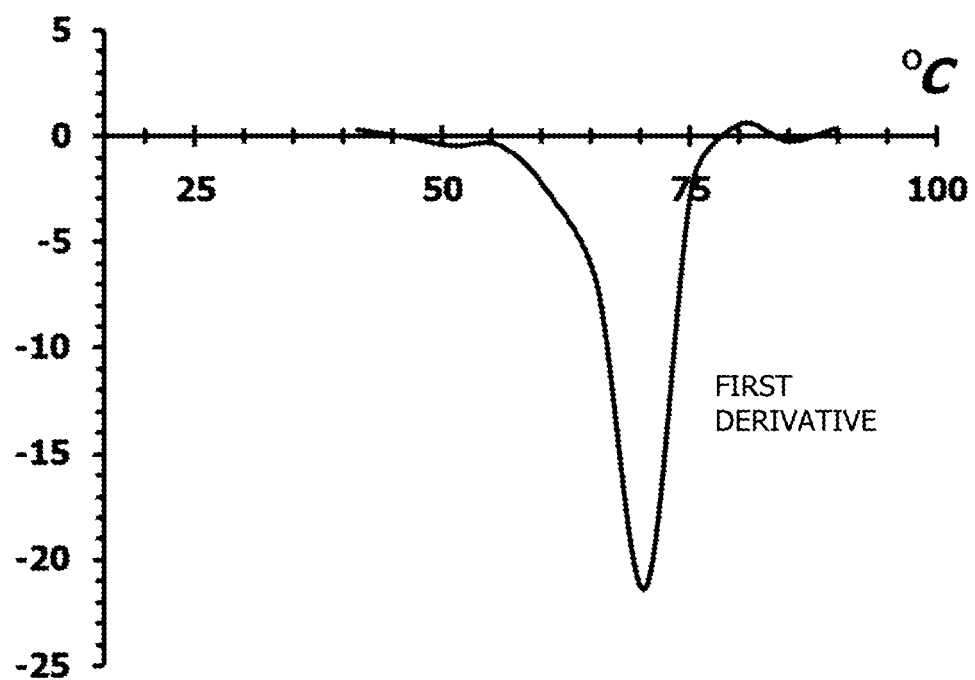

Chamber 1207 is preferentially heated at a temperature sufficient for the denaturing of template nucleic acid. Chamber 1208 contains for example dried polymerase 1222 and is at a temperature suitable for annealing of primers and target and for initiation of polymerization. Hot start of PCR is initiated for example by dissolution of a Taq polymerase reagent spot 1222 in chamber 1208. Then, by alternating pressure applied to the diaphragms of the two chambers 1207 and 1208, fluid may be moved back and forth from denaturing to annealing conditions by a reciprocating pneumohydraulic action of the diaphragms, and chain elongation and amplification has been found to be successful in generating amplicons during this process. In the detection chamber 1210, dry reagent spot 1223 contains probes such as, for example, "molecular beacons" which are used to detect any amplicon produced in the amplification. As before, detection chamber 1210 is bounded on top and bottom by thin film optical windows and is reflectively transilluminated for fluorometric detection of amplified target. Synergically, the bottom thin film layer is also effective in heat transfer from the mirror faced heating element shown in FIG. 3B, with which the card interfaces during the assay, and can thus be termed a "thermo-optical window", such as is useful in assaying or confirming amplicon identification by thermal melting curves as will be described below (FIGS. 17, 18A and 18B).

Figure 14D:
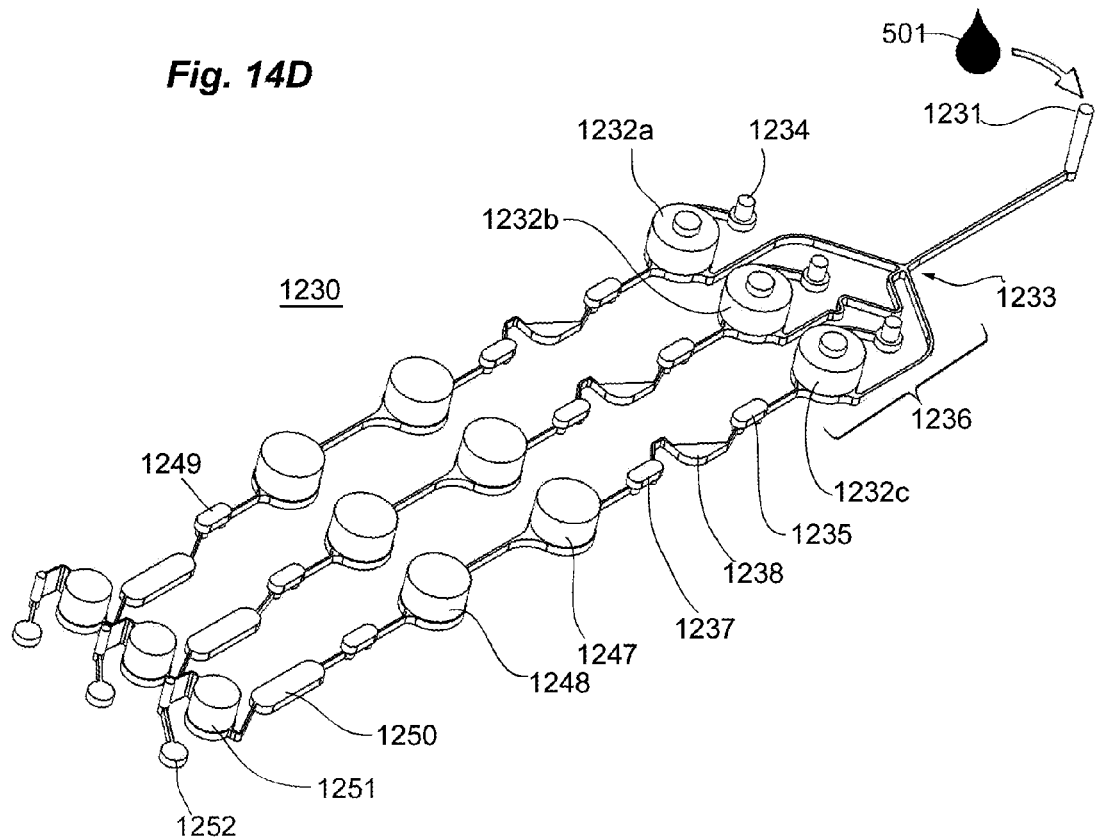
FIGS. 14D and 14E illustrate an alternative configuration of a cartridge with modified features.
Figure 14E:
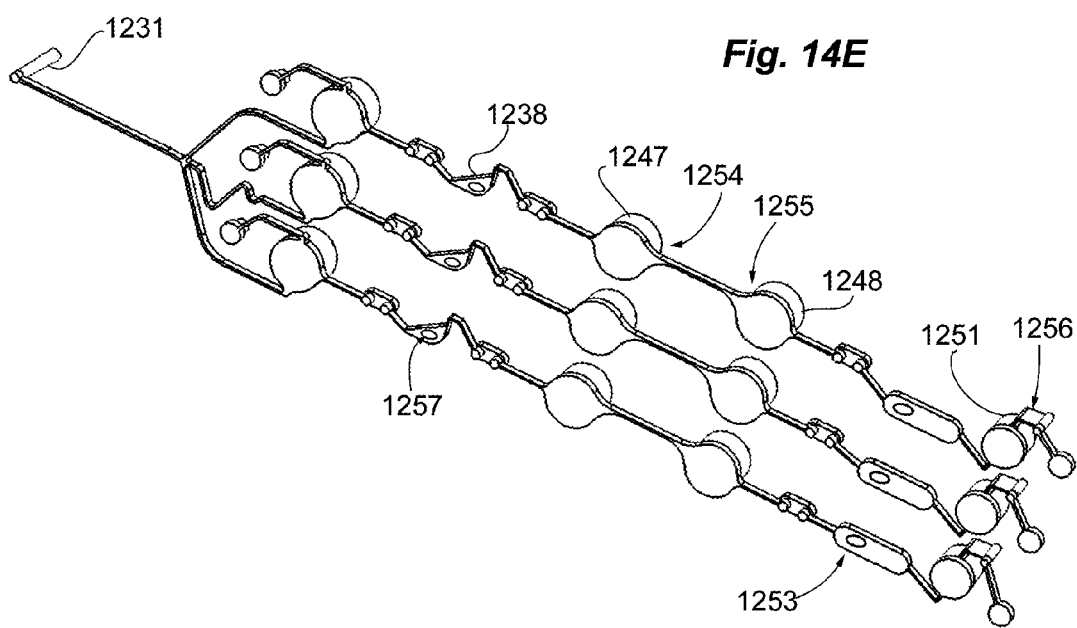

FIGS. 14D and 14E describe an alternative cartridge 1230 for PCR. In this cartridge, eluate 501 entering the cartridge under pressure at sample inlet 1231 is split at trifurcation 1233 and fills each of three chambers 1232a, 1232b, and 1232c, which are independently vented at hydrophobic vents 1234. Each chamber 1232 contains an elastic pneumohydraulic diaphragm, which when stretched or distended exerts a pressure on the liquid volume contained in the chamber. If needed, the chambers may be filled by injecting a series of pressurized volumes from an upstream pump; fluid flow into the three branches of the distribution manifold is not necessarily split equally, but volume and pressure in each chamber (1232a, 1232b, 1232c) become equalized as the staging manifold equilibrates. During the fill process, downstream valves 1235 are closed.

After pressurization of the staging manifold 1236 is completed, valves 1235 and 1237 are opened so that the elastic diaphragm of chambers 1232 can relax while passively urging the liquid contents into reverse transcription channel 1238. Reverse transcription is conducted under buffer, substrate and temperature conditions adapted for reverse transcriptase; buffer and any enhancers are generally supplied as a dried reagent spot 1257 in chambers 1238. The sample is then urged into amplification chambers 1247 and 1248. Each amplification chamber is fitted with a pneumohydraulic diaphragm. During this process, the diaphragm elements of chambers 1247 and 1248 are inflated under pneumatic pressure so that headspace is removed and any dried reagents in the chambers are protected from being washed away by the advancing meniscus by the inflated diaphragms, which are tented into the hydraulic chambers to cover the reagent spots. PCR amplification is performed on cDNAs made by reverse transcription as described for FIGS. 14A and 14C. Downstream valve 1249 is opened to convey any amplification products through an antechamber 1250 to a detection chamber 1251 by pressurizing diaphragms in both chambers 1247 and 1248 while valve 1237 is closed. At each stage, any air in the system is flushed out through terminal vent 1252. Advantageously, dried probe 1253 printed or spotted in the antechamber 1250 is dissolved and mixed with amplicon prior to injection into the detection chamber, which improves the transparency of the thermo-optical window bounding the detection chamber and reduces or prevents autofluorescence of certain dyes useful as molecular beacons or FRET probes.

As can be seen in FIG. 14E, the inlet, outlet, and venting ports of detection chamber 1251 and the amplification chambers 1247 and 1248 are asymmetrically placed. When the device is canted on a tilted stage of the host instrument (referencing FIGS. 3A and 7B), communicating ports (1254, 1255) between the amplification chambers and at the terminal venting port (1256) associated with the detection chamber are elevated relative to the chambers themselves and are contoured to overcome any surface tension effects of the geometry. Air in the system is thus preferentially flushed from the system by the advancing liquid during wetout, which fills the lower aspects of the chambers first, and any bubbles generated by heating-associated degassing of the liquid during reciprocal pumping for PCR are preferentially trapped between the amplification chambers so as to not interfere with heat transfer, and do not enter the detection chamber.

Alternatively, reverse transcriptase cDNA and amplification may be performed in one of the cartridges of FIG. 8. This is achieved by spotting reverse transcriptase (MMLV-RT, AMV-RT) and substrates in first amplification chamber 804 and by first incubating at 40 to 50° C. Nucleic acids are extracted in the presence of an RNAase inhibitor. Suitable buffers for one-pot rtPCR are described in the literature and result in what is essentially a pre-amplification of RNA targets, thus improving sensitivity and the range of detectable molecular targets. Buffer systems for one-pot rtPCR are described for example by Young [Young et al. 1993. Detection of Hepatitis C virus RNA by a combined reverse transcription-polymerase chain reaction assay. J Clin Microbiol 31:882-86] and by others. Generally an RNAase inhibitor is added.

Figure 15:
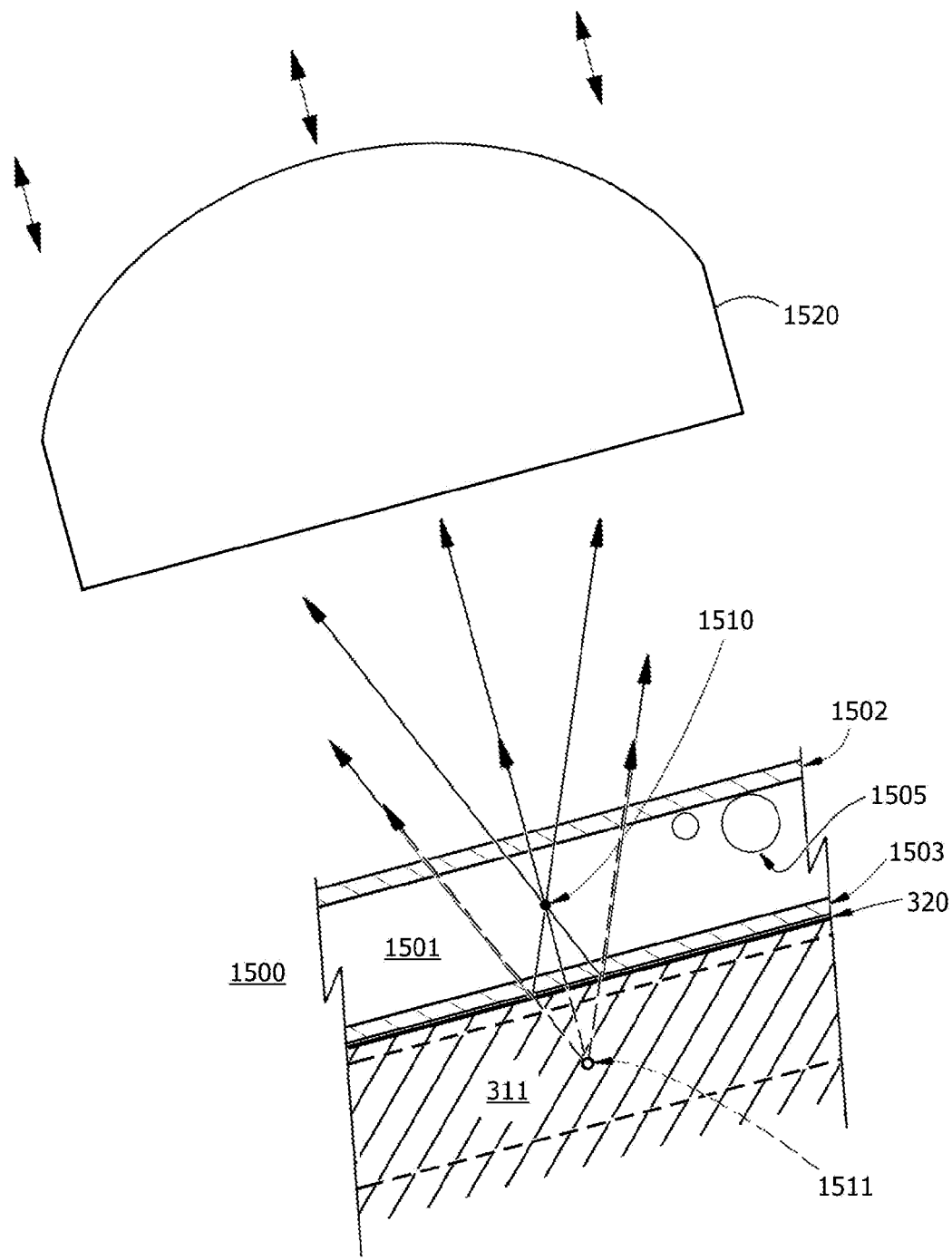
FIG. 15 illustrates use of optical windows of a detection chamber of a device of the invention for monitoring a fluorescent endpoint.

FIG. 15 illustrates use of optical windows of a detection chamber of a device of the invention for monitoring a fluorescent endpoint. An objective lens 1520 is used to transilluminate a detection chamber 1500 holding a liquid sample 1501. The detection chamber is bounded by an upper optical window 1502 and a lower optical window 1503. The chamber rests on a mirror face 320 of a heating block 311, the heating block thus fulfilling dual functions of reflecting back the optical path for reflected light rays absorbed or emitted by chromogens or fluorophores in the chamber and for modulating the temperature of detection chemistry in the fluid. This configuration has value for example in FRET detection and for confirmation of detection of nucleic acid targets.

Photons emitted by a target molecule 1510 may be emitted in a cone that is capture by the objective lens or may be reflected from mirror face 320, thus forming a virtual image 1511 of the target molecule, and again are captured by the objective lens, increasing sensitivity. The detection chamber is thus mirrored by a "virtual detection chamber" (dotted lines) in the body of the heating block 311. Advantageously, bubbles 1505 forming in the detection chamber are gravitationally urged away from the center of the chamber by the inclination angle theta at which the device is disposed in the docking bay within the host instrument (see FIG. 7B). Synergically, the mirror-smooth surface 320 also improves heat transfer, and lower optical window 1503 also serves as a heat transfer film. The heat transfer film is advantageously very thin and is forced into thermal contact with heating block 311. A preferred heat transfer film is described in U.S. Pat. Nos. 7,544,506 and 7,648,835, which are coassigned, but may also include cyclic polyolefin films of similar dimensions, for example. The assembly thus functions as a thermo-optical window, achieving improved heating and optical interrogation of any amplicons or other detectable species present.

FIG. 16 depicts a representative level of complexity of the microfluidic works for performing PCR and a pneumatic interface with gasket for interfacing the microfluidic works with a host instrument. Shown for purposes of illustration are fluidic channels and chambers comprising a hydraulic works with microfluidic subcircuits and a pneumatic works for operating a molecular detection assay, exemplary details of which have been described here. An outboard card 410 and an inboard card 400 are joined at a common pneumatic junction which is sealed using a disposable gasket 405 during operation to the pneumatic control interface in order to pneumatically control and drive the hydraulic workings of the cards. This subassembly 1600 is generally mounted in a cartridge chassis containing reagent reservoirs as described with reference to FIG. 4. The microfluidic works of the cards include the hydraulic works formed of a network or networks of internal channels and chambers that are wetted in the course of the assay and the pneumatic works formed of valve control and pump driving circuits powered by positive and negative gas pressure sources on the host instrument. Diaphragm valves are pneumatically opened and closed to control steps of the assays. Larger diaphragms disposed at the interface between the hydraulic works and the pneumatic works also serve as pneumohydraulic devices for moving fluids and also for converting kinetic motion of fluids into potential energy in the form of elastically distended diaphragm elements of a staging manifold and/or passively driven pumps in the amplification chambers, for example. In this figure, the outboard card 410 is responsible for nucleic acid extraction from a biological sample, and the inboard card 400 is used for amplification and detection. Other combinations are readily conceived within the scope and spirit of the invention, which is not limited by the illustrative examples provided.

FIGS. 17, 18A and 18B are representative of the types of assay results obtained with the microfluidic cartridges of the present invention, while not limiting thereto. FIG. 17 shows scanning data collected for a molecular beacon hybridized to an amplicon. The scanning axis (x-axis of plot) transects detection wells representing positive and negative test conditions respectively, and it can be seen that signal is limited to the detection wells. In the figure, the sample is scanned repetitively as the temperature in the detection chamber is systematically varied. The scans are overlaid in the plot to illustrate the spatial fidelity of the optical scanning apparatus. Fluorescence scans for 35° C., 65° C., 70° C., 75° C. and 80° C. test conditions are marked. Test scans at 40, 45, 50, 55, and 60° C., and the 85 and 90° C. plots were not well differentiated, as would be expected, and are not individually marked. It can be seen that fluorescent signal is a function of temperature. Fluorescence quenching in this example is observed to increase as the double stranded probe-target is melted, ie. signal is greatest at 35° C. and is essentially not present at 80° C. In FIG. 18A, the data is replotted for signal versus temperature for the positive (2301, solid line) and negative (no target, 2302, dotted line) test conditions. In FIG. 18B, a first derivative is plotted, indicating a FRET melt temperature of about 70° C.

Example I

By example, the apparatus of the invention is shown to be useful in diagnosis of infectious disease by detection of the nucleic acids of a pathogen in a human sample such as feces. Of interest by way of illustration were the rfb gene useful in genetically detecting Enterobacteriaceae-like O-antigen serotype and the $stx_1$ and $stx_2$ genes (for shigatoxins). These genes are found for example in Shigella, Salmonella, Campylobacter, and Escherichia coli serotypes of interest in diarrheal disease.

Negative fecal swabs were diluted in 2.5 mL of PBS and spiked with O157:H7 bacterial culture. Diluted samples 250 uL were loaded for analysis onto a cartridge of the invention. These cartridges contained all required dried and liquid reagents for PCR and molecular beacon amplicon detection. After DNA extraction, target and primers were denatured at 94 C for 2 minutes and then cycled for PCR amplification at about 12 sec per thermal cycle. After loading, an instrument having thermal, pneumatic and optical interfaces designed to be compatible with the cartridge was used to run a multiplex nucleic acid assay on the sample. Bacteroides DNA was used as an internal positive control on the amplification; negative controls were also run and produce no false positives.

A FAM-labelled probe for bacteroides is detected by a first fluorescence (excitation 485 nm, emission 535 nm). A CAL fluor Red 610-labelled probe (excitation 590 nm, emission 610 nm) is used to detect the target analyte in this assay. Biplex amplification products were detected at or near a minimum of 80 target copies per extract against an internal control background estimated at 400,000 copies, indicating a high level of sensitivity and specificity. Details of the optics are described in World Patent Application Publication No. PCT/US10/22581, titled PORTABLE HIGH GAIN FLUORESCENCE DETECTION SYSTEM, which is copending and is incorporated in full by reference for all purposes herein.

Figure 19:
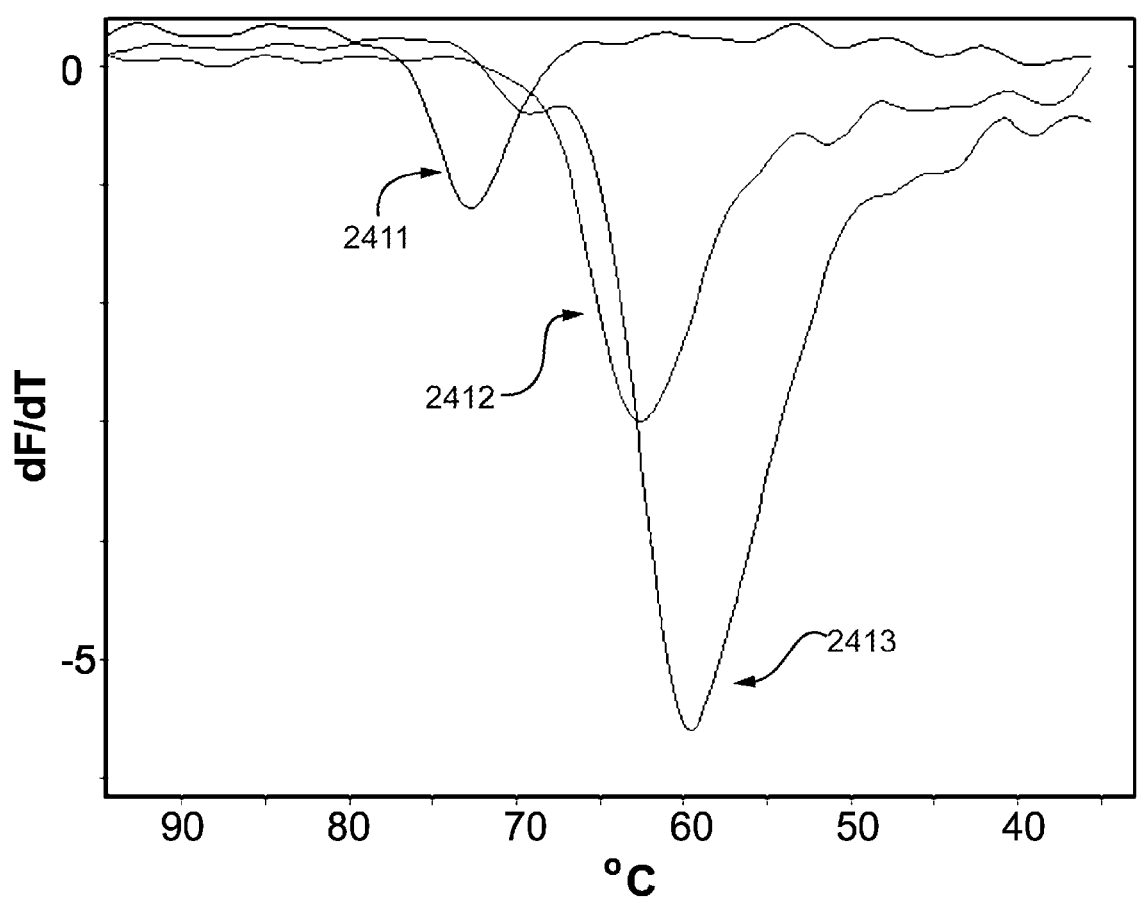
FIG. 19 depicts FRET data for amplicons obtained with a device of the invention when used in a host instrument compatible therewith.

FRET curves for amplicons detected for stx2 (2411), stx1 (2412), and rfb (2413) genes in fecal samples in a device of the invention are illustrated in FIG. 19. Control data is not shown.

Example II

Using on-board dry and liquid reagents, a blood sample may be processed and RNA associated with Measles virus detected in 30 minutes or less. In a first step, cDNA is formed from the sample at an incubation temperature of about 50 C in one of the devices shown in FIG. 14, and the reverse transcriptase product is then subjected to PCR using two microfluidic chambers (1221, 1222) with dual temperature zone control generally as described in U.S. Pat. Nos. 7,544,506, 7,648,835, 7,763,453, and 7,763,453 which are co-assigned, and in pending applications titled, "Integrated Nucleic Acid Assays", which are co-assigned and incorporated in full by reference for all purposes herein. Amplicon is then detected using a FAM fluorescence-tagged molecular beacon directed at the amplified target. Optionally, a control consisting of a California Red-tagged RNAase P leukocyte exon sequence (which is generally characteristic of any genuine human blood sample) with multiplex amplification in a one-pot reaction mixture, is used to validate the assay.

Other examples illustrating various combinations of inventive elements and features are readily demonstrated. Devices configured per the teachings of the invention may be used in molecular assays for a target nucleic acid (either DNA or RNA) associated with, for example, an infectious agent selected from a bacterium (including Acinetobacter baumannii, Actinobacillus equuli, Bacillus anthracis, Brucella melitensis, Brucella abortus, Bordatella pertussis, Bordatella bronchioseptica, Burkholderia pseudomallei, Corynebacterium diptheriae, Coxiella burnetii, Eikenella corrodens, Escherichia coli, Francisella tularensis, Francisella novicida, Fusobacterium necrophorum, Haemophilus influenzae, Klebsiella oxytoca, Klebsiella pneumoniae, Kingella denitrificans, Legionella pneumophila, Leishmania ssp, Listeria monocytogenes, Moraxella catarrhalis, Mycobacterium tuberculosis, Mycoplasma pneumoniae, Neisseria gonorrhoeae, Neisseria meningitides, Pasteurella multocida, Proteus vulgaris, Proteus mirabilis, Pseudomonas aeruginosa, Pseudomonas putrefaciens, Pseudomonas cepacia, Salmonella typhi, Shigella dysenteriae, Staphylococcus aureus, Streptococcus pyogenes, Streptococcus pneumoniae, Treponema pallidum, Yersinia pestis, or Vibrio cholera), a Rickettsial agent (including Chlamydia pneumoniae, Chlamydia trachomatis, Rickettsia prowazekii, or Rickettsia typhi), a viral agent (including Measles virus, HIV virus, Hepatitis C virus, Hepatitis B virus, Dengue Virus, Western Equine Encephalitis virus, Eastern Equine Encephalitis virus, Venezuelan Equine Encephalitis virus, Enteroviruses, Influenza virus, bird flu, Coronavirus, SARS Coronavirus, Polio virus, Adenovirus, Parainfluenza virus, Hanta virus, Rabies virus, Argentine Hemorrhagic Fever virus, Machupo virus, Sabia virus, Guanarito virus, Congo-Crimean Hemorrhagic Fever virus, Lassa Hemorrhagic Fever virus, Marburg virus, Ebola virus, Rift Valley Fever virus, Kyasanur Forest Disease virus, Omsk Hemorrhagic Fever, Yellow Fever virus, Smallpox virus, a retrovirus, Monkeypox virus, and foot and mouth disease virus), a fungal agent (including *Coccidiodes immitis, Candida albicans, Cryptococcus neoformans, Histoplasma capsulatum, Blastomyces dermatitidis, Sporotrhix schenki*, or *Aspergillus fumigates*), a parasitic agent (including *Plasmodium falciparum, Plasmodium vivax, Plasmodium ovale, Plasmodium malariae, Toxoplasma gondii, Plasmodium bergeri, Schistosoma mansoni, Schistosoma hematobium, Schistosoma japonicum, Entamoeba histolytica, Babesia, Toxoplasma gondii, Trypanosoma cruzi, Leishmania* ssp, *Trypanosoma brucei, Trichinella spiralis, Toxocara canis, Necator americanus, Trichuris trichura, Enterobius vermicularis, Dipylidium caninum, Entamoeba histolytica, Dracunculus medinensis, Wuchereria bancrofti, Brugia malai, Brugia timori, Strongyloides stercoralis, Ascaris lumbricoides, Onchocerca volvulus, Naegleria fowleri, Clonorchis sinensis, Cryptosporidium parvum, Leishmania* spp), or also a gene or a sequence including an antibiotic resistance gene, a gene associated with virulence or toxigenicity, a molecular marker, a single-nucleotide polymorphism, an insect gene, a bee disease agent gene, a plant gene, a plant disease agent, a molecular marker associated with a cell having a pathogenic or carcinogenic condition, a mitochondrial nucleotide sequence, a plasmid sequence, a messenger RNA, a ribosomal RNA, or a panel of target nucleic acids, and the like, as may be interesting or useful. And may be used in molecular diagnosis of infectious agents in a mammal or vertebrate, including livestock, veterinary and aquaculture applications broadly. And also diagnostic applications in plants, animals or insects suffering more generally from a pathogenic condition, for example, infectious or otherwise Immunological and biochemical assays employing cartridge devices having the features of the invention are also conceived and claimed for diagnostic use.

While the above is a description of the preferred embodiments of the present invention, it is possible to use various alternatives, modifications, combinations, and equivalents. Therefore, the scope of the present invention should be determined not with reference to the above description but should, instead, be determined with reference to the appended claims, along with their full scope of equivalents. The appended claims are not to be interpreted as including means-plus-function limitations, unless such a limitation is explicitly recited in a given claim using the phrase "means for."

All of the U.S. patents, U.S. patent application publications, U.S. patent applications, foreign patents, foreign patent applications and non-patent literature and publications referred to in this specification and/or cited in accompanying submissions, are incorporated herein by reference, in their entirety. Aspects of the embodiments may be modified, if necessary to employ concepts of the various patents, applications and publications to provide yet further embodiments. These and other changes may be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the specifics of the disclosure.

What is claimed is:

1. A microfluidic cartridge for assay of a target analyte or analytes in a biological sample, which comprises:
   a) a plastic, thermally insulative cartridge body enclosing:
   i) a hydraulic works comprising a sample inlet, one or more on-board liquid or dry reagents for an assay, and a wettable downstream microfluidic subcircuit with channels and chambers fluidly connected to said sample inlet and vented at a downstream vent; and
   ii) a pneumatic works comprising an inlet or inlets for receiving pneumatic pressure and a pneumatic subcircuit with channels and chambers for conveying said pneumatic pressure therefrom; and
   b) an on-board reagent reservoir for dispensing a liquid volume into a microfluidic subcircuit of said hydraulic works; wherein said reagent reservoir comprises:
   i) a duplexedly layered diaphragm sealedly separating a pneumatic chamber of said pneumatic works and a hydraulic chamber of said hydraulic works, said duplexedly layered diaphragm having a first side facing said pneumatic works and a second side facing said hydraulic works, a first layer forming said first side thereof, and a second layer forming said second side thereof, said first and second layers enclosing said liquid volume as a liquid center therebetween;
   ii) a fluid outlet for receiving and conveying said liquid volume to said downstream microfluidic subcircuit; and
   iii) a sharp disposed in said hydraulic chamber, said sharp for rupturing said second layer and for releasing said liquid volume into said hydraulic works when said duplexedly layered diaphragm is piercingly urged into contact with sharp by application of a pressure differential across said duplexedly layered diaphragm,
   wherein said hydraulic works is mounted at a tilt angle theta of 10-35 degrees relative to the ground plane on a tilted stage of a host instrument and at least one hydraulic chamber comprises an outlet and intercommunicating channel positioned superiorly relative to said at least one hydraulic chamber for venting a gas or discharging a bubble from said chamber, and the microfluidic cartridge further comprises:
   i) a staging manifold having a plurality of chambers, wherein each said chamber of said plurality of chambers is separated into a hydraulic chamber and a pneumatic chamber by an elastic, energy-storing pneumohydraulic diaphragm sealedly mounted therebetween, such that a liquid volume admitted through an inlet into each said hydraulic chamber in series or in parallel distends each said energy-storing pneumohydraulic diaphragm according to an isobaric pressure proportionate to the displacement volume thereof, and wherein said inlet into each said hydraulic chamber is valvedly closeable for equilibrating said hydraulic pressure throughout said staging manifold after filling is complete; and
   ii) a plurality of vented downstream channels in parallel, wherein one said channel of said plurality of channels is in fluidic communication with each said hydraulic chamber of said staging manifold, each said vented downstream channel having a valve for closing during filling and pressurization and for opening during draining and depressurization, whereby said hydraulic pressure of said elastic, pneumohydraulic diaphragm in a distended state is passively converted to the work of advancing a meniscus during initial wetout of said plurality of vented downstream channels in parallel.

2. The microfluidic cartridge of claim 1, wherein said hydraulic works comprises a plurality of wettable downstream microfluidic subcircuits with channels and chambers fluidly connected to said sample inlet and vented at one or more downstream vents, wherein each of said plurality of wettable microfluidic subcircuits is provided with a separate detection chamber.

3. The microfluidic cartridge of claim 1, wherein said duplexedly layered diaphragm is a polyurethane diaphragm, a polyvinylidene chloride diaphragm, a polyolefin diaphragm, a polyester diaphragm, a polyethylene diaphragm, a polyethylene terephthalate diaphragm, a nylon diaphragm, or a laminated or co-extruded combination thereof, and optionally includes a metallized film layer.

4. The microfluidic cartridge of claim 1, wherein each said downstream vented channel comprises an inlet to a microfluidic subcircuit, and wherein each said elastic, energy-storing pneumohydraulic diaphragm is adapted for splitting a liquid volume equally between each said downstream microfluidic subcircuit.

5. The microfluidic cartridge of claim 4, wherein said each microfluidic subcircuit comprises at least one reaction chamber with provision for mixing a liquid reagent, a dry reagent, or a combination thereof, with a liquid sample, and at least one detection chamber interfacing with a detection means for detecting a target analyte or analytes.

6. The microfluidic cartridge of claim 1, wherein said pneumatic chamber of said pneumatic works is vented to atmosphere.

7. The microfluidic cartridge of claim 1, wherein said first layer of said duplexedly layered diaphragm is rupture resistant and said second layer is rupture sensitive.

8. The microfluidic cartridge of claim 7, wherein said first layer is a laminated polymer with outer nylon base layer configured to be puncture resistant and said second layer is a laminated polymer with outer polyethylene terephthalate member, wherein said outer polyethylene terephthalate member is puncture susceptible.

9. The microfluidic cartridge of claim 1, wherein said on-board reagent reservoir releases serial liquid volumes by the action of serial pulses of pneumatic pressure applied thereto.

10. The microfluidic cartridge of claim 1, wherein said liquid volume comprises a liquid reactant, a buffer, a rehydrating fluid, or a diluent, said liquid volume for an assay step selected from rehydrating a dry reagent disposed in a downstream chamber or channel, for rinsing a solid phase, for eluting a target analyte or analytes from a solid phase substrate, for making a dilution, for performing a chromatographic separation, for actuating or stopping a reaction, or for detecting said target analyte or analytes and optionally wherein said liquid volume is degassed and said duplexedly layered diaphragm is gas impervious.

11. The microfluidic cartridge of claim 1, wherein said microfluidic cartridge further comprises:
a first pneumohydraulic diaphragm overlying a first hydraulic chamber and a second pneumohydraulic diaphragm overlying a second hydraulic chamber, said first and second hydraulic chambers having a fluidically interconnecting channel;
a thermal interface for two-zone PCR thermocycling, with first thermal interface of said first hydraulic chamber configured for apposing a first heating element and second thermal interface of said second hydraulic chamber configured for apposing a second heating element;
wherein said first pneumohydraulic diaphragm comprises a pneumatic means for driving reciprocal fluid flow between said first and second hydraulic chambers during PCR amplification, and
wherein said interconnecting channel is configured to be operated at a tilt angle theta of 10-35 degrees so as to reduce interference from bubbles.

12. The microfluidic cartridge of claim 11, wherein said second pneumohydraulic diaphragms is an elastomeric diaphragm and is worked passively by the urging of said first pneumohydraulic diaphragm.

13. The microfluidic cartridge of claim 1, further comprising a detection chamber enclosed on a first opposite side by an optical window and on a second opposite side by a thermo-optical window; and
wherein said detection chamber is operated at a tilt angle theta of 10-35 degrees so as to flush air and bubbles to a vented port superiorly disposed thereon.

* * * * *